(12) United States Patent
Brune et al.

(10) Patent No.: US 7,855,308 B2
(45) Date of Patent: Dec. 21, 2010

(54) INHIBITORS OF THE 11-BETA-HYDROXYSTEROID DEHYDROGENASE TYPE 1 ENZYME

(75) Inventors: Michael E. Brune, Mundelein, IL (US); Peer B. Jacobson, Libertyville, IL (US); James T. Link, Stanford, CA (US); Jyoti R. Patel, Libertyville, IL (US); Jeffrey J. Rohde, Evanston, IL (US); Qi Shuai, Dekalb, IL (US); Martin Winn, Deerfield, IL (US); Vince S. Yeh, San Diego, CA (US); Hong Yong, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 12/355,909

(22) Filed: Jan. 19, 2009

(65) Prior Publication Data

US 2009/0131434 A1 May 21, 2009

Related U.S. Application Data

(62) Division of application No. 11/325,965, filed on Jan. 5, 2006, now Pat. No. 7,511,175.

(60) Provisional application No. 60/641,520, filed on Jan. 5, 2005.

(51) Int. Cl.
*C07C 233/05* (2006.01)
*A61K 31/65* (2006.01)

(52) U.S. Cl. .............. 564/155; 564/182; 564/191; 564/192; 562/498; 562/507; 548/204; 548/254; 548/335.5; 546/272.7; 546/336; 544/124; 514/237.8; 514/357; 514/365; 514/396; 514/534; 514/616; 514/617

(58) Field of Classification Search .............. 564/155, 564/182, 191, 192; 562/498, 507; 548/204, 548/254, 335.5; 546/272.7, 336; 544/124; 514/237.8, 357, 365, 396, 534, 616, 617
See application file for complete search history.

(56) References Cited

U.S. PATENT DOCUMENTS

| | | | |
|---|---|---|---|
| 4,273,704 A | 6/1981 | Mazur | |
| 4,324,791 A | 4/1982 | Welstead, Jr. | |
| 4,514,332 A | 4/1985 | Hansen, Jr. et al. | |
| 4,751,292 A | 6/1988 | Fox | |
| 4,921,958 A | 5/1990 | Abou-Gharbia et al. | |
| 5,397,788 A | 3/1995 | Horwell et al. | |
| 5,622,983 A | 4/1997 | Horwell et al. | |
| 6,368,816 B2 | 4/2002 | Walker et al. | |
| 6,784,167 B2 | 8/2004 | Wood et al. | |
| 7,087,400 B2 | 8/2006 | Walker et al. | |
| 7,122,531 B2 | 10/2006 | Walker et al. | |
| 7,217,838 B2 | 5/2007 | Rohde et al. | |
| 7,435,833 B2 | 10/2008 | Yeh et al. | |
| 7,511,175 B2 * | 3/2009 | Patel et al. .................. 564/86 |
| 2004/0122033 A1 | 6/2004 | Nargund et al. | |
| 2004/0133011 A1 | 7/2004 | Waddell et al. | |
| 2005/0245534 A1 | 11/2005 | Link et al. | |
| 2005/0261302 A1 | 11/2005 | Hoff et al. | |
| 2005/0277647 A1 | 12/2005 | Link et al. | |
| 2005/0288338 A1 | 12/2005 | Yao et al. | |
| 2006/0004049 A1 | 1/2006 | Yao et al. | |
| 2006/0009471 A1 | 1/2006 | Yao et al. | |
| 2006/0009491 A1 | 1/2006 | Yao et al. | |
| 2006/0079506 A1 | 4/2006 | Linders et al. | |
| 2006/0089349 A1 | 4/2006 | Gundertofte et al. | |
| 2006/0094699 A1 | 5/2006 | Kampen et al. | |
| 2006/0100235 A1 | 5/2006 | Andersen et al. | |
| 2006/0106008 A1 | 5/2006 | Andersen et al. | |
| 2006/0106071 A1 | 5/2006 | Lin et al. | |
| 2006/0111348 A1 | 5/2006 | Kampen et al. | |
| 2006/0111366 A1 | 5/2006 | Andersen et al. | |
| 2006/0281773 A1 | 12/2006 | Patel et al. | |
| 2007/0161641 A1 | 7/2007 | Hendrix et al. | |
| 2008/0064693 A1 | 3/2008 | Jaroskova et al. | |

FOREIGN PATENT DOCUMENTS

| | | |
|---|---|---|
| EP | 215297 A2 | 3/1987 |
| EP | 336356 | 4/1989 |
| EP | 405537 | 6/1990 |
| EP | 564924 A2 | 10/1993 |
| EP | 697403 A1 | 2/1996 |
| EP | 1180513 A1 | 2/2002 |
| SU | 740752 | 9/1980 |
| SU | 803348 | 9/1981 |
| WO | 9113081 | 9/1991 |
| WO | 9214697 | 9/1992 |
| WO | 9428885 | 12/1994 |
| WO | 9500146 | 1/1995 |
| WO | 9902145 | 1/1999 |
| WO | 0129007 | 4/2001 |
| WO | WO-03059905 A1 | 7/2003 |
| WO | 200365983 | 8/2003 |
| WO | 2003075660 | 9/2003 |

(Continued)

OTHER PUBLICATIONS

Bernard Testa "Predicting drug metabolism: Concepts and challenges" Pure and Applied Chemistry 2004, vol. 76. No. 5, pp. 907-914.*

(Continued)

Primary Examiner—Shailendra Kumar
(74) Attorney, Agent, or Firm—Sreenivasarao Vepachedu

(57) ABSTRACT

The present invention relates to compounds which are inhibitors of the 11-beta-hydroxysteroid dehydrogenase Type 1 enzyme. The present invention further relates to the use of inhibitors of 11-beta-hydroxysteroid dehydrogenase Type 1 enzyme for the treatment of non-insulin dependent type 2 diabetes, insulin resistance, obesity, lipid disorders, metabolic syndrome and other diseases and conditions that are mediated by excessive glucocorticoid action.

35 Claims, No Drawings

FOREIGN PATENT DOCUMENTS

| | | |
|---|---|---|
| WO | 200411310 | 2/2004 |
| WO | 2004033427 | 4/2004 |
| WO | 2004037251 | 5/2004 |
| WO | 2004056744 | 7/2004 |
| WO | 2004056745 | 8/2004 |
| WO | 2004065351 | 8/2004 |
| WO | 2004089367 | 10/2004 |
| WO | 2004089380 | 10/2004 |
| WO | 2004089416 | 10/2004 |
| WO | 2004089470 | 10/2004 |
| WO | 2004089471 | 10/2004 |
| WO | 2004089896 | 10/2004 |
| WO | WO-2004113310 A1 | 12/2004 |
| WO | 2005016877 | 2/2005 |
| WO | 2005042513 | 5/2005 |
| WO | 2005046685 | 5/2005 |
| WO | 2005047250 | 5/2005 |
| WO | 2005060963 | 7/2005 |
| WO | 2005097764 | 10/2005 |
| WO | 2005103023 | 11/2005 |
| WO | 2005108359 | 11/2005 |
| WO | WO-2005108361 A1 | 11/2005 |
| WO | 2005116002 | 12/2005 |
| WO | 2006002349 | 1/2006 |
| WO | 2006002350 | 1/2006 |
| WO | 2006002361 | 1/2006 |
| WO | 2006012173 | 2/2006 |
| WO | 2006012226 | 2/2006 |
| WO | 2006012227 | 2/2006 |
| WO | 2006012642 | 2/2006 |
| WO | 2006017542 | 2/2006 |
| WO | 2006020598 | 2/2006 |
| WO | 2006024627 | 3/2006 |
| WO | 2006024628 | 3/2006 |
| WO | 2006040329 | 4/2006 |
| WO | 2006048330 | 5/2006 |
| WO | 2006048331 | 5/2006 |
| WO | 2006048750 | 5/2006 |
| WO | 2006049952 | 5/2006 |
| WO | 2006050908 | 5/2006 |
| WO | 2006053024 | 5/2006 |
| WO | 2006066109 | 6/2006 |
| WO | WO-2006104280 A1 | 10/2006 |

OTHER PUBLICATIONS

Albrecht S. et al., "Nonpituitary Tumors of the Sellar Region," Cushing's Disease in:Melmed S. Ed. The Pituitary, 2002, pp. 592-612, 2nd Ed.

Billaudel B., "Immediate in-vivo effect of corticosterone on glucose-induced insulin secretion in the rat," Journ of Endocrin, 1982, pp. 315-320, vol. 95.

Budziszewska., "Effect of antidepressant drugs on the hypothalamic-pituitary-adrenal axis activity and glucocorticoid receptor function," Polish Journal of Pharm, 2002, pp. 343-349, vol. 54.

Cooper M.S. et al., "Modulation of 11O-Hydroxysteroid Dehydrogenase Enzymes by Proinflammatory Cytokines in Osteoblasts: An Autocrine Switch from Glucocorticoid Inactivation to Activation," J Bone Miner Res, 2001, pp. 1037-1044, vol. 16.

De Battista et al., "The use of mifepristone in the treatment of neuropsychiatric disorders," Trends in Endoc. Metab, 2006, pp. 117-120, vol. 17.

Gomez Sanchez et al., "Central hypertensinogenic effects of glycyrrhizic acid and carbenoxolone," AJP Endocrinology and Metabolism, 2006, pp. E1125-E1130, vol. 263 (6).

Harris, H.J. et al., "Intracellular regeneration of glucocorticoids by 11beta-hydroxysteroid dehydrogenase (11beta-HSD)-1 plays a key role in regulation of the hypothalamic-pituitary-adrenal axis: analysis of 11beta-HSD-1-deficient mice," Endocrinology, 2001, pp. 114-120, 142 (1).

Hong et al., "Synthesis and biological studies of novel neurotensin (8-13) mimetics," Bioorganic & Medicinal Chemistry, 2002, pp. 3849-3858, vol. 10 (12).

International Search Report for application No. PCT/US2006/000210, Mailed on Aug. 11, 2006, 5 pages.

International Search Report for application No. PCT/US2006/000402, Mailed on Sep. 11, 2006, 6 pages.

International Search Report for application no. PCT/US2007/066125, Mailed on Sep. 21, 2007, 5 pages.

International Search Report for application No. PCT/US2008/073830, Mailed on Mar. 12, 2009, 5 pages.

Kerr D.S., "Modulation of hippocampal long-term potentiation and long-term depression by corticosteroid receptor activation," Psychobiology, 1994, pp. 123-133, vol. 22.

Kershaw E.E., "Adipocyte-Specific Glucocorticoid Inactivation Protects Against Diet-Induced Obesity," Diabetes, 2005, pp. 1023-1031, vol. 54.

Kim C. H. et al., "Effects of dexamethasone on proliferation, activity, and cytkine secretion of normal human bone marrow stromal cells: possible mechanisms of glucocorticoidinduced bone loss," Journ of Endocrin, 1999, pp. 371-379, vol. 162.

Kolocouris N. et al., "Synthesis and antiviral activity evaluation of some new aminoadamantane derivatives," Journal of Medicinal Chemistry, 1996, pp. 3307-3318, vol. 39 (17).

Kozlowski J.A. et al., "Substituted 2-0-Methyl Piperazines as Muscarinic M2 Selective Ligands," Bioorg & Medicin Chem Ltrs, 2002, pp. 791-794, vol. 12.

Lakshmi et al., "Regional Distribution of 11-beta-Hydroxysteroid Dehydrogenase in Rat Brain," Endocrinology, 1991, 128 (4), 1741-1748.

Landfield.,"Hippocampal Cell Death," Science, 1996, vol. 272, pp. 1249-1251.

Le Noble W.J. et al., "5-tert-Butyladamantan-2-one," J Org Chem, 1983, pp. 1099-1101, vol. 48.

Mcewen., "Glucocorticoids, depression, and mood disorders: structural remodeling in the brain," Metab. Clin. And Exp, 2005, vol. 54,pp. 20-23.

Moisan et al., "11-beta-Hydroxysteroid Dehydrogenase Bioactivity and Messenger RNA Expression in Rat Forebrain: Localization in Hypothalamus, Hippocampus, and Cortex," Endocrinology, 1990, 127 (3), 1450-1455.

Monder et al., Vitamins and Hormones, 1983, pp. 187-271, vol. 47.

Nagasawa et al., Journal of Medicinal Chemistry, 1975, pp. 826-830, vol. 18 (8).

Norman et al., "Emerging treatments for major depression," Expert Rev. Neurotherapeutics, 2007, vol. 7, pp. 203-213.

Ortsater H. et al., "Regulation of 11β-hydroxyteroid dehydrogenase type 1 and glucose-stimulated insulin secretion in pancreatic islets of Langerhans," Diabetes Metab. Res. Rev, 2005, pp. 359-366.

Parks W. G., "Gordon Research Conferences: Program for 1966," Science, 1966, pp. 1249-1251, vol. 272.

Pirkle et al., "Use of intercalative effects to enhance enantioselectivity chiral stationary phase design," Journal of Chromatography, 1993, pp. 11-19, vol. 641.

Rajan et al., "11 beta-Hydroxysteroid dehydrogenase in cultured hippocampal cells reactivates inert 11-dehydrocorticosterone, potentiating neurotoxicity," Journal of Neuroscience, 1996, pp. 65-70, vol. 16.

Ringman J., "What the Study of Persons at Risk for Familial Alzheimer's Disease Can Tell Us about the Earliest Stages of the disorder," J Geriatr Psychiatry Neurology, 2005, pp. 228-233.

Sakai R. R. et al.,"Immunocytochemical Localization of 11 Beta-Hydroxysteroid Dehydrogenase in Hippocampus and Other Brain Regions of the Rat," J Neuroendocrinol, 1992, 101-106, vol. 4.

Schteingart D.E., "Cushing Syndrome," Princ. & Prac. Of Endoc. & Metab, 2001, pp. 723-728, Chap. 75.

Seckl et al., "The 11-beta hydroxysteroid dehydrogenase inhibitor glycyrrhetinic acid affects corticosteroid feedback regulation of hypothalamic corticotrophin-releasing peptides in rats," Journal of Endocrinology, 1993, pp. 471-477, vol. 136.

Small G.R. et al., "Preventing local regeneration of glucocorticoids by 11β-hydroxysteroid dehydrogenase type 1 enhances angiogenesis," Proc. Natl. Acad. Sci, 2005, pp. 12165-12170.

Strohle et al.,"Stress Responsive Neurohormones in Depression and Anxiety," Pharmacopsychiatry, 2003, vol. 36, pp. S207-S214.

Tadayyon M., "Insulin sensitization in the treatment of Type 2 diabetes," Expert Opin Investig Drugs, 2003, pp. 307-324, vol. 12 (3).

Vaidyanathan ., "Decarboxylation of 1-Aminocyclopropanecarboxylic Acid and Its Derivatives," J Org Chem, 1989, pp. 1810-1815, vol. 54.

Wooley C.S. et al., "Exposure to excess glucocorticoids alters dendritic morphology of adult hippocampal pyramidal neurons," Brain Res, 1990, pp. 225-331, vol. 531.

Yau Jel W., "Glucocorticoids, Hippocampal Corticosteroid Receptor Gene Expression and Antidepressant Treatment: Relationship with Spatial learning in Young and Aged Rats," Neuroscience, 1995, pp. 571-581, vol. 66 (3).

Yeh et al., "Discovery of orally active butyrolactam Ilbeta-HSD1 inhibitors," Bioorganic & Medicinal Chemistry Letters, Oxford, GB, 2006, pp. 5555-5560, vol. 16 (21).

Yeh Vince S.C. et al., "A highly efficient synthesis of potent and selective butyrolactam inhibitors of Ilbeta-HSD1," Organic Letters, 2006, pp. 3963-3966, vol. 8 (18).

Ziegler Fee., "Substitution Reactions of Specifically ortho-Metalated Piperonal Cyclohexylimine," J Org Chem, 1976, pp. 1564-1566, vol. 41 (9).

Seckl J.R et al, Endocrinology *Minireview: 11β-Hydroxysteroid Dehydrogenase Type 1- A Tissue-Specific Amplifier of Glucocorticoid Action* 142: 1371-1376 (2001).

Higuchi, T and Stella V. Pro-drugs as Novel Delivery Systems vol. 14. Roche E, Bioreversible Carriers in Drug Design APA and Pergamon Press (1987).

Jones C.D et al Journal Org. Chem. *Effects of Substituent Modification on Face Selection in Reduction* 63: 2758-2760 (1998).

Greene T.W, P.G.M Wuts "Protective Groups in Organic Synthesis" $3^{rd}$ ed. (1999).

Han et al, J. Am. Chem. Soc. *Properly Designed Modular Asymmetric Synthesis for Enantiopure Sulfinamise Auxiliaries from N-Sulfonyl 1,2,3-oxathiazolidine-2-oxide Agents* 124 :7880-7881 (2002).

Walker B.R et al. Journal of Clin. Endocrinology and Met. Carbenoxolone increases Hepatic insulin Sensitivity in Man: A Novel Role for 11-0xosteroid Reductase in Enhancing Glucocorticoid Receptor Activation 80 3155-3159 (1995).

Billaudel et al, Horm. Metab. Res. Direct Effect of Corticosterone upon Insulin Secretion Studied by Three Different Techniques 11: 555-560 (1979).

Davani et al, Journal of Biol. Chem. Type 1 11β-Hydroxysteroid Dehydrogenase Mediates Glucocorticoid Activation and Insulin Release in Pancreatic Islets 275: 34841-34844 (2000).

Paterson J.M et al Proc. Natl. Acad. Sci. USA Metabolic Syndrome without Obesity: Hepatic Overexpression of 11 {beta}-hydroxysteroid dehydrogenase type 1 in Transgenic Mice 101: 7088-7093 (2004).

Montague et al, Diabetes, Causes and Consequences of Visceral Adiposity 49: 883-888 (2000).

Orstater et al, Diabetes Metab. Res. Rev. Regulation of 11β-hydroxysteroid dehydrogenase Type 1 and Glucose-stimulated Insulin Secretion in Pancreatic Islets of Langerhans 21: 359-366 (2005).

Masuzaki et al, Science A Transgenic Model of Visceral Obesity and the Metabolic Syndrome 294: 2166-2170 (2001).

Walker, B.R., Clinical Science Corticosteroids and Vascular Tone: Mapping the Messenger Maze 82: 597-605 (1992).

Pirpiris M., Hypertension Pressor Responsiveness in Corticosteroid-Induced Hypertension in Humans 19: 567-574 (1992).

Masuzaki et al, Journal of Clin Invest. Transgenic Amplification of Glucocorticoid Action in Adipose Tissue Causes High Blood Pressure in Mice 112(1): 83-90 (2003).

Rook, G.A.W., Baillleres Clinical Endocrinology. and Metabolism Glucocorticoids and Immune Function 13(4): 567-581 (1999).

Belanoff, J.K., Journal of Psychiatric Research Corticosteroids and Cognition 35: 127-145 (2001).

Baxter, J.D., Pharm. Ther Glucoccorticoid Hormone Action 2: 605-659 (1976).

Bertagna, X, Pituitary Tumors Cushing's Disease Chapter 13 Section 3: 592-612 (2002).

Walker, et al, PNAS Preventing local regeneration of glucocorticoids by 11_-hydroxysteroid dehydrogenase type 1 enhances angiogenesis 102: 12165-12170 (2005).

Hodge, G., Experimental Physiology Salr-Sensitive Hypertension Resulting from Nitric Oxide Synthase Inhibition is associated with Loss of Regulation of Angiotensin II 87(1): 1-8 (2002).

Good man and Gilman's, The Pharmacological Basis of Therapeutics, seventh Edition MacMillan Publishing Company New York, NY (1985).

Issa, A.M., The Journal of Neuroscience Hypothalamic-Pituitary-Adrenal Activivty in Aged, Cognitively Impaired and Cognitively Unimpaired Rats 10(10): 3247-3254 (1990).

Boscaro, M., The Lancet Cushing's Syndrome 357: 783-791 (2001).

Orth, D., The New England Journal of Medicine Normal Hypothalamic-Pituitary-Adrenal Physiology 332 (12): 791-803 (1995).

Cooper., M.S., Bone Expression and Functional Consequences of 11β-Hydroxysteroid Dehydrogenase Activity in Human Bone 27(3): 375-381 (2000).

Bellows et al., Bone Osteoprogenitor Cells in Cell Populations Derived From Mouse and Rat Calvaria Differ in Their Response to Corticosterone, Cortisol and Cortisone 23(2): 119-125 (1998).

Bland, R., Journal of Endocrinology Characterization of 11β-Hydroxysteroid Dehydrogenase Activityand Corticosteroid Receptor Expression in Human Osteosarcoma Cell Lines 161: 455-464 (1999).

Rauz, S., Q. J. Med Inhibition if 11β-Hydroxysteroid Dehydrogenase type 1 lower Intraocular Pressure in Patients with Ocular Hypertension 96: 481-490 (2003).

Tronche, F Nature Genetics Disruption of the glucocorticoid receptor gene in the nervous system results in reduced anxiety 23: 99-103 (1999).

Lupien, S., Nature Cortisol Levels during Human aging Predict Hippocampal Atrophy and memory deficits 1(1): 69-103 ( 1998).

Rauz, S., Invest Ophthalmology & Vis. Science Expression and Putative Role of 11β-Hydroxysteroid Dehydrogenase Isozymes with in the Human Eye 42(9): 2037-2042 (2001).

Wolkowitz, O.M., Annals New York Academy of Sciences The Steroid Dementia Syndrome: An Unrecognized Complication of Glucocorticoid Treatment 1032: 191-194 (2004).

Lane, N., Med Pediatr Oncol. Effect of Glucocorticoids on Bone Density41: 212-216 (2003).

Morton, N. M., The Journal of Biological Chem. Improved Lipid and Lipoprotein Profile, Hepatic insulin Sensitivity, and Glucose Tolerance in 11β-Hydroxysteroid DehydrogenaseType 1 Null Mice 276(44) 41293-41300 (2001).

Hammami., M.M., Journal of Clin endocrinology Metab. Regulation of 11β-Hydroxysteroid Dehydrogenase Activity in Human SkinFibroblasts: enzymatic Modulation of Glucocorticoid Action 73: 326-334 (1991).

Mason, D., Immunology Today Genetic Variation in the Stress Response: Susceptibility to Experimaental Allergic Encephalomymyelitis and implications for Human Inflammatory Disease 12(2): 57-60 (1991).

Kornel, L., Steroids Mechanism of the Effects of Glucocorticoids and mineralocorticoids on Vascular Smooth Muscle Contractility 58: 580-587 (1993).

Becker, K., Prin. And Pract. of Endocrin. and Metabolism Cushing Syndrome 723-738.

Armaly et al., Arch Ophthal Dexamethasone Ocular Hypertension and Eosinopenia and Glucose Tolerance Test 78: 193-197 (1967).

Turner, R.T., Calcif . Tissue Int. Prednisone Inhibits Formation of Cortical Bone in Sham-Operated and Ovariectomized Female Rats 56: 311-315 (1995).

Cooper, M., Journal of Bone and Mineral Research Osteoblastic 11β-Hydroxysteroid DehydrogenaseTypr 1 Activity Increases with Age and Glucocorticoid Exposure 17: 979-986 (2002).

Sandeep, T., PNAS 11β-Hydroxysteroid Dehydrogenase Inhibition Improves Cognitive Function in Healthy Elderly Men and Type 2 Diabetes 101: 6734-6739 (2004).

Anstead, G., Advances in Would Care Steroids, Retinoids and Wound Healing 11: 277-285 (1998).

Beer, H. et al., Vitamins and Hormones Glucocorticoid-Regulated Gene Expression during Cutaneous Wound Repair 59: 217-239 (2000).

De Quervain, Human Mol. Genet Glucocorticoid-related genetic susceptibility for Alzheimer's Disease 13(1): 47-52 (2004).

Yau, J., Journal of Neuroscience Lack of tissue Glucocorticoid Reactivation in 11-beta-hydroxysteroid Dehydrogenase Type 1 Knockout MiceAmerliorates age-related learning Impairments 98: 4716-4721 (2001).

The Pitutiary, Shlomo Melmed: Second Edition, 2002.

* cited by examiner

INHIBITORS OF THE 11-BETA-HYDROXYSTEROID DEHYDROGENASE TYPE 1 ENZYME

This application is a continuation application of U.S. Non-Provisional patent application Ser. No. 11/325,965, filed Jan. 5, 2006, now U.S. Pat. No. 7,511,175, which claims priority from U.S. Provisional Patent Application Ser. No. 60/641,520, filed Jan. 5, 2005, which are incorporated herein by reference.

FIELD OF INVENTION

The present invention relates to compounds that are inhibitors of the 11-beta-hydroxysteroid dehydrogenase Type 1 enzyme. The present invention further relates to the use of inhibitors of 11-beta-hydroxysteroid dehydrogenase Type 1 enzyme for the treatment of non-insulin dependent type 2 diabetes, insulin resistance, obesity, lipid disorders, metabolic syndrome and other diseases and conditions that are mediated by excessive glucocorticoid action.

BACKGROUND OF THE INVENTION

Insulin is a hormone that modulates glucose and lipid metabolism. Impaired action of insulin (i.e., insulin resistance) results in reduced insulin-induced glucose uptake, oxidation and storage, reduced insulin-dependent suppression of fatty acid release from adipose tissue (i.e., lipolysis) and reduced insulin-mediated suppression of hepatic glucose production and secretion. Insulin resistance frequently occurs in diseases that lead to increased and premature morbidity and mortality.

Diabetes mellitus is characterized by an elevation of plasma glucose levels (hyperglycemia) in the fasting state or after administration of glucose during a glucose tolerance test. While this disease may be caused by several underlying factors, it is generally grouped into two categories, Type 1 and Type 2 diabetes. Type 1 diabetes, also referred to as Insulin Dependent Diabetes Mellitus ("IDDM"), is caused by a reduction of production and secretion of insulin. In type 2 diabetes, also referred to as non-insulin dependent diabetes mellitus, or NIDDM, insulin resistance is a significant pathogenic factor in the development of hyperglycemia. Typically, the insulin levels in type 2 diabetes patients are elevated (i.e., hyperinsulinemia), but this compensatory increase is not sufficient to overcome the insulin resistance. Persistent or uncontrolled hyperglycemia in both type 1 and type 2 diabetes mellitus is associated with increased incidence of macrovascular and/or microvascular complications including atherosclerosis, coronary heart disease, peripheral vascular disease, stroke, nephropathy, neuropathy and retinopathy.

Insulin resistance, even in the absence of profound hyperglycemia, is a component of the metabolic syndrome. Recently, diagnostic criteria for metabolic syndrome have been established. To qualify a patient as having metabolic syndrome, three out of the five following criteria must be met: elevated blood pressure above 130/85 mmHg, fasting blood glucose above 110 mg/dl, abdominal obesity above 40" (men) or 35" (women) waist circumference and blood lipid changes as defined by an increase in triglycerides above 150 mg/dl or decreased HDL cholesterol below 40 mg/dl (men) or 50 mg/dl (women). It is currently estimated that 50 million adults, in the US alone, fulfill these criteria. That population, whether or not they develop overt diabetes mellitus, are at increased risk of developing the macrovascular and microvascular complications of type 2 diabetes listed above.

Available treatments for type 2 diabetes have recognized limitations. Diet and physical exercise can have profound beneficial effects in type 2 diabetes patients, but compliance is poor. Even in patients having good compliance, other forms of therapy may be required to further improve glucose and lipid metabolism.

One therapeutic strategy is to increase insulin levels to overcome insulin resistance. This may be achieved through direct injection of insulin or through stimulation of the endogenous insulin secretion in pancreatic beta cells. Sulfonylureas (e.g., tolbutamide and glipizide) or meglitinide are examples of drugs that stimulate insulin secretion (i.e., insulin secretagogues) thereby increasing circulating insulin concentrations high enough to stimulate insulin-resistant tissue. However, insulin and insulin secretagogues may lead to dangerously low glucose concentrations (i.e., hypoglycemia). In addition, insulin secretagogues frequently lose therapeutic potency over time.

Two biguanides, metformin and phenformin, may improve insulin sensitivity and glucose metabolism in diabetic patients. However, the mechanism of action is not well understood. Both compounds may lead to lactic acidosis and gastrointestinal side effects (e.g., nausea or diarrhea).

Alpha-glucosidase inhibitors (e.g., acarbose) may delay carbohydrate absorption from the gut after meals, which may in turn lower blood glucose levels, particularly in the postprandial period. Like biguanides, these compounds may also cause gastrointestinal side effects.

Glitazones (i.e., 5-benzylthiazolidine-2,4-diones) are a newer class of compounds used in the treatment of type 2 diabetes. These agents may reduce insulin resistance in multiple tissues, thus lowering blood glucose. The risk of hypoglycemia may also be avoided. Glitazones modify the activity of the Peroxisome Proliferator Activated Receptor ("PPAR") gamma subtype. PPAR is currently believed to be the primary therapeutic target for the main mechanism of action for the beneficial effects of these compounds. Other modulators of the PPAR family of proteins are currently in development for the treatment of type 2 diabetes and/or dyslipidemia. Marketed glitazones suffer from side effects including bodyweight gain and peripheral edema.

Additional treatments to normalize blood glucose levels in patients with diabetes mellitus are needed. Other therapeutic strategies are being explored. For example, research is being conducted concerning Glucagon-Like Peptide 1 ("GLP-1") analogues and inhibitors of Dipeptidyl Peptidase IV ("DPP-IV") that increase insulin secretion. Other examples include: Inhibitors of key enzymes involved in the hepatic glucose production and secretion (e.g., fructose-1,6-bisphosphatase inhibitors) and direct modulation of enzymes involved in insulin signaling (e.g., Protein Tyrosine Phosphatase-1B, or "PTP-1B").

Another method of treating or prophylactically treating diabetes mellitus includes using inhibitors of 11-β-hydroxysteroid dehydrogenase Type 1 (11β-HSD1). Such methods are discussed in J. R. Seckl et al., Endocrinology, 142: 1371-1376, 2001 and references cited therein. Glucocorticoids are steroid hormones that are potent regulators of glucose and lipid metabolism. Excessive glucocorticoid action may lead to insulin resistance, type 2 diabetes, dyslipidemia, increased abdominal obesity and hypertension. Glucocorticoids circulate in the blood in an active form (i.e., cortisol in humans) and an inactive form (i.e., cortisone in humans). 11β-HSD1, which is highly expressed in liver and adipose tissue, converts cortisone to cortisol leading to higher local concentration of cortisol. Inhibition of 11β-HSD1 prevents or decreases the tissue specific amplification of glucocorticoid action thus imparting beneficial effects on blood pressure and glucose- and lipid-metabolism.

Thus, inhibiting 11β-HSD1 benefits patients suffering from non-insulin dependent type 2 diabetes, insulin resistance, obesity, lipid disorders, metabolic syndrome and other diseases and conditions mediated by excessive glucocorticoid action.

SUMMARY OF THE INVENTION

All patents, patent applications and literature references cited in the specification are herein incorporated by reference in their entirety.

One aspect of the present invention is directed toward a compound of formula (I)

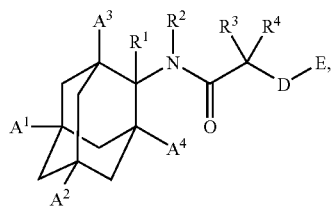

wherein $A^1$, $A^2$, $A^3$ and $A^4$ are each individually selected from the group consisting of hydrogen, alkenyl, alkyl, alkyl-NH-alkyl, alkylcarbonyl, alkylsulfonyl, carboxyalkyl, carboxycycloalkyl, cyano, cycloalkyl, cycloalkylcarbonyl, cycloalkylsulfonyl, aryl, arylalkyl, aryloxyalkyl, arylcarbonyl, arylsulfonyl, heteroaryl, heteroarylalkyl, heteroaryloxyalkyl, heteroarylsulfonyl, heterocycle, heterocyclealkyl, heterocycleoxyalkyl, heterocyclesulfonyl, halogen, haloalkyl, $-NR^5-[C(R^6R^7)]_n-C(O)-R^8$, $-O-[C(R^9R^{10})]_p-C(O)-R^{11}$, $-OR^{12}$, $-S$-alkyl, $-S(O)$-alkyl, $-N(R^{13}R^{14})$, $-CO_2R^{15}$, $-C(O)-N(R^{16}R^{17})$, $-C(R^{18}R^{19})-OR^{20}$, $-C(R^{21}R^{22})-N(R^{23}R^{24})$, $-C(=NOH)-N(H)_2$, $-C(R^{18a}R^{19a})-C(O)N(R^{23}R^{24})$, $-S(O)_2-N(R^{25}R^{26})$, and $-C(R^{18a}R^{19a})-S(O)_2-N(R^{25}R^{26})$;

$R^{18a}$ and $R^{19a}$ are each independently selected from the group consisting of hydrogen and alkyl;

n is 0 or 1;

p is 0 or 1;

D is a member selected from the group consisting of a $-O-$, $-S-$, $-S(O)-$ and $-S(O)_2-$;

E is a member selected from the group consisting of alkyl, alkoxyalkyl, carboxyalkyl, carboxycycloalkyl, cycloalkyl, cycloalkylalkyl, aryl, arylalkyl, haloalkyl, heteroaryl, heteroarylalkyl, heterocycle, heterocyclealkyl, or $R^4$ and E taken together with the atoms to which they are attached form a heterocycle;

$R^1$ is a member selected from the group consisting of hydrogen and alkyl;

$R^2$ is a member selected from the group consisting of hydrogen, alkyl and cycloalkyl;

$R^3$ and $R^4$ are each independently selected from the group consisting of hydrogen, alkyl, carboxyalkyl, carboxycycloalkyl, cycloalkyl, haloalkyl, aryl, arylalkyl, heteroaryl, heteroarylalkyl, heterocycle and heterocyclealkyl, or $R^3$ and $R^4$ taken together with the atoms to which they are attached form a ring selected from the group consisting of cycloalkyl and heterocycle;

$R^5$ is a member selected from the group consisting of hydrogen, alkyl, carboxyalkyl, cycloalkyl, carboxycycloalkyl, aryl, arylalkyl, aryloxyalkyl, hydroxy, alkoxy, heteroaryl, heteroarylalkyl, heteroaryloxyalkyl, heterocycle, heterocyclealkyl and heterocycleoxyalkyl;

$R^6$ and $R^7$ are each independently selected from the group consisting of hydrogen and alkyl, or $R^6$ and $R^7$ taken together with the atom to which they are attached form a ring selected from the group consisting of cycloalkyl and heterocycle;

$R^8$ is selected from the group consisting of hydrogen, alkyl, carboxy, carboxyalkyl, cycloalkyl, carboxycycloalkyl, aryl, arylalkyl, aryloxy, aryloxyalkyl, hydroxy, alkoxy, cycloalkyloxy, heteroaryl, heteroarylalkyl, heteroaryloxy, heteroaryloxyalkyl, heterocycle, heterocyclealkyl, heterocycleoxy, heterocycleoxyalkyl and $-N(R^{27}R^{28})$;

$R^9$ and $R^{10}$ are each independently selected from the group consisting of hydrogen and alkyl, or $R^9$ and $R^{10}$ taken together with the atom to which they are attached form a ring selected from the group consisting of cycloalkyl and heterocycle;

$R^{11}$ is selected from the group consisting of hydroxy and $-N(R^{29}R^{30})$;

$R^{12}$ is selected from the group consisting of hydrogen, alkyl, carboxyalkyl, cycloalkyl, carboxycycloalkyl, aryl, arylalkyl, aryloxyalkyl, haloalkyl, heteroaryl, heteroarylalkyl, heteroaryloxyalkyl, heterocycle, heterocyclealkyl and heterocycleoxyalkyl;

$R^{13}$ and $R^{14}$ are each independently selected from the group consisting of hydrogen, alkyl, alkylsulfonyl, aryl, arylalkyl, aryloxyalkyl, arylsulfonyl, carboxyalkyl, cycloalkyl, carboxycycloalkyl, cycloalkylsulfonyl, heteroaryl, heteroarylalkyl, heteroaryloxyalkyl, heteroarylsulfonyl, heterocycle, heterocyclealkyl, heterocycleoxyalkyl and heterocyclesulfonyl;

$R^{15}$ is selected from the group consisting of hydrogen, alkyl, carboxyalkyl, cycloalkyl, carboxycycloalkyl, aryl, arylalkyl, aryloxyalkyl, heteroaryl, heteroarylalkyl, heteroaryloxyalkyl, heterocycle, heterocyclealkyl and heterocycleoxyalkyl;

$R^{16}$ and $R^{17}$ are each independently selected from the group consisting of hydrogen, alkyl, alkoxy, alkylsulfonyl, aryl, arylalkyl, aryloxy, aryloxyalkyl, arylsulfonyl, carboxy, carboxyalkyl, carboxycycloalkyl, cycloalkyl, cycloalkyloxy, cycloalkylsulfonyl, heteroaryl, heteroarylalkyl, heteroaryloxyalkyl, heteroaryloxy, heteroarylsulfonyl, heterocycle, heterocyclealkyl, heterocycleoxyalkyl, heterocycleoxy, heterocyclesulfonyl, hydroxy, and -alkyl-$C(O)N(R^{201}R^{202})$, or, $R^{16}$ and $R^{17}$ taken together with the atom to which they are attached form a heterocycle;

$R^{201}$ and $R^{202}$ are independently selected from the group consisting of hydrogen and alkyl;

$R^{18}$, $R^{19}$ and $R^{20}$ are each independently selected from the group consisting of hydrogen, alkyl, aryl, arylalkyl, carboxyalkyl, carboxycycloalkyl, cycloalkyl, haloalkyl, heteroaryl, heteroarylalkyl, heterocycle and heterocyclealkyl;

$R^{21}$ and $R^{22}$ are each independently selected from the group consisting of hydrogen, alkyl, alkylcarbonyl, alkylsulfonyl, aryl, arylcarbonyl, arylsulfonyl, cycloalkyl, carboxyalkyl, carboxycycloalkyl, cycloalkylcarbonyl, cycloalkylsulfonyl, heteroaryl, heteroarylcarbonyl, heteroarylsulfonyl, heterocycle, heterocyclecarbonyl and heterocyclesulfonyl;

$R^{23}$ and $R^{24}$ are each independently selected from the group consisting of hydrogen, alkyl, alkylcarbonyl, alkoxy, alkylsulfonyl, aryl, arylcarbonyl, aryloxy, arylsulfonyl, carboxyalkyl, carboxycycloalkyl, cycloalkyl, cycloalkylcarbonyl, cycloalkyloxy, cycloalkylsulfonyl, heteroaryl, heteroarylcarbonyl, heteroaryloxy, heteroarylsulfonyl, heterocycle, heterocyclecarbonyl, heterocycleoxy, heterocyclesulfonyl and hydroxy, or, $R^{23}$ and $R^{24}$ taken together with the atom to which they are attached form a ring selected from the group consisting of heteroaryl and heterocycle;

$R^{25}$ and $R^{26}$ are each independently selected from the group consisting of hydrogen, alkyl, alkoxy, alkylsulfonyl, aryl, arylalkyl, aryloxy, aryloxyalkyl, arylsulfonyl, carboxy, carboxyalkyl, carboxycycloalkyl, cycloalkyl, cycloalkyloxy, cycloalkylsulfonyl, heteroaryl, heteroarylalkyl, heteroaryloxyalkyl, heteroaryloxy, heteroarylsulfonyl, heterocycle, heterocyclealkyl, heterocycleoxyalkyl, heterocycleoxy, heterocyclesulfonyl, and hydroxy, or, $R^{25}$ and $R^{26}$ taken together with the atom to which they are attached form a heterocycle;

$R^{27}$ and $R^{28}$ are each independently selected from the group consisting of hydrogen, alkyl, alkoxy, alkylsulfonyl, aryl, arylalkyl, aryloxy, aryloxyalkyl, arylsulfonyl, carboxy, carboxyalkyl, cycloalkyl, cycloalkyloxy, carboxycycloalkyl, cycloalkylsulfonyl, heteroaryl, heteroarylalkyl, heteroaryloxy, heteroaryloxyalkyl, heteroarylsulfonyl, heterocycle, heterocyclealkyl, heterocycleoxy, heterocycleoxyalkyl, heterocyclesulfonyl and hydroxy, or, $R^{27}$ and $R^{28}$ taken together with the atom to which they are attached form a heterocycle; and $R^{29}$ and $R^{30}$ are each independently selected from the group consisting of hydrogen, alkyl, alkoxy, alkylsulfonyl, aryl, arylalkyl, aryloxy, aryloxyalkyl, arylsulfonyl, carboxy, carboxyalkyl, cycloalkyl, cycloalkyloxy, carboxycycloalkyl, cycloalkylsulfonyl, heteroaryl, heteroarylalkyl, heteroaryloxy, heteroaryloxyalkyl, heteroarylsulfonyl, heterocycle, heterocyclealkyl, heterocycleoxy, heterocycleoxyalkyl, heterocyclesulfonyl, and hydroxy, or, $R^{29}$ and $R^{30}$ taken together with the atom to which they are attached form a heterocycle;

provided that, if $R^1$ is hydrogen; then at least one of $A^1$, $A^2$, $A^3$ and $A^4$ is not hydrogen.

A further aspect of the present invention encompasses the use of the compounds of formula (I) for the treatment of disorders that are mediated by 11-beta-hydroxysteroid dehydrogenase Type 1 enzyme, such as non-insulin dependent type 2 diabetes, insulin resistance, obesity, lipid disorders, metabolic syndrome and other diseases and conditions that are mediated by excessive glucocorticoid action, comprising administering a therapeutically effective amount of a compound of formula (I).

According to still another aspect, the present invention is directed to a pharmaceutical composition comprising a therapeutically effective amount of a compound of formula (I) in combination with a pharmaceutically suitable carrier.

DETAILED DESCRIPTION OF THE INVENTION

All patents, patent applications and literature references cited in the specification are herein incorporated by reference in their entirety.

One aspect of the present invention is directed toward a compound of formula (I), wherein $A^2$, $A^3$ and $A^4$ are hydrogen;

$R^1$ and $R^2$ are hydrogen; and $A^1$, $R^3$, $R^4$, D and E are as described in the summary of the invention.

Another aspect of the present invention is directed toward a compound of formula (I), wherein $A^2$, $A^3$ and $A^4$ are hydrogen;

$R^1$ and $R^2$ are hydrogen;

$R^3$ and $R^4$ are hydrogen; and $A^1$, D and E are as described in the summary of the invention.

Another aspect of the present invention is directed toward a compound of formula (I), wherein $A^2$, $A^3$ and $A^4$ are hydrogen;

$R^1$ and $R^2$ are hydrogen;

$R^3$ and $R^4$ are hydrogen;

D is —O—; and $A^1$ and E are as described in the summary of the invention.

Another aspect of the present invention is directed toward a compound of formula (I), wherein $A^2$, $A^3$ and $A^4$ are hydrogen;

$R^1$ and $R^2$ are hydrogen;

$R^3$ and $R^4$ are hydrogen;

D is —O—;

E is as described in the summary of the invention; and $A^1$ is selected from the group consisting of $A^1$ is selected from the group consisting of alkenyl, alkylsulfonyl, cyano, heteroaryl, heteroarylalkyl, —$OR^{12}$, carboxyalkyl, —S-alkyl, —S(O)-alkyl, —$C(R^{18}R^{19})$—$OR^{20}$, —C(O)—N$(R^{16}R^{17})$, —$C(R^{18a}R^{19a})$—C(O)N$(R^{23}R^{24})$, —C(=NOH)—N(H)$_2$, —S(O)$_2$—N$(R^{25}R^{26})$, —CO$_2R^{15}$, —$C(R^{18a}R^{19a})$—S(O)$_2$—N$(R^{25}R^{26})$, and —$C(R^{21}R^{22})$—N$(R^{23}R^{24})$ wherein $R^{12}$, $R^{15}$, $R^{16}$, $R^{17}$, $R^{18}$, $R^{19}$, $R^{18a}$, $R^{19a}$, $R^{21}$, $R^{22}$, $R^{23}$, $R^{24}R^{25}$, and $R^{26}$ are as described in the summary of the invention.

Another aspect of the present invention is directed toward a compound of formula (I), wherein $A^2$, $A^3$ and $A^4$ are hydrogen;

$R^1$ and $R^2$ are hydrogen;

$R^3$ and $R^4$ are hydrogen;

D is —O—;

$A^1$ is selected from the group consisting of alkenyl, alkylsulfonyl, cyano, heteroaryl, heteroarylalkyl, —$OR^{12}$, carboxyalkyl, —S-alkyl, —S(O)-alkyl, —$C(R^{18}R^{19})$—$OR^{20}$, —C(O)—N$(R^{16}R^{17})$, —$C(R^{18a}R^{19a})$—C(O)N$(R^{23}R^{24})$, —C(=NOH)—N(H)$_2$, —S(O)$_2$—N$(R^{25}R^{26})$, —CO$_2R^{15}$, —$C(R^{18a}R^{19a})$—S(O)$_2$—N$(R^{25}R^{26})$, and —$C(R^{21}R^{22})$—N$(R^{23}R^{24})$ wherein $R^{12}$, $R^{15}$, $R^{16}$, $R^{17}$, $R^{18}$, $R^{19}$, $R^{18a}$, $R^{19a}$, $R^{21}$, $R^{22}$, $R^{23}$, $R^{24}$, $R^{25}$, and $R^{26}$ are as described in the summary of the invention; and E is selected from the group consisting of aryl, cycloalkyl, heteroaryl, heterocycle, arylalkyl and cycloalkylalkyl.

Another aspect of the present invention is directed toward a compound of formula (I), wherein $A^2$, $A^3$ and $A^4$ are hydrogen;

$R^1$ and $R^2$ are hydrogen;

$R^3$ is hydrogen;

$R^4$ is alkyl; and $A^1$, D and E are as described in the summary of the invention.

Another aspect of the present invention is directed toward a compound of formula (I), wherein $A^2$, $A^3$ and $A^4$ are hydrogen;

$R^1$ and $R^2$ are hydrogen;

$R^3$ is hydrogen;

$R^4$ is alkyl;

D is —O—; and $A^1$ and E are as described in the summary of the invention.

Another aspect of the present invention is directed toward a compound of formula (I), wherein $A^2$, $A^3$ and $A^4$ are hydrogen;

$R^1$ and $R^2$ are hydrogen;

$R^3$ is hydrogen;

$R^4$ is alkyl;

D is —O—;

E is as described in the summary of the invention; and $A^1$ is selected from the group consisting of alkenyl, alkylsulfonyl, cyano, heteroaryl, heteroarylalkyl, —$OR^{12}$, carboxyalkyl, —S-alkyl, —S(O)-alkyl, —$C(R^{18}R^{19})$—$OR^{20}$, —C(O)—N$(R^{16}R^{17})$, —$C(R^{18a}R^{19a})$—C(O)N$(R^{23}R^{24})$, —C(=NOH)—N(H)$_2$, —S(O)$_2$—N$(R^{25}R^{26})$, —CO$_2R^{15}$, —$C(R^{18a}R^{19a})$—S(O)$_2$—N$(R^{25}R^{26})$, and —$C(R^{21}R^{22})$—N ($R^{23}R^{24}$) wherein $R^{12}$, $R^{15}$, $R^{16}$, $R^{17}$, $R^{18}$, $R^{19}$, $R^{18a}$, $R^{19a}$, $R^{21}$, $R^{22}$, $R^{23}$, $R^{24}$, $R^{25}$, and $R^{26}$ are as described in the summary of the invention.

Another aspect of the present invention is directed toward a compound of formula (I), wherein $A^2$, $A^1$ and $A^4$ are hydrogen;
$R^1$ and $R^2$ are hydrogen;
$R^3$ is hydrogen;
$R^4$ is alkyl;
D is —O—;
$A^1$ is selected from the group consisting of alkenyl, alkylsulfonyl, cyano, heteroaryl, heteroarylalkyl, —$OR^{12}$, carboxyalkyl, —S-alkyl, —S(O)-alkyl, —C($R^{18}R^{19}$)—$OR^{20}$, —C(O)—N($R^{16}R^{17}$), —C($R^{18a}R^{19a}$)—C(O)N($R^{23}R^{24}$), —C(=NOH)—N(H)$_2$, —S(O)$_2$—N($R^{25}R^{26}$), —CO$_2R^{15}$, —C($R^{18a}R^{19a}$)—S(O)$_2$—N($R^{25}R^{26}$), and —C($R^{21}R^{22}$)—N($R^{23}R^{24}$) wherein $R^{12}$, $R^{15}$, $R^{16}$, $R^{17}$, $R^{18}$, $R^{19}$, $R^{18a}$, $R^{19a}$, $R^{21}$, $R^{22}$, $R^{23}$, $R^{24}$, $R^{25}$, and $R^{26}$ are as described in the summary of the invention; and E is selected from the group consisting of aryl, cycloalkyl, heteroaryl, heterocycle, arylalkyl and cycloalkylalkyl.

Another aspect of the present invention is directed toward a compound of formula (I), wherein $A^2$, $A^3$ and $A^4$ are hydrogen;
$R^1$ and $R^2$ are hydrogen;
$R^3$ and $R^4$ are alkyl; and $A^1$, D and E are as described in the summary of the invention.

Another aspect of the present invention is directed toward a compound of formula (I), wherein $A^2$, $A^3$ and $A^4$ are hydrogen;
$R^1$ and $R^2$ are hydrogen;
$R^3$ and $R^4$ are alkyl;
D is —O—; and $A^1$ and E are as described in the summary of the invention.

Another aspect of the present invention is directed toward a compound of formula (I), wherein $A^2$, $A^1$ and $A^4$ are hydrogen;
$R^1$ and $R^2$ are hydrogen;
$R^3$ and $R^4$ are alkyl;
D is —O—;
E is as described in the summary of the invention; and
$A^1$ is selected from the group consisting of alkenyl, alkylsulfonyl, cyano, heteroaryl, heteroarylalkyl, —$OR^{12}$, carboxyalkyl, —S-alkyl, —S(O)-alkyl, —C($R^{18}R^{19}$)—$OR^{20}$, —C(O)—N($R^{16}R^{17}$), —C($R^{18a}R^{19a}$)—C(O)N($R^{23}R^{24}$), —C(=NOH)—N(H)$_2$, —S(O)$_2$—N($R^{25}R^{26}$), —CO$_2R^{15}$, —C($R^{18a}R^{19a}$)—S(O)$_2$—N($R^{25}R^{26}$), and —C($R^{21}R^{22}$)—N($R^{23}R^{24}$) wherein $R^{12}$, $R^{15}$, $R^{16}$, $R^{17}$, $R^{18}$, $R^{19}$, $R^{18a}$, $R^{19a}$, $R^{21}$, $R^{22}$, $R^{23}$, $R^{24}$, $R^{25}$, and $R^{26}$ are as described in the summary of the invention.

Another aspect of the present invention is directed toward a compound of formula (I), wherein $A^2$, $A^3$ and $A^4$ are hydrogen;
$R^1$ and $R^2$ are hydrogen;
$R^3$ and $R^4$ are alkyl;
D is —O—;
$A^1$ is selected from the group consisting of alkenyl, alkylsulfonyl, cyano, heteroaryl, heteroarylalkyl, —$OR^{12}$, carboxyalkyl, —S-alkyl, —S(O)-alkyl, —C($R^{18}R^{19}$)—$OR^{20}$, —C(O)—N($R^{16}R^{17}$), —C($R^{18a}R^{19a}$)—C(O)N($R^{23}R^{24}$), —C(=NOH)—N(H)$_2$, —S(O)$_2$—N($R^{25}R^{26}$), —CO$_2R^{15}$, —C($R^{18a}R^{19a}$)—S(O)$_2$—N($R^{25}R^{26}$), and —C($R^{21}R^{22}$)—N($R^{23}R^{24}$) wherein $R^{12}$, $R^{15}$, $R^{16}$, $R^{17}$, $R^{18}$, $R^{19}$, $R^{18a}$, $R^{19a}$, $R^{21}$, $R^{22}$, $R^{23}$, $R^{24}$, $R^{25}$, and $R^{26}$ are as described in the summary of the invention; and E is selected from the group consisting of aryl, cycloalkyl, heteroaryl, heterocycle, arylalkyl and cycloalkylalkyl.

Another aspect of the present invention is directed toward a compound of formula (I), wherein $A^2$, $A^3$ and $A^4$ are hydrogen;
$R^1$ and $R^2$ are hydrogen;
$R^3$ and $R^4$ taken together with the atoms to which they are attached form a ring selected from the group consisting of cycloalkyl and heterocycle; and $A^1$, D and E are as described in the summary of the invention.

Another aspect of the present invention is directed toward a compound of formula (I), wherein $A^2$, $A^3$ and $A^4$ are hydrogen;
$R^1$ and $R^2$ are hydrogen;
$R^3$ and $R^4$ taken together with the atoms to which they are attached form a cycloalkyl ring; and $A^1$, D and E are as described in the summary of the invention.

Another aspect of the present invention is directed toward a compound of formula (I), wherein $A^2$, $A^3$ and $A^4$ are hydrogen;
$R^1$ and $R^2$ are hydrogen;
$R^3$ and $R^4$ taken together with the atoms to which they are attached form a cycloalkyl ring;
D is —O—; and $A^1$ and E are as described in the summary of the invention.

Another aspect of the present invention is directed toward a compound of formula (I), wherein $A^2$, $A^3$ and $A^4$ are hydrogen;
$R^1$ and $R^2$ are hydrogen;
$R^3$ and $R^4$ taken together with the atoms to which they are attached form a cycloalkyl ring;
D is —O—;
E is as described in the summary of the invention; and
$A^1$ is selected from the group consisting of alkenyl, alkylsulfonyl, cyano, heteroaryl, heteroarylalkyl, —$OR^{12}$, carboxyalkyl, —S-alkyl, —S(O)-alkyl, —C($R^{18}R^{19}$)—$OR^{20}$, —C(O)—N($R^{16}R^{17}$), —C($R^{18a}R^{19a}$)—C(O)N($R^{23}R^{24}$), —C(=NOH)—N(H)$_2$, —S(O)$_2$—N($R^{25}R^{26}$), —CO$_2R^{15}$, —C($R^{18a}R^{19a}$)—S(O)$_2$—N($R^{25}R^{26}$), and —C($R^{21}R^{22}$)—N($R^{23}R^{24}$) wherein $R^{12}$, $R^{15}$, $R^{16}$, $R^{17}$, $R^{18}$, $R^{19}$, $R^{18a}$, $R^{19a}$, $R^{21}$, $R^{22}$, $R^{23}$, $R^{24}$, $R^{25}$, and $R^{26}$ are as described in the summary of the invention.

Another aspect of the present invention is directed toward a compound of formula (I), wherein $A^2$, $A^3$ and $A^4$ are hydrogen;
$R^1$ and $R^2$ are hydrogen;
$R^3$ and $R^4$ taken together with the atoms to which they are attached form a cycloalkyl ring;
D is —O—;
$A^1$ is selected from the group consisting of alkenyl, alkylsulfonyl, cyano, heteroaryl, heteroarylalkyl, —$OR^{12}$, carboxyalkyl, —S-alkyl, —S(O)-alkyl, —C($R^{18}R^{19}$)—$OR^{20}$, —C(O)—N($R^{16}R^{17}$), —C($R^{18a}R^{19a}$)—C(O)N($R^{23}R^{24}$), —C(=NOH)—N(H)$_2$, —S(O)$_2$—N($R^{25}R^{26}$), —CO$_2R^{15}$, —C($R^{18a}R^{19a}$)—S(O)$_2$—N($R^{25}R^{26}$), and —C($R^{21}R^{22}$)—N($R^{23}R^{24}$) wherein $R^{12}$, $R^{15}$, $R^{16}$, $R^{17}$, $R^{18}$, $R^{19}$, $R^{18a}$, $R^{19a}$, $R^{21}$, $R^{22}$, $R^{23}$, $R^{24}$, $R^{25}$, and $R^{26}$ are as described in the summary of the invention; and E is selected from the group consisting of aryl, cycloalkyl, heteroaryl, heterocycle, arylalkyl and cycloalkylalkyl.

Another aspect of the present invention is directed toward a compound of formula (I), wherein $A^2$, $A^3$ and $A^4$ are hydrogen;
$R^1$ and $R^2$ are hydrogen;
$R^3$ and $R^4$ taken together with the atoms to which they are attached form a cyclopropyl ring;
D is —O—;
$A^1$ is selected from the group consisting of alkenyl, alkylsulfonyl, cyano, heteroaryl, heteroarylalkyl, —$OR^{12}$, carboxyalkyl, —S-alkyl, —S(O)-alkyl, —C($R^{18}R^{19}$)—$OR^{20}$, —C(O)—N($R^{16}R^{17}$), —C($R^{18a}R^{19a}$)—C(O)N($R^{23}R^{24}$), —C(=NOH)—N(H)$_2$, —S(O)$_2$—N($R^{25}R^{26}$), —CO$_2R^{15}$, —C($R^{18a}R^{19a}$)—S(O)$_2$—N($R^{25}R^{26}$), and —C($R^{21}R^{22}$)—N($R^{23}R^{24}$) wherein $R^{12}$, $R^{15}$, $R^{16}$, $R^{17}$, $R^{18}$, $R^{19}$, $R^{18a}$, $R^{19a}$, $R^{21}$, $R^{22}$, $R^{23}$, $R^{24}$, $R^{25}$, and $R^{26}$ are as described in the summary of the invention; and E is selected from the group consisting of aryl, cycloalkyl, heteroaryl, heterocycle, arylalkyl and cycloalkylalkyl.

Another aspect of the present invention is directed toward a compound of formula (I), wherein $A^2$, $A^3$ and $A^4$ are hydrogen;

$R^1$ and $R^2$ are hydrogen;

$R^3$ and $R^4$ taken together with the atoms to which they are attached form a cyclobutyl ring;

D is —O—;

$A^1$ is selected from the group consisting of alkenyl, alkylsulfonyl, cyano, heteroaryl, heteroarylalkyl, —$OR^{12}$, carboxyalkyl, —S-alkyl, —S(O)-alkyl, —C($R^{18}R^{19}$)—$OR^{20}$, —C(O)—N($R^{16}R^{17}$), —C($R^{18a}R^{19a}$)—C(O)N($R^{23}R^{24}$), —C(=NOH)—N(H)$_2$, —S(O)$_2$—N($R^{25}R^{26}$), —CO$_2R^{15}$, —C($R^{18a}R^{19a}$)—S(O)$_2$—N($R^{25}R^{26}$), and —C($R^{21}R^{22}$)—N($R^{23}R^{24}$) wherein $R^{12}$, $R^{15}$, $R^{16}$, $R^{17}$, $R^{18}$, $R^{19}$, $R^{18a}$, $R^{19a}$, $R^{21}$, $R^{22}$, $R^{23}$, $R^{24}$, $R^{25}$, and $R^{26}$ are as described in the summary of the invention; and E is selected from the group consisting of aryl, cycloalkyl, heteroaryl, heterocycle, arylalkyl and cycloalkylalkyl.

Another aspect of the present invention is directed toward a compound of formula (I), wherein $A^2$, $A^3$ and $A^4$ are hydrogen;

$R^1$ and $R^2$ are hydrogen; and $R^3$ and $R^4$ taken together with the atoms to which they are attached form a heterocycle, and $A^1$, D and E are as described in the summary of the invention.

Another aspect of the present invention is directed toward a compound of formula (I), wherein $A^2$, $A^3$ and $A^4$ are hydrogen;

$R^1$ and $R^2$ are hydrogen;

$R^3$ and $R^4$ taken together with the atoms to which they are attached form a heterocycle;

D is —O—; and $A^1$ and E are as described in the summary of the invention.

Another aspect of the present invention is directed toward a compound of formula (I), wherein $A^2$, $A^3$ and $A^4$ are hydrogen;

$R^1$ and $R^2$ are hydrogen;

$R^3$ and $R^4$ taken together with the atoms to which they are attached form a heterocycle;

E is as described in the summary of the invention;

D is —O—; and $A^1$ is selected from the group consisting of alkenyl, alkylsulfonyl, cyano, heteroaryl, heteroarylalkyl, —$OR^{12}$, carboxyalkyl, —S-alkyl, —S(O)-alkyl, —C($R^{18}R^{19}$)—$OR^{20}$, —C(O)—N($R^{16}R^{17}$), —C($R^{18a}R^{19a}$)—C(O)N($R^{23}R^{24}$), —C(=NOH)—N(H)$_2$, —S(O)$_2$—N($R^{25}R^{26}$), —CO$_2R^{15}$, —C($R^{18a}R^{19a}$)—S(O)$_2$—N($R^{25}R^{26}$) and —C($R^{21}R^{22}$)—N($R^{23}R^{24}$) wherein $R^{12}$, $R^{15}$, $R^{16}$, $R^{17}$, $R^{18}$, $R^{19}$, $R^{18a}$, $R^{19a}$, $R^{21}$, $R^{22}$, $R^{23}$, $R^{24}$, $R^{25}$, and $R^{26}$ are as described in the summary of the invention.

Another aspect of the present invention is directed toward a compound of formula (I), wherein $A^2$, $A^3$ and $A^4$ are hydrogen;

$R^1$ and $R^2$ are hydrogen;

$R^3$ and $R^4$ taken together with the atoms to which they are attached form a heterocycle;

D is —O—;

$A^1$ is selected from the group consisting of alkenyl, alkylsulfonyl, cyano, heteroaryl, heteroarylalkyl, —$OR^{12}$, carboxyalkyl, —S-alkyl, —S(O)-alkyl, —C($R^{18}R^{19}$)—$OR^{20}$, —C(O)—N($R^{16}R^{17}$), —C($R^{18a}R^{19a}$)—C(O)N($R^{23}R^{24}$), —C(=NOH)—N(H)$_2$, —S(O)$_2$—N($R^{25}R^{26}$), —CO$_2R^{15}$, —C($R^{18a}R^{19a}$)—S(O)$_2$—N($R^{25}R^{26}$), and —C($R^{21}R^{22}$)—N($R^{23}R^{24}$) wherein $R^{12}$, $R^{15}$, $R^{16}$, $R^{17}$, $R^{18}$, $R^{19}$, $R^{18a}$, $R^{19a}$, $R^{21}$, $R^{22}$, $R^{23}$, $R^{24}$, $R^{25}$, and $R^{26}$ are as described in the summary of the invention; and E is selected from the group consisting of aryl, cycloalkyl, heteroaryl, heterocycle, arylalkyl and cycloalkylalkyl.

Another aspect of the present invention is directed toward a compound of formula (I), wherein $A^2$, $A^3$ and $A^4$ are hydrogen;

$R^1$ and $R^2$ are hydrogen;

$R^4$ and E taken together with the atoms to which they are attached form a heterocycle; and $A^1$ and D are as described in the summary of the invention.

Another aspect of the present invention is directed toward a compound of formula (I), wherein $A^2$, $A^3$ and $A^4$ are hydrogen;

$R^1$ and $R^2$ are hydrogen;

$R^4$ and E taken together with the atoms to which they are attached form a heterocycle;

D is —O— and $A^1$ is as described in the summary of the invention.

Another aspect of the present invention is directed toward a compound of formula (I), wherein $A^2$, $A^3$ and $A^4$ are hydrogen;

$R^1$ and $R^2$ are hydrogen;

$R^4$ and E taken together with the atoms to which they are attached form a heterocycle;

D is —O—; and $A^1$ is selected from the group consisting of alkenyl, alkylsulfonyl, cyano, heteroaryl, heteroarylalkyl, —$OR^{12}$, carboxyalkyl, —S-alkyl, —S(O)-alkyl, —C($R^{18}R^{19}$)—$OR^{20}$, —C(O)—N($R^{16}R^{17}$), —C($R^{18a}R^{19a}$)—C(O)N($R^{23}R^{24}$), —C(=NOH)—N(H)$_2$, —S(O)$_2$—N($R^{25}R^{26}$), —CO$_2R^{15}$, —C($R^{18a}R^{19a}$)—S(O)$_2$—N($R^{25}R^{26}$), and —C($R^{21}R^{22}$)—N($R^{23}R^{24}$) wherein $R^{12}$, $R^{15}$, $R^{16}$, $R^{17}$, $R^{18}$, $R^{19}$, $R^{18a}$, $R^{19a}$, $R^{21}$, $R^{22}$, $R^{23}$, $R^{24}$, $R^{25}$, and $R^{26}$ are as described in the summary of the invention.

Another aspect of the present invention is directed toward a compound of formula (I), wherein $A^1$ is selected from the group consisting of alkylsulfonyl, arylsulfonyl, cycloalkylsulfonyl, heteroarylsulfonyl and heterocyclesulfonyl;

$A^2$, $A^3$ and $A^4$ are hydrogen;

D is —O—; and $R^1$, $R^2$, $R^3$, $R^4$, and E are as described in the summary of the invention.

Another aspect of the present invention is directed toward a compound of formula (I), wherein $A^1$ is —S(O)$_2$—N($R^{25}R^{26}$) wherein $R^{25}$ and $R^{26}$ are as described in the summary of the invention;

$A^2$, $A^3$ and $A^4$ are hydrogen;

D is —O—; and $R^1$, $R^2$, $R^3$, $R^4$, and E are as described in the summary of the invention.

Another aspect of the present invention is directed toward a compound of formula (I), wherein $A^1$ is —C(O)—N($R^{16}R^{17}$) wherein $R^{16}$ is selected from the group consisting of hydrogen and alkyl and $R^{17}$ is selected from the group consisting of arylalkyl and heteroarylalkyl;

D is —O—;

$A^2$, $A^3$ and $A^4$ are hydrogen; and $R^1$, $R^2$, $R^3$, $R^4$, and E are as described in the summary of the invention.

Another aspect of the present invention is directed toward a compound of formula (I), wherein $A^2$, $A^3$ and $A^4$ are hydrogen;
$R^1$ and $R^2$ are hydrogen;
D is selected from the group consisting of —S—, —S(O)— and —S(O)$_2$; and
$A^1$ is selected from the group consisting of alkenyl, alkylsulfonyl, cyano, heteroaryl, heteroarylalkyl, —OR$^{12}$, carboxyalkyl, —S-alkyl, —S(O)-alkyl, —C(R$^{18}$R$^{19}$)—OR$^{20}$, —C(O)—N(R$^{16}$R$^{17}$), —C(R$^{18a}$R$^{19a}$)—C(O)N(R$^{23}$R$^{24}$), —C(=NOH)—N(H)$_2$, —S(O)$_2$—N(R$^{25}$R$^{26}$), —CO$_2$R$^{15}$, —C(R$^{18a}$R$^{19a}$)—S(O)$_2$—N(R$^{25}$R$^{26}$), and —C(R$^{21}$R$^{22}$)—N(R$^{23}$R$^{24}$) wherein R$^{12}$, R$^{15}$, R$^{16}$, R$^{17}$, R$^{18}$, R$^{19}$, R$^{18a}$, R$^{19a}$, R$^{21}$, R$^{22}$, R$^{23}$, R$^{24}$, R$^{25}$, and R$^{26}$ are as described in the summary of the invention;

E is selected from the group consisting of aryl, cycloalkyl, heteroaryl, heterocycle, arylalkyl and cycloalkylalkyl; and $R^3$ and $R^4$ are each independently selected from the group consisting of hydrogen, alkyl and arylalkyl, or $R^3$ and $R^4$ together with the atom to which they are attached form a cycloalkyl ring.

Another aspect of the present invention is directed to a compound selected from the following group E-4-[(2-methyl-2-phenoxypropanoyl)amino]adamantane-1-carboxamide;
E-4-[(2-methyl-2-{[4-(trifluoromethyl)benzyl]oxy}propanoyl)amino]adamantane-1-carboxamide;
E-4-({2-methyl-2-[(2-methylcyclohexyl)oxy]propanoyl}amino)adamantane-1-carboxylic acid;
E-4-({2-methyl-2-[(3-methylcyclohexyl)oxy]propanoyl}amino)adamantane-1-carboxylic acid;
E-4-{[2-(cycloheptyloxy)-2-methylpropanoyl]amino}adamantane-1-carboxylic acid;
E-4-{[2-(cyclohexylmethoxy)-2-methylpropanoyl]amino}adamantane-1-carboxylic acid;
E-4-{[2-(4-chlorophenoxy)-2-methylpropanoyl]amino}adamantane-1-carboxylic acid;
E-4-{[2-(4-chlorophenoxy)-2-methylpropanoyl]amino}adamantane-1-carboxamide;
E-4-({2-methyl-2-[(4-methylcyclohexyl)oxy]propanoyl}amino)adamantane-1-carboxamide;
E-4-[(2-phenoxypropanoyl)amino]adamantane-1-carboxamide;
E-4-{[2-methyl-2-(2-methylphenoxy)propanoyl]amino}adamantane-1-carboxylic acid;
E-4-{[2-methyl-2-(4-methylphenoxy)propanoyl]amino}adamantane-1-carboxylic acid;
E-4-{[2-(2-chlorophenoxy)-2-methylpropanoyl]amino}adamantane-1-carboxylic acid;
E-4-{[2-(2-methoxyphenoxy)-2-methylpropanoyl]amino}adamantane-1-carboxamide;
E-4-{[2-(4-methoxyphenoxy)-2-methylpropanoyl]amino}adamantane-1-carboxamide;
E-4-({2-methyl-2-[3-(trifluoromethyl)phenoxy]propanoyl}amino)adamantane-1-carboxamide;
E-4-{[2-(3-methoxyphenoxy)-2-methylpropanoyl]amino}adamantane-1-carboxamide;
E-2-(4-Chloro-phenoxy)-N-(5-hydroxy-adamantan-2-yl)-2-methyl-propionamide;
E-{[2-Methyl-2-(4-methylphenoxy)propanoyl]amino}adamantane-1-carboxamide;
E-4-{[2-(3-Chlorophenoxy)-2-methylpropanoyl]amino}adamantane-1-carboxamide;
E-4-({2-Methyl-2-[4-(trifluoromethoxy)phenoxy]propanoyl}amino)adamantane-1-carboxamide;
E-4-{[2-(3-Bromophenoxy)-2-methylpropanoyl]amino}adamantane-1-carboxylic acid;
4-({[((E)-4-{[2-(4-Chlorophenoxy)-2-methylpropanoyl]amino}-1-adamantyl)carbonyl]amino}methyl)benzoic acid;
E-4-{[2-(2,3-Dimethylphenoxy)-2-methylpropanoyl]amino}adamantane-1-carboxylic acid;
tert-Butyl 4-(2-{[(E)-5-(aminocarbonyl)-2-adamantyl]amino}-1,1-dimethyl-2-oxoethoxy)phenylcarbamate;
E-N-[4-(Aminocarbonyl)benzyl]-4-{[2-(4-chlorophenoxy)-2-methylpropanoyl]amino}adamantane-1-carboxamide;
E-N-[4-(Aminocarbonyl)methyl]-4-{[2-(4-chlorophenoxy)-2-methylpropanoyl]amino}adamantane-1-carboxamide;
3-({[((E)-4-{[2-(4-Chlorophenoxy)-2-methylpropanoyl]amino}-1-adamantyl)carbonyl]amino}methyl)benzoic acid;
E-4-({2-[(5-Bromopyridin-2-yl)oxy]-2-methylpropanoyl}amino)adamantane-1-carboxamide;
E-4-{[2-(2-Cyanophenoxy)-2-methylpropanoyl]amino}adamantane-1-carboxamide;
E-4-{[2-(4-Hydroxyphenoxy)-2-methylpropanoyl]amino}adamantane-1-carboxamide;
((E)-4-{[2-(4-Chlorophenoxy)-2-methylpropanoyl]amino}-1-adamantyl)acetic acid;
N-[(E)-5-(2-Amino-2-oxoethyl)-2-adamantyl]-2-(4-chlorophenoxy)-2-methylpropanamide;
2-(4-Chlorophenoxy)-2-methyl-N-[(E)-5-(2H-tetraazol-5-ylmethyl)-2-adamantyl]propanamide;
N-{(E)-5-[(Aminosulfonyl)methyl]-2-adamantyl}-2-(4-chlorophenoxy)-2-methylpropanamide;
N-{(E)-5-[(Z)-Amino(hydroxyimino)methyl]-2-adamantyl}-2-(4-chlorophenoxy)-2-methylpropanamide;
E-N-[4-(Aminosulfonyl)benzyl]-4-{[2-(4-chlorophenoxy)-2-methylpropanoyl]amino}adamantane-1-carboxamide;
E-4-{[2-(4-Chlorophenoxy)-2-methylpropanoyl]amino}-N-(4-{[(methylsulfonyl)amino]carbonyl}benzyl)adamantane-1-carboxamide;
E-4-({2-[(4-Chlorophenyl)thio]-2-methylpropanoyl}amino)adamantane-1-carboxylic acid;
E-4-({2-[(4-Methoxyphenyl)thio]-2-methylpropanoyl}amino)adamantane-1-carboxamide;
E-4-({2-[(4-Methoxyphenyl)sulfinyl]-2-methylpropanoyl}amino)adamantane-1-carboxamide;
E-4-({2-[(4-Methoxyphenyl)sulfonyl]-2-methylpropanoyl}amino)adamantane-1-carboxamide;
E-4-({2-[4-Chloro-2-(pyrrolidin-1-ylsulfonyl)phenoxy]-2-methylpropanoyl}amino)adamantane-1-carboxamide;
E-4-({2-Methyl-2-[4-(methylsulfonyl)phenoxy]propanoyl}amino)adamantane-1-carboxamide;
E-4-({2-Methyl-2-[2-(methylsulfonyl)phenoxy]propanoyl}amino)adamantane-1-carboxamide;
E-4-[(2-{4-Chloro-2-[(diethylamino)sulfonyl]phenoxy}-2-methylpropanoyl)amino]adamantane-1-carboxamide;
E-4-({2-Methyl-2-[4-(pyrrolidin-1-ylsulfonyl)phenoxy]propanoyl}amino)adamantane-1-carboxamide;
2-(2-Chloro-4-fluorophenoxy)-N-[(E)-5-hydroxy-2-adamantyl]-2-methylpropanamide;
2-(2-Chloro-4-fluorophenoxy)-2-methyl-N-[(E)-5-(2H-tetraazol-5-yl)-2-adamantyl]propanamide;
2-(2-Chloro-4-fluorophenoxy)-2-methyl-N-[(E)-5-(methylthio)-2-adamantyl]propanamide;
2-(2-Chloro-4-fluorophenoxy)-2-methyl-N-[(E)-5-(methylsulfonyl)-2-adamantyl]propanamide;
2-(2-Chloro-4-fluorophenoxy)-2-methyl-N-[(E)-5-(methylsulfinyl)-2-adamantyl]propanamide;
N-[(E)-5-(Aminosulfonyl)-2-adamantyl]-2-(4-chlorophenoxy)-2-methylpropanamide;

E-4-({[1-(4-Chlorophenoxy)cyclobutyl]carbonyl}amino)
  adamantane-1-carboxamide;
4-[({[((E)-4-{[2-(4-Chlorophenoxy)-2-methylpropanoyl]
  amino}-1-adamantyl)methyl]sulfonyl}amino)methyl]
  benzoic acid;
2-(4-Chlorophenoxy)-N-[(E)-5-(1H-imidazol-2-yl)-2-ada-
  mantyl]-2-methylpropanamide;
(2E)-3-((E)-4-{[2-(4-Chlorophenoxy)-2-methylpropanoyl]
  amino}-1-adamantyl)acrylic acid;
(E)-4-[(2-Methyl-2-{[5-(1H-pyrazol-1-yl)pyridin-2-yl]
  oxy}propanoyl)amino]adamantane-1-carboxamide;
2-(4-Chlorophenoxy)-N-[(E)-5-isoxazol-5-yl-2-adamantyl]-
  2-methylpropanamide;
2-(4-Chlorophenoxy)-2-methyl-N-{(E)-5-[(2-morpholin-4-
  ylethoxy)methyl]-2-adamantyl}propanamide;
N-[(E)-5-(Aminosulfonyl)-2-adamantyl]-2-(2-chlorophe-
  noxy)-2-methylpropanamide;
N-[(E)-5-(Aminosulfonyl)-2-adamantyl]-2-methyl-2-(2-
  methylphenoxy)propanamide;
N-[(E)-5-(Aminosulfonyl)-2-adamantyl]-2-methyl-2-(4-
  methylphenoxy)propanamide;
N-[(E)-5-(Aminosulfonyl)-2-adamantyl]-2-methyl-2-[2-
  (trifluoromethyl)phenoxy]propanamide;
N-[(E)-5-(Aminosulfonyl)-2-adamantyl]-2-methyl-2-[2-
  (trifluoromethoxy)phenoxy]propanamide;
N-[(E)-5-(Aminosulfonyl)-2-adamantyl]-2-(2-chloro-4-
  fluorophenoxy)-2-methylpropanamide;
E-4-{[2-(2-chlorophenoxy)-2-methyl-3-phenylpropanoyl]
  amino}adamantane-1-carboxamide;
2-(4-chlorophenoxy)-N-[(E)-5-hydroxy-2-adamantyl]-2-
  methylpropanamide;
E-4-({2-methyl-2-[(5-morpholin-4-ylpyridin-2-yl)oxy]
  propanoyl}amino)adamantane-1-carboxamide;
E-4-{[2-methyl-2-(pyridin-2-yloxy)propanoyl]
  amino}adamantane-1-carboxamide;
2-(4-chlorophenoxy)-2-methyl-N-{(E)-5-[(methylamino)
  sulfonyl]-2-adamantyl}propanamide;
3-((E)-4-{[2-(4-chlorophenoxy)-2-methylpropanoyl]
  amino}-1-adamantyl)propanoic acid;
2-(4-chlorophenoxy)-N-{(E)-5-[(dimethylamino)sulfonyl]-
  2-adamantyl}-2-methylpropanamide;
E-4-[(2-{5-(1H-imidazol-1-yl)pyridin-2-yl]oxy}-2-methyl-
  propanoyl)amino]adamantane-1-carboxamide;
2-(4-chlorophenoxy)-2-methyl-N-[(E)-5-(1H-pyrazol-3-yl)-
  2-adamantyl]propanamide;
N-[(E)-5-(aminosulfonyl)-2-adamantyl]-2-(3-chlorophe-
  noxy)-2-methylpropanamide;
N-[(E)-5-(aminosulfonyl)-2-adamantyl]-2-methyl-2-(3-me-
  thylphenoxy)propanamide;
N-[(E)-5-(aminosulfonyl)-2-adamantyl]-2-(2-methoxyphe-
  noxy)-2-methylpropanamide;
N-[(E)-5-(aminosulfonyl)-2-adamantyl]-2-(3-methoxyphe-
  noxy)-2-methylpropanamide;
N-[(E)-5-(aminosulfonyl)-2-adamantyl]-2-(4-methoxyphe-
  noxy)-2-methylpropanamide;
N-[(E)-5-(aminosulfonyl)-2-adamantyl]-2-(4-cyanophe-
  noxy)-2-methylpropanamide;
E-4-{[2-methyl-2-(2-methylphenoxy)propanoyl]
  amino}adamantane-1-carboxamide;
E-4-{[2-methyl-2-(3-methylphenoxy)propanoyl]
  amino}adamantane-1-carboxamide;
E-4-[(2-methyl-2-{[(1S,2S)-2-methylcyclohexyl]
  oxy}propanoyl)amino]adamantane-1-carboxylic acid;
E-4-({2-methyl-2-[(2-methylcyclohexyl)oxy]
  propanoyl}amino)adamantane-1-carboxamide
E-4-{[2-(cycloheptyloxy)-2-methylpropanoyl]
  amino}adamantane-1-carboxamide;
E-4-{[2-(cyclohexylmethoxy)-2-methylpropanoyl]
  amino}adamantane-1-carboxamide;
E-4-({2-methyl-2-[(3-methylcyclohexyl)oxy]
  propanoyl}amino)adamantane-1-carboxamide;
E-4-{[2-(2-chlorophenoxy)-2-methylpropanoyl]
  amino}adamantane-1-carboxamide;
4-{[({(E)-4-[(2-methyl-2-phenoxypropanoyl)amino]-1-
  adamantyl}carbonyl)amino]methyl}benzoic acid;
E-4-({2-[(4,4-dimethylcyclohexyl)oxy]-2-
  methylpropanoyl}amino)adamantane-1-carboxylic acid;
E-4-{[2-methyl-2-(1,2,3,4-tetrahydronaphthalen-2-yloxy)
  propanoyl]amino}adamantane-1-carboxylic acid;
E-4-{[2-(4-bromophenoxy)-2-methylpropanoyl]
  amino}adamantane-1-carboxylic acid;
E-4-{[2-methyl-2-(1-naphthyloxy)propanoyl]
  amino}adamantane-1-carboxylic acid;
E-4-{[2-(2,3-dichlorophenoxy)-2-methylpropanoyl]
  amino}adamantane-1-carboxylic acid;
E-4-{[2-(2,4-dichlorophenoxy)-2-methylpropanoyl]
  amino}adamantane-1-carboxylic acid;
E-4-{[2-(2,5-dichlorophenoxy)-2-methylpropanoyl]
  amino}adamantane-1-carboxylic acid;
E-4-{[2-(2,4-dimethylphenoxy)-2-methylpropanoyl]
  amino}adamantane-1-carboxylic acid;
E-4-{[2-(2,5-dimethylphenoxy)-2-methylpropanoyl]
  amino}adamantane-1-carboxylic acid;
E-4-{[2-methyl-2-(2-naphthyloxy)propanoyl]
  amino}adamantane-1-carboxylic acid;
E-4-{[2-(4-bromo-2-fluorophenoxy)-2-methylpropanoyl]
  amino}adamantane-1-carboxylic acid;
E-4-({2-methyl-2-[(7-methyl-2,3-dihydro-1H-inden-4-yl)
  oxy]propanoyl}amino)adamantane-1-carboxylic acid;
E-4-{[2-(4-bromo-2-chlorophenoxy)-2-methylpropanoyl]
  amino}adamantane-1-carboxylic acid;
E-4-{[2-(1,1'-biphenyl-3-yloxy)-2-methylpropanoyl]
  amino}adamantane-1-carboxylic acid;
E-4-{[2-(2-bromophenoxy)-2-methylpropanoyl]
  amino}adamantane-1-carboxylic acid;
E-N-[4-(aminocarbonyl)benzyl]-4-[(2-methyl-2-phenox-
  ypropanoyl)amino]adamantane-1-carboxamide;
E-4-{[2-(4-chlorophenoxy)-2-methylpropanoyl]amino}-N-
  (1,3-thiazol-5-ylmethyl)adamantane-1-carboxamide;
E-4-{[2-(4-chlorophenoxy)-2-methylpropanoyl]amino}-N-
  (pyridin-4-ylmethyl)adamantane-1-carboxamide;
E-4-{[2-(4-aminophenoxy)-2-methylpropanoyl]
  amino}adamantane-1-carboxamide;
E-4-({2-methyl-2-[2-(trifluoromethoxy)phenoxy]
  propanoyl}amino)adamantane-1-carboxamide;
E-4-({2-methyl-2-[2-(trifluoromethyl)phenoxy]
  propanoyl}amino)adamantane-1-carboxamide;
E-4-({2-methyl-2-[4-(pyrrolidin-1-ylsulfonyl)phenoxy]
  propanoyl}amino)adamantane-1-carboxamide;
2-(2-chloro-4-fluorophenoxy)-N-[(E)-5-hydroxy-2-ada-
  mantyl]-2-methylpropanamide;
2-(2-chloro-4-fluorophenoxy)-N-[(E)-5-cyano-2-adaman-
  tyl]-2-methylpropanamide;
E-4-[(2-methyl-2-{4-[(trifluoroacetyl)amino]
  phenoxy}propanoyl)amino] adamantane-1-carboxamide;
E-4-{[2-(3-bromo-4-methoxyphenoxy)-2-methylpropanoyl]
  amino}adamantane-1-carboxamide;
E-4-{[2-(2,5-dibromo-4-methoxyphenoxy)-2-methylpro-
  panoyl]amino}adamantane-1-carboxamide;
E-4-{[2-(2-bromo-4-methoxyphenoxy)-2-methylpropanoyl]
  amino}adamantane-1-carboxamide;
E-4-{[2-(2-chloro-4-fluorophenoxy)-2-methylpropanoyl]
  amino}-N,N-dimethyladamantane-1-carboxamide;

2-(4-chlorophenoxy)-N-((E)-5-{[(4-methoxy-6-methylpyrimidin-2-yl)amino]methyl}-2-adamantyl)-2-methylpropanamide;
E-4-{[2-(4-{[(tert-butylamino)carbonyl]amino}phenoxy)-2-methylpropanoyl]amino}adamantane-1-carboxamide;
ethyl 4-(2-{[(E)-5-(aminocarbonyl)-2-adamantyl]amino}-1,1-dimethyl-2-oxoethoxy)phenylcarbamate;
E-4-[(2-methyl-2-{4-[(propylsulfonyl)amino]phenoxy}propanoyl)amino] adamantane-1-carboxamide;
E-4-[(2-{4-[(3,3-dimethylbutanoyl)amino]phenoxy}-2-methylpropanoyl)amino] adamantane-1-carboxamide;
E-4-{[2-methyl-2-(phenylsulfinyl)propanoyl]amino}adamantane-1-carboxylic acid;
E-4-{[2-methyl-2-(phenylsulfonyl)propanoyl]amino}adamantane-1-carboxylic acid;
N-[(E)-5-cyano-2-adamantyl]-2-[(4-methoxyphenyl)sulfonyl]-2-methylpropanamide;
2-[(4-methoxyphenyl)sulfonyl]-2-methyl-N-[(E)-5-(2H-tetraazol-5-yl)-2-adamantyl]propanamide; and
E-4-({2-[4-(benzyloxy)phenoxy]-2-methylpropanoyl}amino)adamantane-1-carboxamide.

Another embodiment of the present invention discloses a method of inhibiting 11-beta-hydroxysteroid dehydrogenase Type I enzyme, comprising administering to a mammal, a therapeutically effective amount of the compound of formula (I).

Another embodiment of the present invention discloses a method of treating disorders in a mammal by inhibiting 11-beta-hydroxysteroid dehydrogenase Type I enzyme, comprising administering to a mammal, a therapeutically effective amount of the compound of formula (I).

Another embodiment of the present invention discloses a method of treating non-insulin dependent type 2 diabetes in a mammal by inhibiting 11-beta-hydroxysteroid dehydrogenase Type I enzyme comprising administering to a mammal, a therapeutically effective amount of the compound of formula (I).

Another embodiment of the present invention discloses a method of treating insulin resistance in a mammal by inhibiting 11-beta-hydroxysteroid dehydrogenase Type I enzyme comprising administering to a mammal, a therapeutically effective amount of the compound of formula (I).

Another embodiment of the present invention discloses a method of treating obesity in a mammal by inhibiting 11-beta-hydroxysteroid dehydrogenase Type I enzyme comprising administering to a mammal, a therapeutically effective amount of the compound of formula (I).

Another embodiment of the present invention discloses a method of treating lipid disorders in a mammal by inhibiting 11-beta-hydroxysteroid dehydrogenase Type I enzyme comprising administering to a mammal, a therapeutically effective amount of the compound of formula (I).

Another embodiment of the present invention discloses a method of treating metabolic syndrome in a mammal by inhibiting 11-beta-hydroxysteroid dehydrogenase Type I enzyme comprising administering to a mammal, a therapeutically effective amount of the compound of formula (I).

Another embodiment of the present invention discloses a method of treating diseases and conditions that are mediated by excessive glucocorticoid action in a mammal by inhibiting 11-beta-hydroxysteroid dehydrogenase Type I enzyme comprising administering to a mammal, a therapeutically effective amount of the compound of formula (I).

Another embodiment of the present invention discloses a pharmaceutical composition comprising a therapeutically effective amount of the compound of formula (I) in combination with a pharmaceutically suitable carrier.

Definition of Terms

The term "alkenyl" as used herein, refers to a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl. Alkenyls of the present invention can be unsubstituted or substituted with one substituent selected from the group consisting of carboxy, alkoxycarbonyl and aryloxycarbonyl.

The term "alkoxy" as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy and hexyloxy.

The term "alkoxyalkyl" as used herein, refers to an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl and methoxymethyl.

The term "alkoxycarbonyl" as used herein, refers to an alkoxy group, as defined herein, appended to the parent molecular moiety through a carbonyl group, as defined herein. Representative examples of alkoxycarbonyl include, but are not limited to, methoxycarbonyl, ethoxycarbonyl and tert-butoxycarbonyl.

The term "alkyl" as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl and n-decyl.

The term "alkylcarbonyl" as used herein, refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl and 1-oxopentyl.

The term "alkylsulfonyl" as used herein, refers to an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkyl-NH" as used herein, refers to an alkyl group, as defined herein, appended to the parent molecular moiety through a nitrogen atom.

The term "alkyl-NH-alkyl" as used herein, refers to an alkyl-NH group, as defined herein, appended to the parent molecular moiety through an alkyl group, as defined herein.

The term "aryl" as used herein, means a phenyl group, or a bicyclic or a tricyclic fused ring system. Bicyclic fused ring systems are exemplified by a phenyl group appended to the parent molecular moiety and fused to a cycloalkyl group, as defined herein, a phenyl group, a heteroaryl group, as defined herein, or a heterocycle, as defined herein. Tricyclic fused ring systems are exemplified by an aryl bicyclic fused ring system, as defined herein and fused to a cycloalkyl group, as defined herein, a phenyl group, a heteroaryl group, as defined herein, or a heterocycle, as defined herein. Representative examples of aryl include, but are not limited to, anthracenyl, azulenyl, fluorenyl, indanyl, indenyl, naphthyl, phenyl and tetrahydronaphthyl.

The aryl groups of this invention may be optionally substituted with 1, 2, 3, 4 or 5 substituents independently selected from alkenyl, alkoxy, alkoxyalkoxy, alkoxyalkyl, alkoxycarbonyl, alkoxycarbonylalkyl, alkyl, alkylcarbonyl, alkylsulfonyl, alkynyl, aryl, arylalkoxy, arylcarbonyl, aryloxy, arylsulfonyl, carboxy, carboxyalkyl, cyano, cyanoalkyl, ethylenedioxy, formyl, haloalkoxy, haloalkyl, halogen, heteroaryl, heteroarylalkyl, heteroarylcarbonyl, heterocycle, heterocyclecarbonyl, heterocycleoxy, heterocyclesulfonyl, hydroxy, hydroxyalkyl, nitro, $R_fR_gN$—, $R_fR_g$Nalkyl, $R_fR_g$N-carbonyl, —N(H)C(O)N(H)(alkyl), and $R_fR_g$Nsulfonyl, wherein $R_f$ and $R_g$ are independently selected from the group consisting of hydrogen, alkyl, alkoxyalkyl, alkoxycarbonyl, alkylcarbonyl, alkylsulfonyl, cycloalkyl, haloalkyl, haloalkylcarbonyl and cycloalkylalkyl wherein the cycloalkyl, the cycloalkyl of cycloalkylalkyl as represented by $R_f$ and $R_g$ are each independently unsubstituted or substituted with 1, 2 or 3 substituents independently selected from the group consisting of halogen, alkyl and haloalkyl. The substituent aryl, the aryl of arylalkoxy, the aryl of arylcarbonyl, the aryl of aryloxy, the aryl of arylsulfonyl, the substituent heteroaryl, the heteroaryl of heteroarylalkyl, the heteroaryl of heteroarylcarbonyl, the substituent heterocycle, the heterocycle of heterocyclecarbonyl, the heterocycle of heterocycleoxy, the heterocycle of heterocyclesulfonyl may be optionally substituted with 1, 2 or 3 substituents independently selected from the group consisting of alkoxy, alkoxyalkyl, alkoxycarbonyl, alkyl, alkylcarbonyl, alkynyl, carboxy, carboxyalkyl, cyano, haloalkyl, halogen, hydroxy, hydroxyalkyl, nitro, $R_fR_gN$—, $R_fR_g$Nalkyl, $R_fR_g$Ncarbonyl and $R_fR_g$Nsulfonyl wherein $R_f$ and $R_g$ are as described herein.

The term "arylalkyl" as used herein, refers to an aryl group, as defined herein, appended to the parent molecular moiety through an alkyl group, as defined herein. Representative examples of arylalkyl include, but are not limited to, benzyl, 2-phenylethyl, 3-phenylpropyl and 2-naphth-2-ylethyl.

The term "arylcarbonyl" as used herein, refers to an aryl group, as defined herein, appended to the parent molecular moiety through a carbonyl group, as defined herein. Representative examples of arylcarbonyl include, but are not limited to, benzoyl and naphthoyl.

The term "aryl-NH-" as used herein, refers to an aryl group, as defined herein, appended to the parent molecular moiety through a nitrogen atom.

The term "aryl-NH-alkyl" as used herein, refers to an aryl-NH— group, as defined herein, appended to the parent molecular moiety through an alkyl group, as defined herein.

The term "arylalkoxy" as used herein, refers to an aryl group, as defined herein, appended to the parent molecular moiety through an alkoxy moiety, as defined herein.

The term "aryloxy" as used herein, refers to an aryl group, as defined herein, appended to the parent molecular moiety through an oxy moiety, as defined herein. Representative examples of aryloxy include, but are not limited to phenoxy, naphthyloxy, 3-bromophenoxy, 4-chlorophenoxy, 4-methylphenoxy and 3,5-dimethoxyphenoxy.

The term "aryloxyalkyl" as used herein, refers to an aryloxy group, as defined herein, appended to the parent molecular moiety through an alkyl group, as defined herein.

The term "aryloxycarbonyl" as used herein, refers to an aryloxy group, as defined herein, appended to the parent molecular moiety through a carbonyl group, as defined herein.

The term "arylsulfonyl" as used herein, refers to an aryl group, as defined herein, appended to the parent molecular moiety through a sulfonyl group, as defined herein. Representative examples of arylsulfonyl include, but are not limited to, phenylsulfonyl, 4-bromophenylsulfonyl and naphthylsulfonyl.

The term "carbonyl" as used herein refers to a —C(O)— group.

The term "carboxy" as used herein refers to a —C(O)—OH group.

The term "carboxyalkyl" as used herein refers to a carboxy group as defined herein, appended to the parent molecular moiety through an alkyl group as defined herein.

The term "carboxycycloalkyl" as used herein refers to a carboxy group as defined herein, appended to the parent molecular moiety through an cycloalkyl group as defined herein.

The term "cycloalkyl" as used herein, refers to a monocyclic, bicyclic, or tricyclic ring system. Monocyclic ring systems are exemplified by a saturated cyclic hydrocarbon group containing from 3 to 8 carbon atoms. Examples of monocyclic ring systems include cyclopropyl, cyclobutyl, cyclopentyl, cyclohexyl, cycloheptyl and cyclooctyl. Bicyclic fused ring systems are exemplified by a cycloalkyl group appended to the parent molecular moiety and fused to a cycloalkyl group, as defined herein, a phenyl group, a heteroaryl group, as defined herein, or a heterocycle, as defined herein. Tricyclic fused ring systems are exemplified by a cycloalkyl bicyclic fused ring system, as defined herein and fused to a cycloalkyl group, as defined herein, a phenyl group, a heteroaryl group, as defined herein, or a heterocycle, as defined herein. Bicyclic ring systems are also exemplified by a bridged monocyclic ring system in which two non-adjacent carbon atoms of the monocyclic ring are linked by an alkylene bridge of between one and three additional carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane and bicyclo[4.2.1]nonane. Tricyclic ring systems are also exemplified by a bicyclic ring system in which two non-adjacent carbon atoms of the bicyclic ring are linked by a bond or an alkylene bridge of between one and three carbon atoms. Representative examples of tricyclic-ring systems include, but are not limited to, tricyclo[3.3.1.0$^{3,7}$]nonane and tricyclo[3.3.1.1$^{3,7}$]decane (adamantane).

The cycloalkyl groups of this invention may be substituted with 1, 2, 3, 4 or 5 substituents independently selected from alkenyl, alkoxy, alkoxyalkoxy, alkoxyalkyl, alkoxycarbonyl, alkoxycarbonylalkyl, alkyl, alkylcarbonyl, alkynyl, aryl, arylalkyl, arylcarbonyl, aryloxy, arylsulfonyl, carboxy, carboxyalkyl, cyano, cyanoalkyl, cycloalkyl, ethylenedioxy, formyl, haloalkoxy, haloalkyl, halogen, heteroaryl, heteroarylalkyl, heteroarylcarbonyl, heterocycle, heterocyclealkyl, heterocyclecarbonyl, heterocycleoxy, hydroxy, hydroxyalkyl, nitro, $R_fR_gN$—, $R_fR_g$Nalkyl, $R_fR_g$Ncarbonyl and $R_fR_g$Nsulfonyl, wherein $R_f$ and $R_g$ are independently selected from the group consisting of hydrogen, alkyl, alkoxyalkyl, alkoxycarbonyl, alkylcarbonyl, alkylsulfonyl, cycloalkyl, haloalkyl, haloalkylcarbonyl and cycloalkylalkyl wherein the cycloalkyl, the cycloalkyl of cycloalkylalkyl as represented by $R_f$ and $R_g$ are each independently unsubstituted or substituted with 1, 2 or 3 substituents independently selected from the group consisting of halogen, alkyl and haloalkyl. The substituent aryl, the aryl of arylalkyl, the aryl of arylcarbonyl, the aryl of aryloxy, the aryl of arylsulfonyl, the substituent heteroaryl, the heteroaryl of heteroarylalkyl, the heteroaryl of heteroarylcarbonyl, the substituent heterocycle, the heterocycle of heterocyclealkyl, the heterocycle of heterocyclecarbonyl, the heterocycle of heterocycleoxy, the heterocycle of heterocyclesulfonyl may be optionally substituted with 0, 1, 2 or 3 substituents independently selected from the group consisting of alkoxy, alkoxyalkyl, alkoxycarbonyl, alkyl, alkylcarbonyl, alkynyl, carboxy, carboxyalkyl, cyano, haloalkyl, halogen, hydroxy, hydroxyalkyl, nitro, $R_fR_gN$—, $R_fR_g$-Nalkyl, $R_fR_g$Ncarbonyl and $R_fR_g$Nsulfonyl wherein $R_f$ and $R_g$ are as described herein.

The term "cycloalkylalkyl" as used herein, refers to a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl and 4-cycloheptylbutyl.

The term "cycloalkylcarbonyl" as used herein, refers to cycloalkyl group, as defined herein, appended to the parent molecular moiety through a carbonyl group, as defined herein. Representative examples of cycloalkylcarbonyl include, but are not limited to, cyclopropylcarbonyl, 2-cyclobutylcarbonyl and cyclohexylcarbonyl.

The term "cycloalkyloxy" as used herein, refers to cycloalkyl group, as defined herein, appended to the parent molecular moiety through an oxy group, as defined herein.

The term "cycloalkylsulfonyl" as used herein, refers to cycloalkyl group, as defined herein, appended to the parent molecular moiety through a sulfonyl group, as defined herein. Representative examples of cycloalkylsulfonyl include, but are not limited to, cyclohexylsulfonyl and cyclobutylsulfonyl.

The term "halo" or "halogen" as used herein, refers to —Cl, —Br, —I or —F.

The term "haloalkyl" as used herein, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl and 2-chloro-3-fluoropentyl.

The term "haloalkylcarbonyl" as used herein, refers to a haloalkyl group, as defined herein, appended to the parent molecular moiety through a carbonyl group, as defined herein.

The term "heteroaryl" as used herein, refers to an aromatic monocyclic ring or an aromatic bicyclic ring system. The aromatic monocyclic rings are five or six membered rings containing at least one heteroatom independently selected from the group consisting of N, O and S. The five membered aromatic monocyclic rings have two double bonds and the six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. Representative examples of heteroaryl include, but are not limited to, benzimidazolyl, benzofuranyl, benzothiazolyl, benzothienyl, benzoxazolyl, furyl, imidazolyl, indazolyl, indolyl, indolizinyl, isobenzofuranyl, isoindolyl, isoxazolyl, isoquinolinyl, isothiazolyl, naphthyridinyl, oxadiazolyl, oxazolyl, phthalazinyl, pyridinyl, pyridazinyl, pyrimidinyl, pyrazinyl, pyrazolyl, pyrrolyl, quinolinyl, quinolizinyl, quinoxalinyl, quinazolinyl, tetrazolyl, thiadiazolyl, thiazolyl, thienyl, triazolyl and triazinyl.

The term "heteroarylalkyl" as used herein, refers to a heteroaryl, as defined herein, appended to the parent molecular moiety through an alkyl group, as defined herein.

The heteroaryls of this invention may be optionally substituted with 1, 2 or 3 substituents independently selected from alkenyl, alkoxy, alkoxyalkoxy, alkoxyalkyl, alkoxycarbonyl, alkoxycarbonylalkyl, alkyl, alkylcarbonyl, alkynyl, aryl, arylalkyl, arylcarbonyl, aryloxy, arylsulfonyl, carboxy, carboxyalkyl, cyano, cyanoalkyl, cycloalkyl, ethylenedioxy, formyl, haloalkoxy, haloalkyl, halogen, heteroaryl, heteroarylalkyl, heterocycle, heterocyclealkyl, heterocyclecarbonyl, heterocycleoxy, hydroxy, hydroxyalkyl, nitro, $R_fR_gN$—, $R_fR_g$-Nalkyl, $R_fR_g$Ncarbonyl and $R_fR_g$Nsulfonyl, wherein $R_f$ and $R_g$ are independently selected from the group consisting of hydrogen, alkyl, alkoxyalkyl, alkoxycarbonyl, alkylcarbonyl, alkylsulfonyl, cycloalkyl, haloalkyl, haloalkylcarbonyl and cycloalkylalkyl wherein the cycloalkyl, the cycloalkyl of cycloalkylalkyl as represented by $R_f$ and $R_g$ are each independently unsubstituted or substituted with 1, 2 or 3 substituents independently selected from the group consisting of halogen, alkyl and haloalkyl. The substituent aryl, the aryl of arylalkyl, the aryl of arylcarbonyl, the aryl of aryloxy, the aryl of arylsulfonyl, the substituent heteroaryl, the heteroaryl of heteroarylalkyl, the substituent hetero cycle, the heterocycle of heterocyclealkyl, the hetero cycle of heterocyclecarbonyl, the heterocycle of heterocycleoxy may be optionally substituted with 1, 2 or 3 substituents independently selected from the group consisting of alkoxy, alkoxyalkyl, alkoxycarbonyl, alkyl, alkylcarbonyl, alkynyl, carboxy, carboxyalkyl, cyano, haloalkyl, halogen, hydroxy, hydroxyalkyl, nitro, $R_fR_gN$—, $R_fR_g$Nalkyl, $R_fR_g$Ncarbonyl and $R_fR_g$Nsulfonyl wherein $R_f$ and $R_g$ are as described above.

The term "heterocycle" as used herein, refers to a non-aromatic monocyclic ring or a non-aromatic bicyclic ring. The non-aromatic monocyclic ring is a three, four, five, six, seven, or eight membered ring containing at least one heteroatom, independently selected from the group consisting of N, O and S. Representative examples of monocyclic ring systems include, but are not limited to, azetidinyl, aziridinyl, diazepinyl, dithianyl, imidazolinyl, imidazolidinyl, isothiazolinyl, isoxazolinyl, isoxazolidinyl, morpholinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydro-2H-pyranyl, tetrahydro-2H-pyran-2-yl, tetrahydro-2H-pyran-4-yl, tetrahydrothienyl, thiazolinyl, thiazolidinyl, thiomorpholinyl, 1,1-dioxidothiomorpholinyl (thiomorpholine sulfone) and thiopyranyl. The bicyclic heterocycles are exemplified by a monocyclic heterocycle appended to the parent molecular moiety and fused to a monocyclic cycloalkyl group, as defined herein, a monocyclic aryl group, a monocyclic heteroaryl group, as defined herein, or a monocyclic heterocycle, as defined herein. Bicyclic ring systems are also exemplified by a bridged monocyclic ring system in which two non-adjacent atoms of the monocyclic ring are linked by a bridge of between one and three additional atoms selected from the group consisting of carbon, nitrogen and oxygen. Representative examples of bicyclic ring systems include but are not limited to, for example, benzopyranyl, benzothiopyranyl, benzodioxinyl, 1,3-benzodioxolyl, cinnolinyl, 1,5-diazocanyl, 3,9-diaza-bicyclo[4.2.1]non-9-yl, 3,7-diazabicyclo[3.3.1]nonane, octahydro-pyrrolo[3,4-c]pyrrole, indolinyl, isoindolinyl, 2,3,4,5-tetrahydro-1H-benzo[c]azepine, 2,3,4,5-tetrahydro-1H-benzo[b]azepine, 2,3,4,5-tetrahydro-1H-benzo[d]azepine, tetrahydroisoquinolinyl and tetrahydroquinolinyl.

The heterocycles of this invention may be optionally substituted with 1, 2 or 3 substituents independently selected from alkenyl, alkoxy, alkoxyalkoxy, alkoxyalkyl, alkoxycarbonyl, alkoxycarbonylalkyl, alkyl, alkylcarbonyl, alkynyl, aryl, arylalkyl, arylcarbonyl, aryloxy, arylsulfonyl, carboxy, carboxyalkyl, cyano, cyanoalkyl, ethylenedioxy, formyl, haloalkoxy, haloalkyl, halogen, heteroaryl, heteroarylalkyl, heterocycle, heterocyclealkyl, heterocyclecarbonyl, heterocycleoxy, hydroxy, hydroxyalkyl, nitro, $R_fR_gN$—, $R_fR_g$-Nalkyl, $R_fR_g$Ncarbonyl and $R_fR_g$Nsulfonyl, wherein $R_f$ and $R_g$ are independently selected from the group consisting of hydrogen, alkyl, alkoxyalkyl, alkoxycarbonyl, alkylcarbonyl, alkylsulfonyl, cycloalkyl, haloalkyl, haloalkylcarbonyl and cycloalkylalkyl wherein the cycloalkyl, the cycloalkyl of cycloalkylalkyl as represented by $R_f$ and $R_g$ are each independently unsubstituted or substituted with 1, 2 or 3 substituents independently selected from the group consisting of halogen, alkyl and haloalkyl. The substituent aryl, the aryl of arylalkyl, the aryl of arylcarbonyl, the aryl of aryloxy, the aryl of arylsulfonyl, the heteroaryl, the heteroaryl of heteroarylalkyl, the substituent heterocycle, the heterocycle of heterocyclealkyl, the heterocycle of heterocyclecarbonyl, the heterocycle of heterocycleoxy, may be optionally substituted with 1, 2 or 3 substituents independently selected from the group consisting of alkoxy, alkoxyalkyl, alkoxycarbonyl, alkyl, alkylcarbonyl, alkynyl, carboxy, carboxyalkyl, cyano, haloalkyl, halogen, hydroxy, hydroxyalkyl, nitro, $R_fR_gN$—, $R_fR_g$-Nalkyl, $R_fR_g$Ncarbonyl and $R_fR_g$Nsulfonyl wherein $R_f$ and $R_g$ are as described herein.

The term "heterocyclealkyl" as used herein, refers to a heterocycle, as defined herein, appended to the parent molecular moiety through an alkyl group, as defined herein. Representative examples of heterocyclealkyl include, but are not limited to, pyridin-3-ylmethyl and 2-pyrimidin-2-ylpropyl.

The term "heterocyclealkoxy" as used herein, refers to a heterocycle, as defined herein, appended to the parent molecular moiety through an alkoxy group, as defined herein.

The term "heterocycleoxy" as used herein, refers to a heterocycle, as defined herein, appended to the parent molecular moiety through an oxy group, as defined herein.

The term "heterocycleoxyalkyl" as used herein, refers to a heterocycleoxy, as defined herein, appended to the parent molecular moiety through an alkyl group, as defined herein.

The term "heterocycle-NH-" as used herein, refers to a heterocycle, as defined herein, appended to the parent molecular moiety through a nitrogen atom.

The term "heterocycle-NH-alkyl" as used herein, refers to a heterocycle-NH—, as defined herein, appended to the parent molecular moiety through an alkyl group, as defined herein.

The term "heterocyclecarbonyl" as used herein, refers to a heterocycle, as defined herein, appended to the parent molecular moiety through a carbonyl group, as defined herein. Representative examples of heterocyclecarbonyl include, but are not limited to, 1-piperidinylcarbonyl, 4-morpholinylcarbonyl, pyridin-3-ylcarbonyl and quinolin-3-ylcarbonyl.

The term "heterocyclesulfonyl" as used herein, refers to a heterocycle, as defined herein, appended to the parent molecular moiety through a sulfonyl group, as defined herein. Representative examples of heterocyclesulfonyl include, but are not limited to, 1-piperidinylsulfonyl, 4-morpholinylsulfonyl, pyridin-3-ylsulfonyl and quinolin-3-ylsulfonyl.

The term "hydroxy" as used herein, refers to an —OH group.

The term "hydroxyalkyl" as used herein, refers to a hydroxy group, as defined herein, appended to the parent molecular moiety through an alkyl group, as defined herein. Representative examples of hydroxyalkyl include, but are not limited to, hydroxymethyl, 2-hydroxyethyl, 3-hydroxypropyl and 2-ethyl-4-hydroxyheptyl.

The term "oxo" as used herein, refers to a =O group.

The term "oxy" as used herein, refers to a —O— group.

The term "sulfonyl" as used herein, refers to a —S(O)$_2$— group.

Salts

The present compounds may exist as therapeutically suitable salts. The term "therapeutically suitable salt," refers to salts or zwitterions of the compounds which are water or oil-soluble or dispersible, suitable for treatment of disorders without undue toxicity, irritation and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide the salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the present compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine and the like, are contemplated as being within the scope of the present invention.

Prodrugs

The present compounds may also exist as therapeutically suitable prodrugs. The term "therapeutically suitable prodrug," refers to those prodrugs or zwitterions which are suitable for use in contact with the tissues of patients without undue toxicity, irritation and allergic response, are commensurate with a reasonable benefit/risk ratio and are effective for their intended use. The term "prodrug," refers to compounds that are rapidly transformed in vivo to the parent compounds of formula (I-IXc) for example, by hydrolysis in blood. The term "prodrug," refers to compounds that contain, but are not limited to, substituents known as "therapeutically suitable esters." The term "therapeutically suitable ester," refers to alkoxycarbonyl groups appended to the parent molecule on an available carbon atom. More specifically, a "therapeutically suitable ester," refers to alkoxycarbonyl groups appended to the parent molecule on one or more available aryl, cycloalkyl and/or heterocycle groups as defined herein. Compounds containing therapeutically suitable esters are an example, but are not intended to limit the scope of compounds considered to be prodrugs. Examples of prodrug ester groups include pivaloyloxymethyl, acetoxymethyl, phthalidyl, indanyl and methoxymethyl, as well as other such groups known in the art. Other examples of prodrug ester groups are found in T. Higuchi and V. Stella, Pro-drugs as Novel Delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated herein by reference.

Optical Isomers-Diastereomers-Geometric Isomers

Asymmetric centers may exist in the present compounds. Individual stereoisomers of the compounds are prepared by synthesis from chiral starting materials or by preparation of racemic mixtures and separation by conversion to a mixture of diastereomers followed by separation or recrystallization, chromatographic techniques, or direct separation of the enantiomers on chiral chromatographic columns. Starting materials of particular stereochemistry are either commercially available or are made by the methods described hereinbelow and resolved by techniques well known in the art.

Geometric isomers may exist in the present compounds. The invention contemplates the various geometric isomers and mixtures thereof resulting from the disposal of substituents around a carbon-carbon double bond, a cycloalkyl group, or a heterocycloalkyl group. Substituents around a carbon-carbon double bond are designated as being of Z or E configuration and substituents around a cycloalkyl or heterocycloalkyl are designated as being of cis or trans configuration. Furthermore, the invention contemplates the various isomers and mixtures thereof resulting from the disposal of substituents around an adamantane ring system. Two substituents around a single ring within an adamantane ring system are designated as being of Z or E relative configuration. For examples, see C. D. Jones, M. Kaselj, R. N. Salvatore, W. J. le Noble J. Org. Chem. 63: 2758-2760, 1998.

The compounds and processes of the present invention will be better understood in connection with the following synthetic schemes and Experimentals that illustrate a means by which the compounds of the invention may be prepared.

The compounds of this invention may be prepared by a variety of procedures and synthetic routes. Representative procedures and synthetic routes are shown in, but are not limited to, Schemes 1-18.

Abbreviations which have been used in the descriptions of the Schemes and the Examples that follow are: Cbz for benzyloxycarbonyl; CbzCl for benzyloxycarbonyl chloride; DCE for 1,2-dichloroethane; DCM for dichloromethane; DMAP for dimethylaminopyridine; DME for 1,2-dimethoxyethane; DMF for N,N-dimethylformamide; DMSO for dimethylsulfoxide; DAST for (diethylamino)sulfur trifluoride; DIPEA for Hünig's base for diisopropylethylamine; DMPU for 1,3-dimethyl-3,4,5,6-tetrahydro-2(1H)-pyrimidinone; EDCI for (3-dimethylaminopropyl)-3-ethylcarbodiimide HCl; EtOAc for ethyl acetate; Et$_2$O for diethyl ether; EtOH for ethanol; HATU for O-(7-azabenzotriazol-1-yl)-N,N,N', N'-tetramethyluronium hexafluoro-phosphate; HOBt for hydroxybenzotriazole hydrate; iPrOH for isopropyl alcohol; KOTMS for potassium trimethylsilanolate; LAH for lithium aluminum hydride; MeOH for methanol; NMO for N-methylmorpholine N-oxide; NaOAC for sodium acetate; OXONE for potassium peroxymonosulfate; tBuOK for potassium tert-butoxide; TBTU for O-benzotriazol-1-yl-N,N,N',N'-tetramethyluronium tetrafluoroborate; THF for tetrahydrofuran; TosMIC for p-toluenesulfonylmethyl isocyanide; TPAP for tetrapropylammonium perruthenate; TFAA for trifluoroacetic anhydride; tosyl for para-toluene sulfonyl, mesyl for methane sulfonyl, and triflate for trifluoromethane sulfonyl.

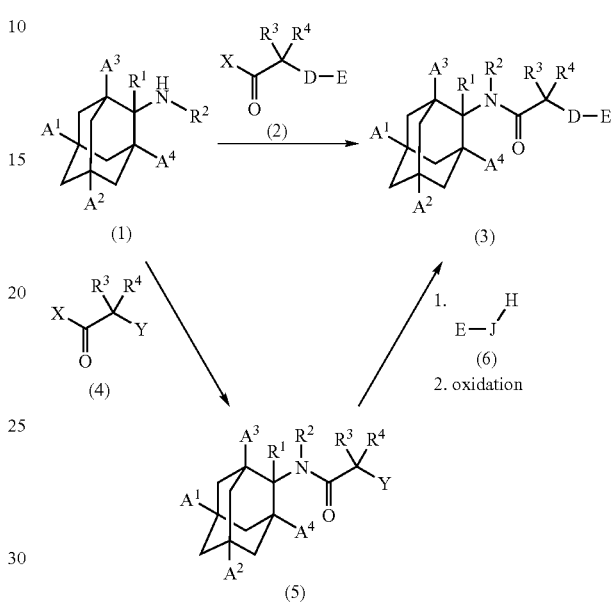

Scheme 1

Acids of general formula (2) wherein X=OH can be coupled to substituted adamantamines of general formula (1) with reagents such as EDCI and HOBt to provide amides of general formula (3). Substituted adamantanes of general formula (3), wherein A$^1$, A$^2$, A$^3$, A$^4$, R$^1$, R$^2$, R$^3$, R$^4$, D and E are as defined in formula I, may be prepared as in Scheme 1. Substituted adamantamines of general formula (1), purchased or prepared using methodology known to those in the art, may be treated with acylating agents of general formula (4), wherein X is chloro, bromo, or fluoro, Y is a leaving group such as Br (or a protected or masked leaving group) to provide amides of general formula (5). The substituted amides of general formula (5) may be treated with nucleophiles of general formula (6), wherein J is oxygen or sulfur and a base such as sodium hydride. When J is sulfur that reaction may be followed by oxidation with reagents like Oxone to provide amides of general formula (3) wherein D can become S(O) or S(O)$_2$. In some examples, A$^1$, A$^2$, A$^3$ and/or A$^4$ in amines of formula (1) may exist as a group further substituted with a protecting group such as a carboxylic acid protected as the methyl ester. Examples containing a protected functional group may be required due to the synthetic schemes and the reactivity of said groups and could be later removed to provide the desired compound. Such protecting groups can be removed using methodology known to those skilled in the art or as described in T. W. Greene, P. G. M. Wuts "Protective Groups in Organic Synthesis" 3$^{rd}$ ed. 1999, Wiley & Sons, Inc.

Scheme 2

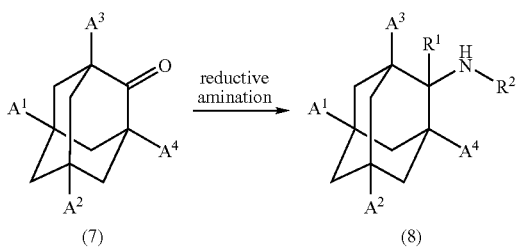

Substituted adamantane amines of general formula (8), wherein $A^1, A^2, A^3, A^4, R^1$ and $R^2$ are as defined in formula I, may be prepared as in Scheme 2. Substituted adamantane ketones of general formula (7) can be purchased or prepared using methodology known to those in the art. Ketones of general formula (7) can be treated with ammonia or primary amines ($R^2NH_2$) followed by reduction with reagents such as sodium borohydride or $H_2$ over Pd/C in a solvent like methanol to provide amines of general formula (8). In some examples, $A^1, A^2, A^3$ and/or $A^4$ in ketones of formula (7) may be a functional group substituted with a protecting group such as a carboxylic acid protected as the methyl ester. These protecting groups can be removed using methodology known to those in the art in amines of general formula (8) or in compounds subsequently prepared from ketones of general formula (7) or amines of general formula (8).

Scheme 3

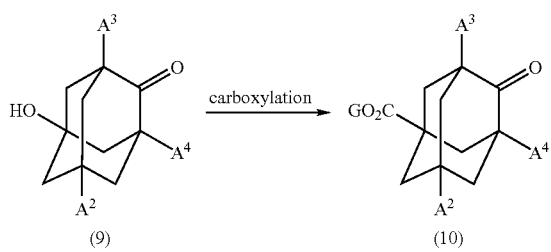

Substituted adamantanes of general formula (10), wherein $A^2, A^3$ and $A^4$ are as defined in formula I, may be prepared as in Scheme 3. Substituted adamantanes of general formula (9) can be purchased or prepared using methodology known to those skilled in the art. Adamantanes of general formula (9) can be treated with oleum and formic acid followed by an alcohol GOH, where G is an alkyl, cycloalkyl, hydrogen, aryl, or acid protecting group, to provide adamantanes of general formula (10). In some examples, G in formula (10) may be a protecting group such as methyl. These protecting groups can be removed using methodology known to those skilled in the art from adamantanes of general formula (10) or in compounds subsequently prepared from (10).

Scheme 4

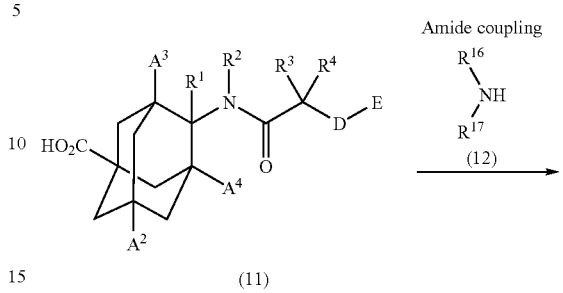

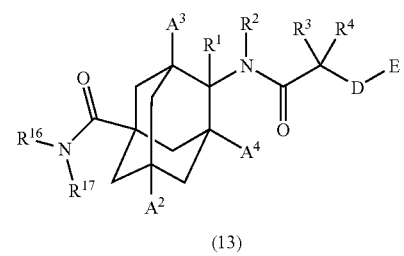

(13)

deprotection

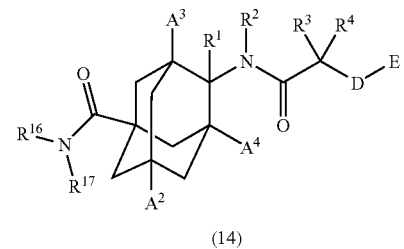

(14)

Substituted adamantanes of general formula (14), wherein $A^2, A^3, A^4, R^1, R^2, R^3, R^4, D, E, R^{16}$ and $R^{17}$ are as defined in formula I, may be prepared as in Scheme 4. Adamantyl acids of general formula (11) may be prepared as described herein or using methodology known to those skilled in the art. The acids of general formula (11) may be coupled with amines of general formula (12), wherein $R^{16}$ and $R^{17}$ are defined as in formula I, with reagents such as O-(benzotrialzol-1-yl)-1,1, 3,3-tetramethyluronium tetrafluoroborate (TBTU) to provide amides of general formula (13). In some examples, $A^2, A^3, A^4, R^1, R^2, R^3, R^{16}$ and $R^{17}$ in amines of formula (13) may contain a functional group substituted with a protecting group, for example, a carboxy protected as an ester. These protecting groups may be removed using methodology known to those in the art to provide amides of general formula (14).

Scheme 5

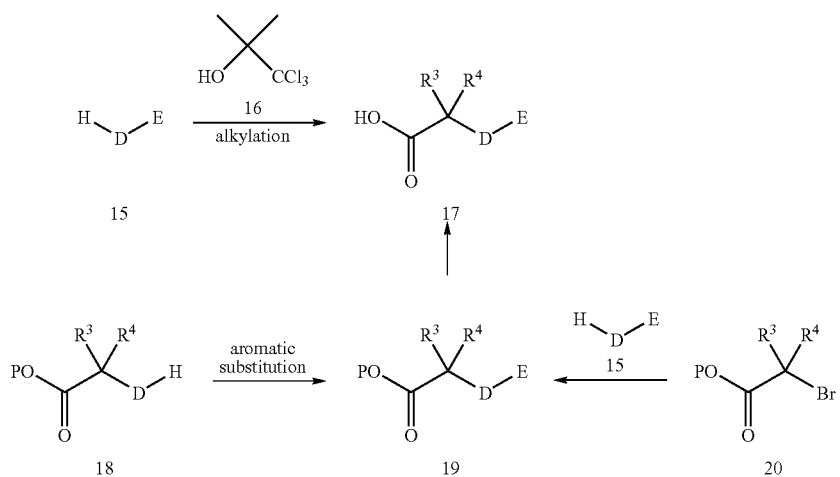

Acids of general formulas (17) wherein $R^3$, $R^4$, D and E are as defined in formula (I) can be prepared as shown in Scheme 5.

Phenols and thiols of general formula (15) wherein D is —O— or —S—, purchased or prepared using methodology known to those skilled in the art, may be treated with a reagent like 1,1,1-trichloro-2-methyl-propan-2-ol (16) in the presence of a base like sodium hydroxide in a solvent like acetone to provide acids of general formula (17).

Esters of general formula (18) wherein P is an acid protecting group such as, but not limited to, $C_1$-$C_6$ alkyl, aryl (substituted or unsubstituted) or arylalkyl (substituted or unsubstituted), may undergo an aromatic substitution or related reaction with halides of formula E-$X_1$ wherein $X_1$ is Cl, Br or I and E is as defined in formula (I), in the presence of a base like sodium hydride in a solvent like DMPU to afford compounds of formula (19). Removal of the acid protecting group, P, provides acids of formula (17). Cleavage of the acid protecting group can be conducted by either acidic or basic hydrolysis when P is $C_1$-$C_6$ alkyl, or hydrogenolysis when P is benzyl.

Alternatively, esters of general formula (18) may be coupled with halides of formula E-$X_1$ wherein $X_1$ is Cl, Br or I and E is aryl or heteroaryl, under with a metal catalyst like palladium along with ligands, to provide compounds of formula (19).

Compounds of formula (19) can also be obtained from the reaction of bromoesters of general formula (20), with compounds of formula (15) wherein D is —O— or —S— and E is defined as in formula (I), in the presence of a base such as, but not limited to, potassium carbonate, to provide esters of general formula (19).

Scheme 6

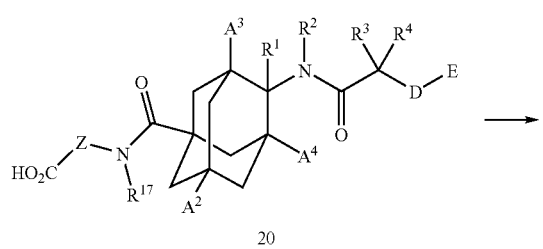

-continued

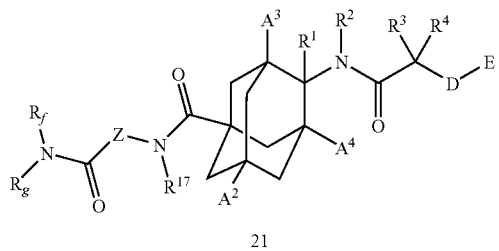

Substituted adamantane amides of general formula (21), wherein $R_f$ and $R_g$ are independently selected from the group consisting of hydrogen, alkyl, alkoxyalkyl, alkylsulfonyl, cycloalkyl, and cycloalkylalkyl wherein the cycloalkyl, the cycloalkyl of cycloalkylalkyl as represented by $R_f$ and $R_g$ are each independently unsubstituted or substituted with 1, 2 or 3 substituents independently selected from the group consisting of alkyl, halogen, and haloalkyl, Z is alkyl, aryl, heteroaryl, cycloalkyl, heterocycle, arylalkyl, heteroarylalkyl or heterocyclealkyl, and $A^2$, $A^3$, $A^4$, $R^1$, $R^2$, $R^3$, $R^4$, $R^{18}$, $R^2$, D and E are as defined in formula (I), can be prepared as shown in Scheme 6.

Adamantane acids of general formula (20) can be coupled with amines of formula $R_f R_g NH$, in the presence of a coupling agent such as, but not limited to, TBTU, and a base such as, but not limited, to diisopropylethylamine. The reaction is generally performed in a solvent such as, but not limited to, DMF, at a temperature of about room temperature to about 50° C. to provide amides of general formula (21).

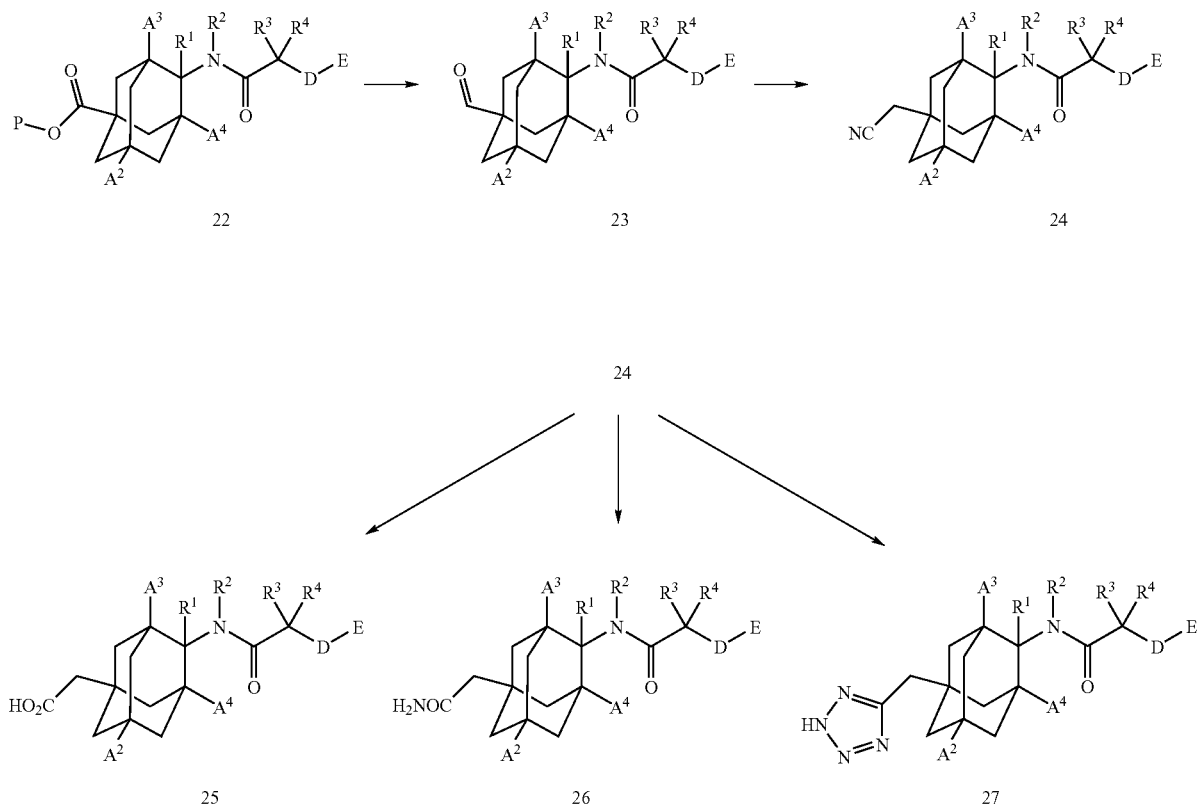

Substituted adamantanes of general formula (25), (26), and (27), wherein $A^2$, $A^3$, $A^4$, $R^1$, $R^2$, $R^3$, $R^4$, D and E are as defined in formula I, can be prepared as shown in Scheme 7.

Adamantanes of general formula (22) wherein P is hydrogen or an acid protecting group such as, but not limited to, $C_1$-$C_6$ alkyl, aryl (substituted or unsubstituted) or arylalkyl (substituted or unsubstituted), can be converted to aldehydes of formula (23) by (a) treatment with a reducing agent such as, but not limited to, lithium aluminum hydride, in a solvent like THF; and (b) treating the product from step (a) with an oxidizing agent such as, but not limited to, TPAP, in the presence of NMO, and in a solvent like dichloroethane.

Adamantane aldehydes of general formula (23) can be treated with TosMIC and a base like t-BuOK in a solvent mixture like DME and ethanol to provide nitriles of general formula (24). Nitriles of general formula (24) can be hydrolyzed with potassium hydroxide in a solvent like ethylene glycol to provide acids of general formula (25). When treated with hydrogen peroxide and sodium hydroxide in a solvent mixture like methanol and DMSO, nitriles of general formula (24) can be transformed to amides of formula (26).

Tetrazoles of formula (27) can be prepared from adamantanes of general formula (24) when treated with reagents like sodium azide and zinc bromide in a solvent like water and isopropanol.

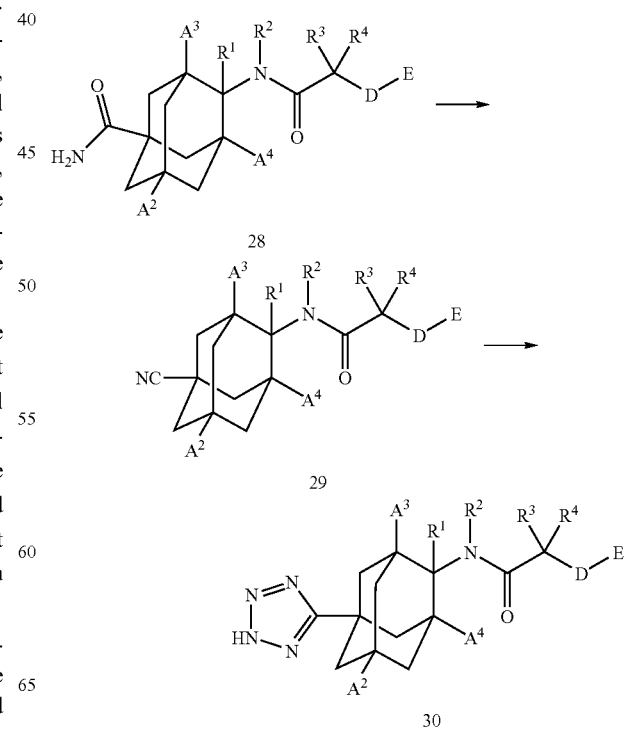

-continued

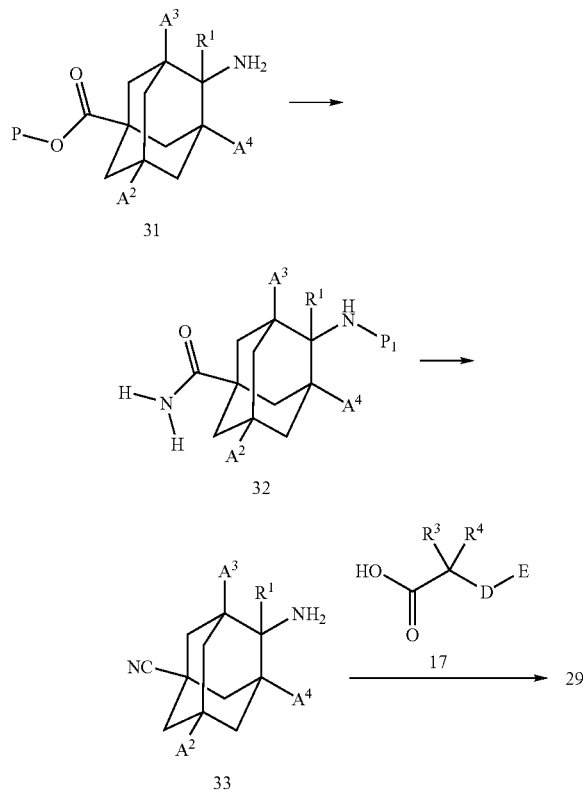

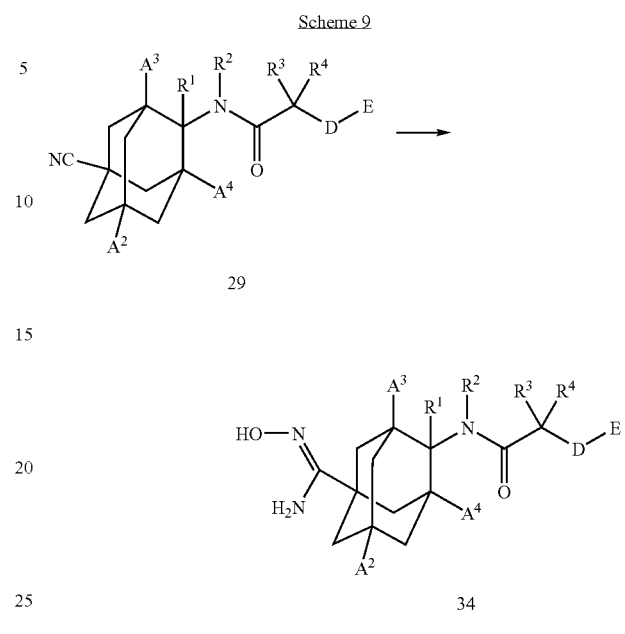

Substituted adamantanes of general formula (34), wherein $A^2, A^3, A^4, R^1, R^2, R^3, R^4$, D and E are as defined in formula I, can be prepared from treatment of compounds of formula (29) with hydroxylamine hydrochloride in a solvent like DMSO, in the presence of a base like diisopropylethylamine.

Substituted adamantanes of general formula (30), wherein $A^2, A^3, A^4, R^1, R^2, R^3, R^4$, D and E are as defined in formula (I), can be prepared as shown in Scheme 8.

Substituted adamantanes of general formula (28) can be dehydrated with a reagent like TBTU in the presence of a base like isopropylethylamine in a solvent like N,N-dimethylacetamide to provide nitriles of general formula (29). Nitriles of general formula (29) can be treated with reagents like trimethyl tin chloride and sodium azide in a solvent like toluene to provide tetrazoles of general formula (30).

Alternatively, adamantane amines of general formula (31) wherein P is hydrogen or $C_1$-$C_6$ alkyl, can be (a) treated with a reagent like CbzCl in a solvent like dichloromethane in the presence of a base like diisopropylethylamine; (b) treating the resulting product with a reagent like KOTMS in a solvent like THF; and (c) treating the acid from step (b) with ammonia or ammonium hydroxide in the presence of a reagent like EDCI and HOBt, and a base like diisopropylethylamine, in a solvent like DMF, to yield adamantane amides of general formula (32) wherein P is a protecting group like $-C(O)OCH_2C_6H_5$. The amides of general formula (32) can be (a) treated with a reagent like trifluoroacetic anhydride in a solvent like dichloromethane in the presence of a base like triethylamine; and (b) treating the intermediate from step (a) with a catalyst like $Pd(OH)_2$ on carbon under an atmosphere of hydrogen, to provide amines of formula (33). Amines of general formula (33) can be coupled to acids of general formula (17), in the presence of a reagent like HATU and a base like diisopropylethylamine, in a solvent like DMF, to provide compounds of general formula (29).

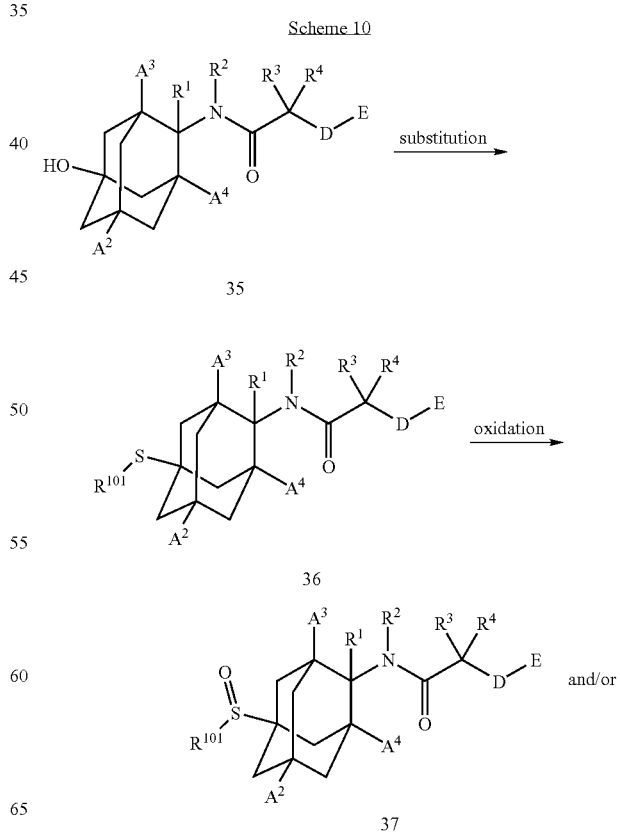

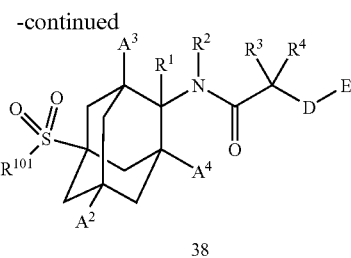

38

Substituted adamantanes of general formula (37) and (38), wherein $A^2, A^3, A^4, R^1, R^2, R^3, R^4$, D and E are as defined in formula I, and $R^{101}$ is alkyl, cycloalkyl, aryl, heteroaryl, or heterocycle, can be prepared as shown in Scheme 10.

Substituted adamantanes of general formula (35) can be (a) treated with trifluoroacetic anhydride in a solvent like trifluoroacetic acid; and (b) treating the product of step (a) with a thiol of formula $R^{101}SH$ at elevated temperature, typically at about 120° C. for a period of about 20 hours, in a solvent like trifluoroacetic acid to provide thioethers of general formula (36). Thioethers of general formula (36) can be oxidized with an oxidizing agent such as, but not limited to, 3-chloroperbenzoic acid, in a solvent such as, but not limited to, dichloromethane, to provide sulfoxides of general formula (37) and/or sulfones of general formula (38).

pyridine and in a solvent like dichloromethane provides the intermediate triflate that can be isolated. Treatment of the triflate with potassium thioacetate in a solvent like dimethylformamide yields adamantanes of general formula (40). Adamantane thioacetates of general formula (40), when treated with an oxidizing agent such as, but not limited to, hydrogen peroxide and a base like sodium acetate in a solvent like acetic acid provides sulfonic acids of general formula (41).

Sulfonic acids of general formula (41) can be coupled with an amine of formula $R^{25}R^{26}NH$ wherein $R^{25}$ and $R^{26}$ are defined as in formula I to provide compounds of formula (42). Numerous reaction conditions for such a conversion are known to one skilled in the art. One such coupling utilizes triphosgene in the presence of a base like triethylamine with a catalytic amount of dimethylformamide in a solvent like dichloromethane, followed by the addition an amine of formula $R^{25}R^{26}NH$.

Compounds of formula (42) wherein $R^{25}$ is as defined in formula (I) other than hydrogen and $R^{26}$ is hydrogen, or $R^{25}$ and $R^{26}$ are as defined in formula (I) other than hydrogen, can also be obtained from the mono or dialkylation of compounds of formula (42) wherein $R^{25}$ and $R^{26}$ are hydrogen.

The mono alkylation can be facilitated with an alkylating reagent of formula $R^{25}X_1$ wherein $R^{25}$ is methyl, benzyl, and allyl, and $X_1$ is a leaving group such as, but not limited to, Cl, Br, I, triflate or tosylate. The reaction is generally conducted in the presence of a base such as, but not limited to, alkali Scheme 11

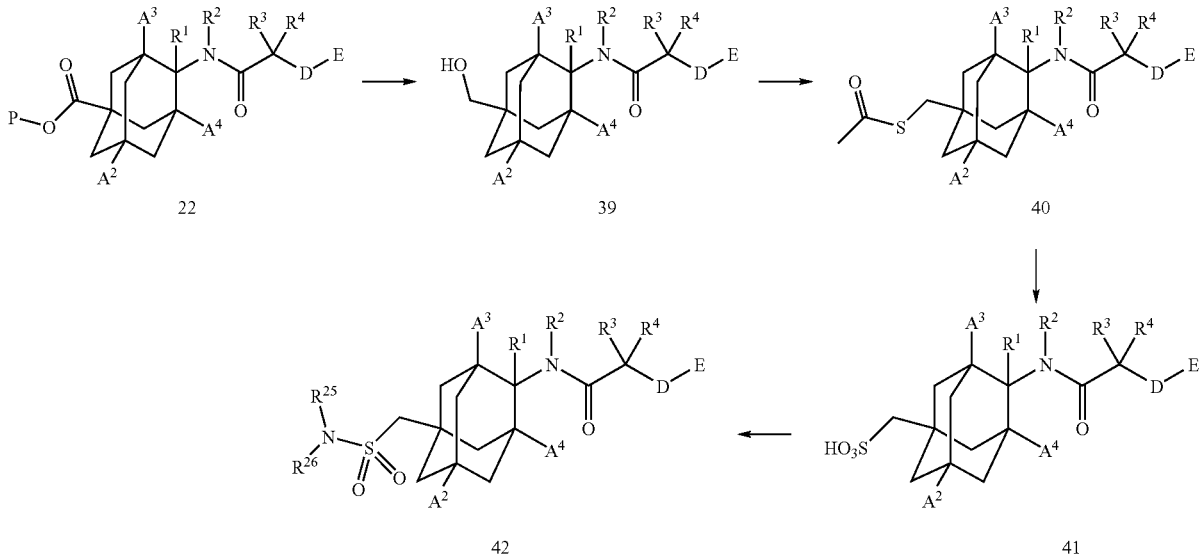

Substituted adamantanes of general formula (42), wherein $A^2, A^3, A^4, R^1, R^2, R^3, R^4, R^{25}, R^{26}$, D and E are as defined in formula (I), can be prepared as shown in Scheme 11.

Substituted adamantanes of general formula (22) wherein P is hydrogen or an acid protecting group such as, but not limited to, $C_1$-$C_6$ alkyl, aryl (substituted or unsubstituted) or arylalkyl (substituted or unsubstituted), can be converted alcohols of formula (39) by treatment with a reducing agent such as, but not limited to, lithium aluminum hydride or diisobutylaluminum hydride in a solvent like THF. Reaction of the alcohols of general formula (39) with trifluoromethanesulfonic anhydride in the presence of a base like metal carbonates (for example, cesium carbonate and the like), in a solvent such as, but not limited to, DMF, providing compounds of formula (42) wherein $R^{25}$ is methyl, benzyl, and allyl, and $R^{26}$ is hydrogen. Further alkylation with $R^{26}X_1$ wherein $R^{26}$ is methyl, benzyl, and allyl and $X_1$ as defined above, using the aforementioned reaction condition, affords compounds of formula (42) wherein $R^{25}$ and $R^{26}$ are independently selected from the group consisting of methyl, benzyl, and allyl. The reaction can be conducted stepwise or in situ without isolating the product of the monoalkylation.

Alternatively, compounds of formula (42) wherein $R^{25}$ and $R^{26}$ are identical and are as defined in formula (I) other than hydrogen, can be prepared from the reaction of compounds of formula (42) wherein $R^{25}$ and $R^{26}$ are hydrogen and about two equivalents of the alkylating agent.

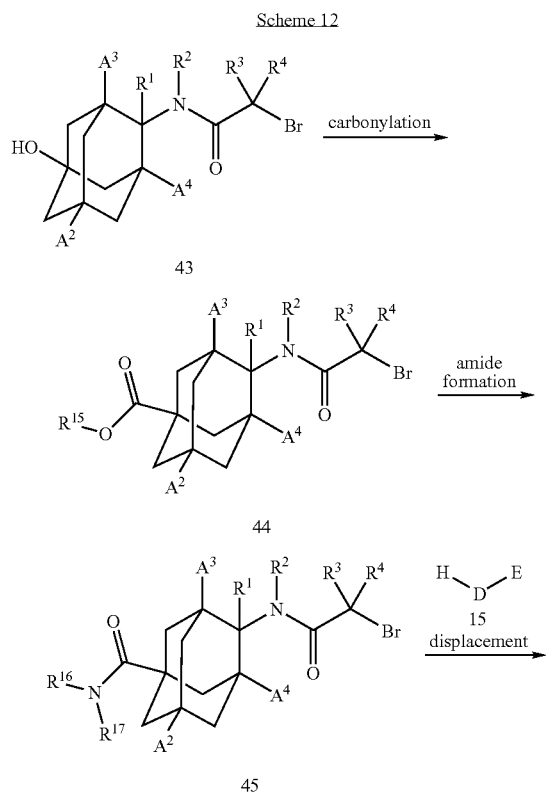

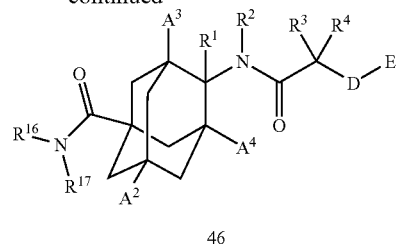

Substituted adamantanes of general formula (46), wherein $A^2, A^3, A^4, R^1, R^2, R^3, R^4, R^{16}R^{17}$, D and E are as defined in formula (I) can be prepared as shown in Scheme 12.

Substituted adamantanes of general formula (43) can be carbonylated with formic acid and oleum and poured into a solution of formula $R^{15}OH$ to provide an adamantane of general formula (44) wherein $R^{15}$ is as defined in formula (I). Adamantanes of general formula (44) wherein $R^{15}$ is not hydrogen can be converted to adamantanes of formula (44) wherein $R^{15}$ is hydrogen using methodologies listed in T. W. Greene, P. G. M. Wuts "Protective Groups in Organic Synthesis" $3^{rd}$ ed. 1999, Wiley & Sons, Inc. The resulting acids can be coupled to amines of general formula $R^{16}R^{17}NH$ to provide amides of formula (45) in the presence of coupling reagents such as, but not limited to, EDCI and HOBt in a solvent like dichloromethane. Adamantanes of general formula (45) may be treated with alcohols or thiols of general formula (15) wherein D is —O— or —S— and E is defined as in formula (I), in the presence of a base like potassium carbonate in a solvent like toluene to provide adamantanes of general formula (46).

Adamantanes of general formula (46) wherein D is —S— can be converted to compounds of formula (46) wherein D is —S(O)— or —S(O)$_2$— by reacting with an oxidizing agent such as, but not limited to, oxone in a solvent like methanol.

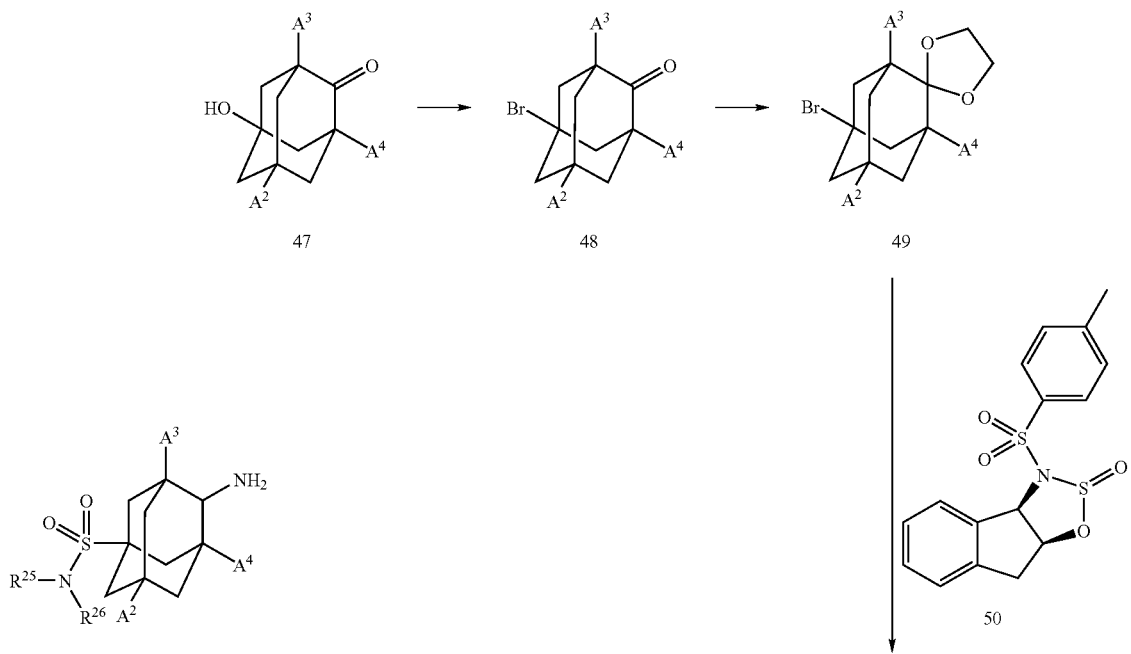

-continued

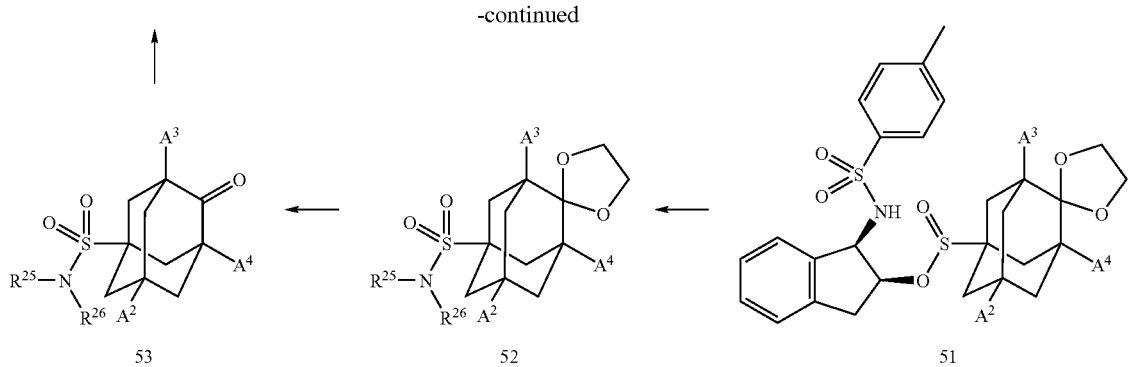

Substituted adamantanes of general formula (54), wherein $A^2, A^3, A^4, R^{25}$ and $R^{26}$ are as defined in formula I, may be prepared as shown in Scheme 13.

Substituted adamantanes of general formula (47) can be brominated with a reagent like hydrobromic acid in a solvent like water to provide bromides of general formula (48). Adamantanes of general formula (48) when treated with ethylene glycol and a catalytic amount of an acid like p-toluenesulfonic acid in a solvent like benzene provide adamantanes of general formula (49). Bromides of general formula (49) can be (a) treated with Rieke zinc in a solvent like tetrahydrofuran; and (b) followed by treatment with reagent (50) (prepared as described in Han, Z.; Krishnamurthy, D.; Grover, P.; Fang, Q. K.; Senanayake, C. H. *J. Am. Chem. Soc.* 2002, 124, 7880-7881) in a solvent like tetrahydrofuran to provide adamantanes of general formula (51). Adamantanes of general formula (51) may be treated with lithium amide of formula $LiNHR^{25}R^{26}$ (prepared in situ by reacting ammonia with lithium or amines of formula $R^{25}R^{26}NH$ wherein $R^{25}$ and $R^{26}$ are other than hydrogen, with t-butyl lithium) in a solvent mixture like ammonia and tetrahydrofuran. The resulting sulfinamides can be oxidized with a reagent like osmium tetroxide with a catalyst oxidant like NMO in a solvent like tetrahydrofuran to provide sulfonamides of general formula (52). Adamantanes of general formula (52) can be deketalized with reagents like hydrochloric acid in a solvent like water and tetrahydrofuran to provide ketones of formula (53). Ketones of formula (53) can be treated with amines of formula $R^{25}R^{26}NH$ followed by reduction with reducing reagents such as, but not limited to, sodium borohydride or hydrogen over Pd/C in a solvent like methanol to provide amines of general formula (54).

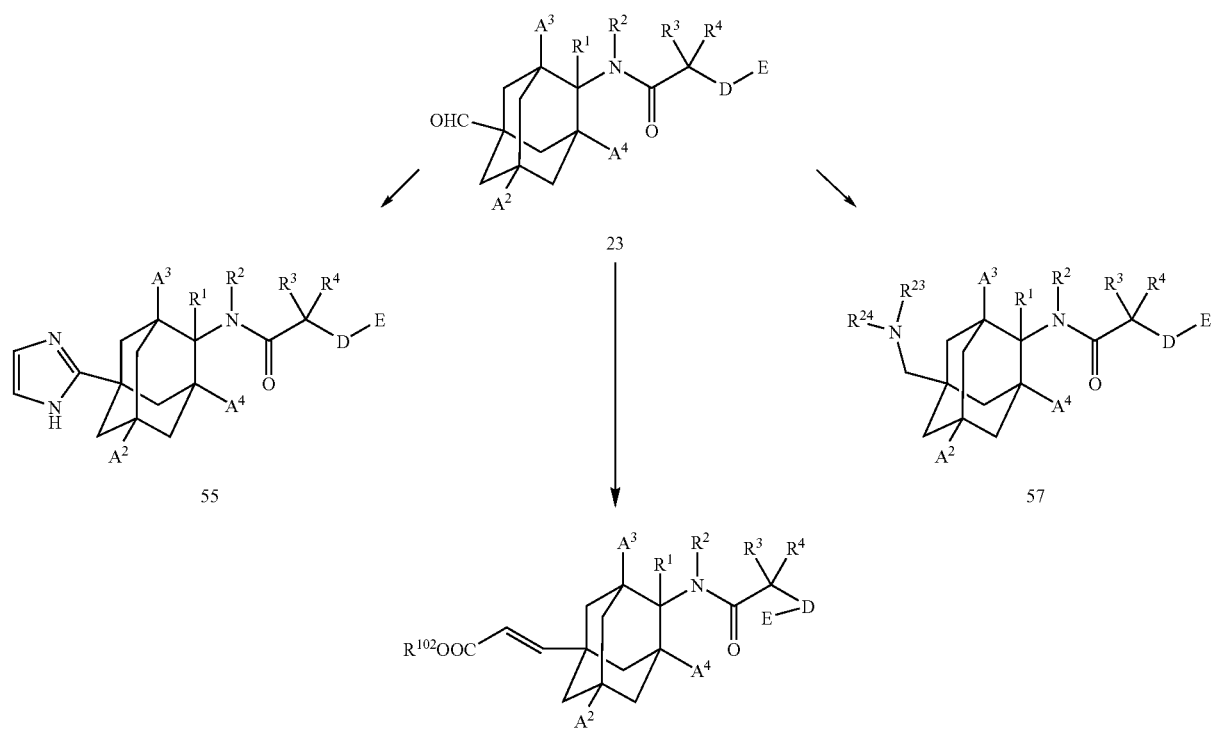

Substituted adamantanes of general formula (55), (56) and (57) wherein $R^{102}$ is hydrogen, alkyl or aryl, and $A^2$, $A^3$, $A^4$, $R^1$, $R^2$, $R^3$, $R^4$, $R^{23}$, $R^{24}$, D and E are as defined in formula (I), can be prepared as shown in Scheme 14.

Substituted adamantanes of general formula (23) can be treated with reagents like ammonia and glyoxal in a solvent like water to provide imidazoles of general formula (55).

Reaction of compounds of formula (23) with Wittig reagent such as, but not limited to, triethyl phosphonoacetate and a base like sodium hydride in a solvent like dimethoxyethane provides esters of general formula (56) wherein $R^{102}$ is alkyl or aryl. Esters of general formula (56) can be cleaved with lithium hydroxide in a solvent mixture like tetrahydrofuran and water to provide acids of general formula (56) wherein $R^{102}$ is hydrogen.

Adamantanes of general formula (23) can be reductively aminated with amines of general formula $R^{23}R^{24}NH$ with a reagent like sodium triacetoxyborohydride in the presence of an acid like acetic acid in a solvent like dichloroethane to yield amines of general formula (57).

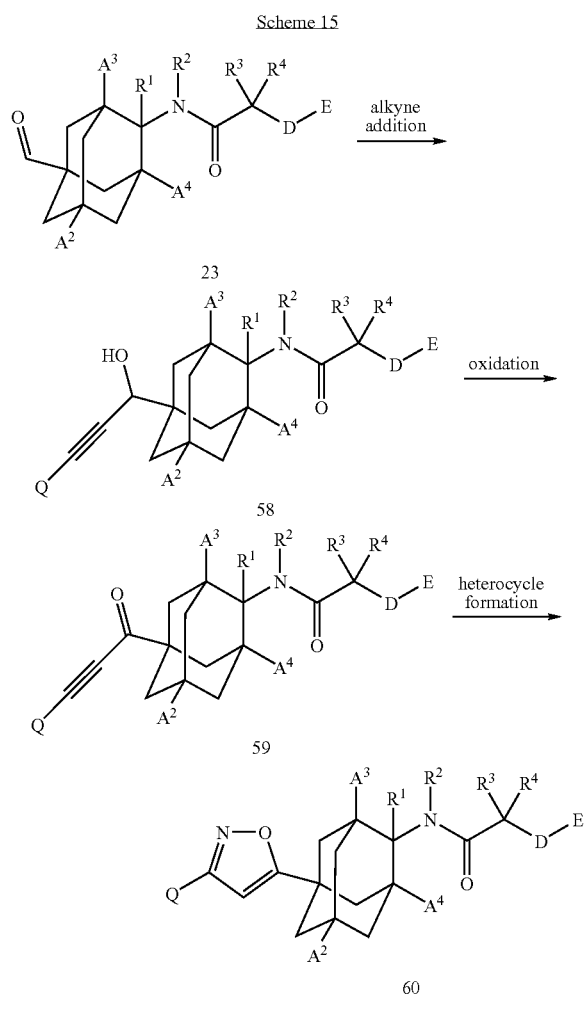

Scheme 15

Substituted adamantanes of general formula (60), wherein $A^2$, $A^3$, $A^4$, $R^1$, $R^2$, $R^3$, $R^4$, D and E are as defined in formula I and Q is hydrogen, alkyl, or cycloalkyl, can be prepared as shown in Scheme 15.

Substituted adamantanes of general formula (23) can be treated with a reagent like acetylenemagnesium chloride in a solvent like THF to yield alcohols of general formula (58). Adamantane alcohols of general formula (58) can be oxidized with a reagent like Dess-Martin periodinane in a solvent like dichloromethane to provide alkynones of general formula (59). Alkynones of general formula (59) can be reacted with a reagent like hydroxylamine hydrochloride in the presence of a base like potassium carbonate in a solvent like isopropanol to provide heterocycles of general formula (60).

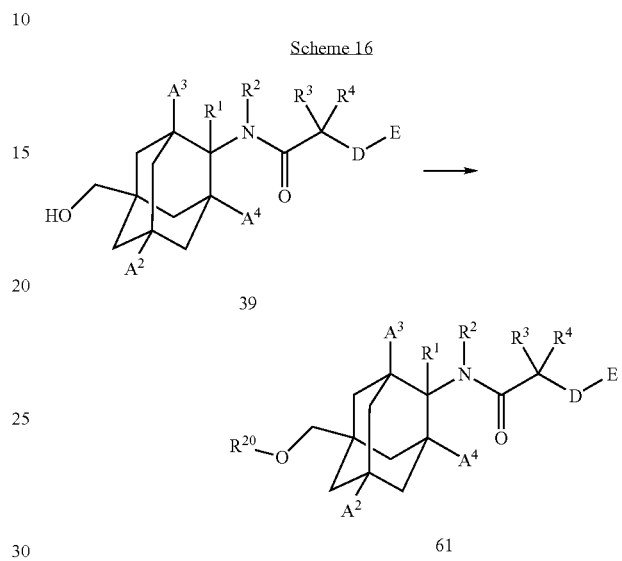

Scheme 16

Substituted adamantanes of general formula (61), wherein $A^2$, $A^3$, $A^4$, $R^1$, $R^2$, $R^3$, $R^4$, $R^{20}$, D and E are as defined in formula (I), can be prepared as shown in Scheme 16.

Adamantanes of general formula (39) can be alkylated with a reagent of formula $R^{20}X_1$, wherein $X_1$ is a halide or other leaving group like bromide, iodide, tosylate or triflate, in the presence of a base like sodium hydride in a solvent like dimethylformamide to yield ethers of general formula (61).

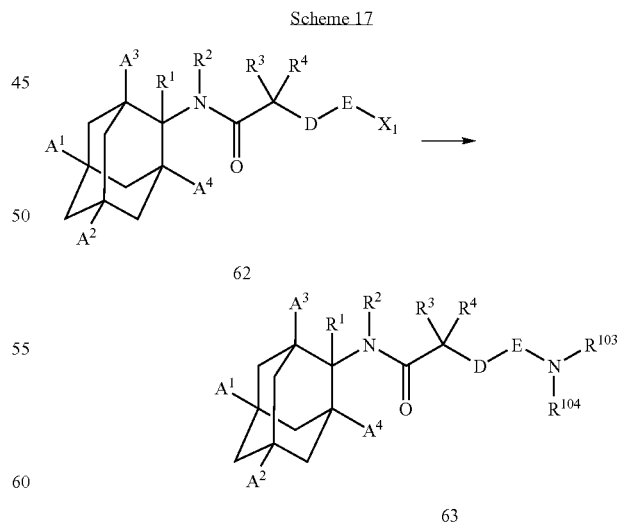

Scheme 17

Substituted adamantanes of general formula (63), wherein E is aryl or heteroaryl and $A^1$, $A^2$, $A^3$, $A^4$, $R^1$, $R^2$, $R^3$, $R^4$, and D are as defined in formula (I) and $R^{103}$ and $R^{104}$ are alkyl, alkoxyalkyl, cycloalkyl, aryl, heteroaryl, heterocycle, heteroaryl, heteroarylalkyl, cycloalkylalkyl, arylalkyl, heteroarylalkyl, or heterocyclealkyl, or $R^{103}$ and $R^{104}$ combined to the atom to which they are attached form a heterocycle or heteroaryl can be prepared as shown in Scheme 17.

Substituted adamantanes of general formula (62) wherein $X_1$ is a halide or triflate can be coupled with amines of formula $NHR^{103}R^{104}$ with a reagent combination like copper iodide and N,N-dimethylglycine in a solvent like DMSO under microwave heating to provide adamantanes of general formula (63).

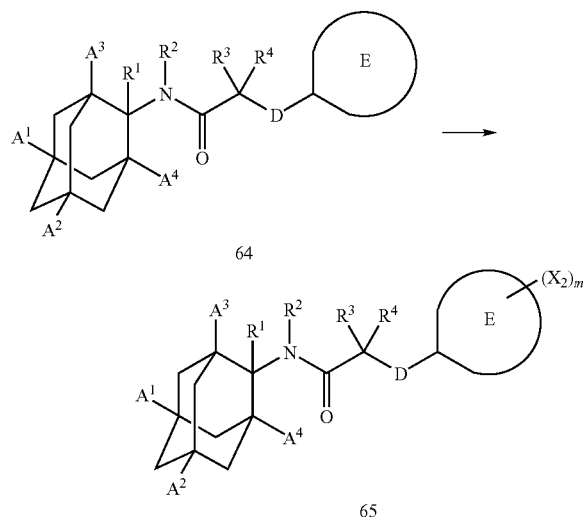

Scheme 18

Substituted adamantanes of general formula (65), wherein m is 1 or 2, $A^1$, $A^2$, $A^3$, $A^4$, $R^1$, $R^2$, $R^3$, $R^4$ and D are as defined in formula (I), E is aryl or heteroaryl, and $X_2$ is halogen, can be prepared as shown in Scheme 18.

Adamantanes of general formula (64) can be halogenated with a reagent like N-bromosuccinimide in the presence of an acid like HBr in a solvent like dichloromethane to yield aryl halides of general formula (65).

It is understood that the schemes described herein are for illustrative purposes and that routine experimentation, including appropriate manipulation of the sequence of the synthetic route, protection of any chemical functionality that are not compatible with the reaction conditions and deprotection are included in the scope of the invention. Protection and Deprotection of carboxylic acids and amines are known to one skilled in the art and references can be found in "Protective Groups in Organic Synthesis", T. W. Greene, P. G. M. Wuts, 3rd edition, 1999, Wiley & Sons, Inc.

The compounds and processes of the present invention will be better understood by reference to the following Examples, which are intended as an illustration of and not a limitation upon the scope of the invention. Further, all citations herein are incorporated by reference.

Compounds of the invention were named by ACD/ChemSketch version 5.01 (developed by Advanced Chemistry Development, Inc., Toronto, ON, Canada) or were given names consistent with ACD nomenclature. Adamantane ring system isomers were named according to common conventions. Two substituents around a single ring within an adamantane ring system are designated as being of Z or E relative configuration (for examples see C. D. Jones, M. Kaselj, R. N. Salvatore, W. J. le Noble J. Org. Chem. 63: 2758-2760, 1998).

EXAMPLE 1

E-4-(2-methyl-2-phenoxy-propionylamino)-adamantane-1-carboxylic Acid Amide

EXAMPLE 1A

E- and Z-5-hydroxy-2-adamantamine

A solution of 5-hydroxy-2-adamantanone (10 g, 60.161 mmoles) and 4 Å molecular sieves (5 g) in methanolic ammonia (7N, 100 mL) was stirred overnight at room temperature. The mixture was cooled in an ice bath, treated by the portionwise addition of sodium borohydride (9.1 g, 240.64 mmoles) and stirred at room temperature for 2 hours. The mixture was filtered and MeOH was removed under reduced pressure. The mixture was taken into DCM (100 mL), acidified with 1N HCl to pH=3 and the layers separated. The aqueous layer was treated with 2N NaOH solution to pH=12 and extracted three times with 4:1 THF:DCM. The combined organic extracts were dried (MgSO$_4$) and filtered. The filtrate was concentrated under reduced pressure to provide the title compound as a white solid (9.84 g, 97.9%).

EXAMPLE 1B

E-2-bromo-N-(5-hydroxy-adamantan-2-yl)-2-methyl-propionamide

A solution of E- and Z-5-hydroxy-2-adamantamine (0.868 g, 5.2 mmoles) in DCM (15.0 mL) and DIPEA (2.5 mL) was cooled in an ice bath and treated with 2-bromoisobutyryl bromide (0.72 mL, 5.8 mmoles) in DCM (2.5 mL). The mixture was stirred for 2 hours at room temperature and DCM was removed under reduced pressure. The residue was partitioned between water and ethyl acetate. The organic layer was washed with saturated sodium bicarbonate, water, dried (MgSO$_4$) and filtered. The filtrate was concentrated under reduced pressure to provide the title compound as dark beige solid (1.17 g, 71%). The isomers were separated by column chromatography (silica gel, 5-35% acetone in hexane) to furnish 0.78 g of E-2-bromo-N-(5-hydroxy-adamantan-2-yl)-2-methyl-propionamide and 0.39 g of Z-2-bromo-N-(5-hydroxy-adamantan-2-yl)-2-methyl-propionamide.

EXAMPLE 1C

E-4-(2-bromo-2-methyl-propionylamino)-adamantane-1-carboxylic Acid Methyl Ester

A solution of E-2-bromo-N-(5-hydroxy-adamantan-2-yl)-2-methyl-propionamide (0.78 g, 2.48 mmol) in 99% formic acid (2.5 mL) was added dropwise with vigorous gas evolution over 10 minutes to a rapidly stirred 30% oleum solution (7.5 mL) heated to 60° C. (W. J. le Noble, S. Srivastava, C. K. Cheung, J. Org. Chem. 48: 1099-1101, 1983). Upon completion of addition, more 99% formic acid (2.5 mL) was slowly added over the next 10 minutes. The mixture was stirred another 60 minutes at 60° C. and then slowly poured into vigorously stirred iced water (30.0 mL) cooled to 0° C. The mixture was allowed to slowly warm to 23° C., filtered and washed with water to neutral pH (100 mL). The precipitate was dried in a vacuum oven, taken into MeOH and treated with thionyl chloride at 0° C. (0.2 mL, 2.8 mmoles). The reaction mixture was stirred at room temperature for 3 hours and then MeOH was evaporated under reduced pressure to provide the title compound as an off-white solid.

EXAMPLE 1D

E-4-(2-methyl-2-phenoxy-propionylamino)-adamantane-1-carboxylic Acid

Step A

A solution of phenol (20.7 mg, 0.22 mmoles) and sodium hydride (60%, 10.8 mg, 0.27 mmoles) in toluene (2 mL) was stirred at room temperature for 1 hour. Then E-4-(2-bromo-2-methyl-propionylamino)-adamantane-1-carboxylic acid methyl ester (71.6 mg, 0.2 mmoles) was added and the resulting mixture was shaken at 100° C. for 48 hours. After that the reaction mixture was cooled and filtered. The filtrate was concentrated under reduced pressure to provide crude methyl ester of the title compound that was purified on reverse phase HPLC.

Step B

The methyl ester of the title compound obtained from step A was hydrolyzed with 2N aqueous NaOH, THF and ethanol (2:1:1, 2 mL) at room temperature overnight. The reaction mixture was acidified with 1N HCl and extracted with ethyl acetate. The organic layer was separated, washed with water and brine respectively, dried ($MgSO_4$) and filtered. The filtrate was concentrated under reduced pressure to provide the title compound.

EXAMPLE 1E

E-4-(2-methyl-2-phenoxy-propionylamino)-adamantane-1-carboxylic Acid Amide

A solution of E-4-(2-methyl-2-phenoxy-propionylamino)-adamantane-1-carboxylic acid (23 mg, 0.064 mmoles) in DCM (2 mL) was treated with HOBt (9.5 mg, 0.07 mmoles) and EDCI (14.7 mg, 0.077 mmoles) and stirred at room temperature for 1 hour. Excess of aqueous (30%) ammonia (2 mL) was added and the reaction was stirred for additional 20 hours. The layers were separated and the aqueous layer extracted twice more with methylene chloride (2×2 mL). The combined organic extracts were washed with water (3×2 mL), brine (2 mL), dried ($MgSO_4$) and filtered. The filtrate was concentrated under reduced pressure to provide the crude title compound that was purified on reverse phase HPLC to provide the title compound. $^1$H NMR (500 MHz, DMSO-D6) δ ppm 7.26-7.31 (m, 2H) 7.25 (d, J=7.49 Hz, 1H) 7.02 (t, J=7.33 Hz, 1H) 6.95 (s, 1H) 6.91 (d, J=7.80 Hz, 2H) 6.68 (s, 1H) 3.79-3.88 (m, 1H) 1.91 (s, 2H) 1.76-1.87 (m, 5H) 1.71 (s, 2H) 1.65 (d, J=12.79 Hz, 2H) 1.45 (s, 6H) 1.38 (d, J=12.79 Hz, 2H). MS (ESI+) m/z 357 (M+H)$^+$.

EXAMPLE 2

E-4-[2-methyl-2-(4-(trifluoromethyl-benzyloxy)-propionylamino]-adamantane-1-carboxylic Acid Amide The title compound was prepared according to the procedure outlined in Example 1D and 1E substituting 4-(trifluoromethyl)benzyl alcohol for phenol. $^1$H NMR (500 MHz, DMSO-D6) δ ppm 7.73 (d, J=8.11 Hz, 2H) 7.62 (d, J=8.11 Hz, 2H) 7.07 (d, J=7.49 Hz, 1H) 6.95 (s, 1H) 6.68 (s, 1H) 4.60 (s, 2H) 3.78 (d, J=7.49 Hz, 1H) 1.88 (s, 2H) 1.76-1.85 (m, 5H) 1.72 (s, 2H) 1.59 (d, J=13.10 Hz, 2H) 1.39-1.44 (m, 8H). MS (ESI+) m/z 439 (M+H)$^+$

EXAMPLE 3

E-4-[2-methyl-2-(2-methyl-cyclohexyloxy)-propionylamino]-adamantane-1-carboxylic Acid A two phase suspension of E-4-(2-bromo-2-methyl-propionylamino)-adamantane-1-carboxylic acid methyl ester (71.6 mg, 0.2 mmoles), 2-methylcyclohexanol (0.033 mL, 0.24 mmoles) and tetrabutylammonium bromide (6 mg, 0.02 mmoles) in DCM (1.0 mL) and 50% aqueous NaOH (1.0 mL) was stirred at room temperature for 20 hours. After that the reaction mixture was diluted with DCM, neutralized with 3N HCl and layers separated. Organic layer was washed with water (3×2 mL), dried ($MgSO_4$) and filtered. The filtrate was concentrated under reduced pressure to provide crude methyl ester of the title compound that was purified on reverse phase HPLC and hydrolyzed with 2N aqueous NaOH, THF and ethanol (2:1:1, 2 mL) at room temperature for 20 hours. The reaction mixture was acidified with 1N HCl and extracted with ethyl acetate. The organic layer was separated, washed with water and brine respectively, dried ($MgSO_4$) and filtered. The filtrate was concentrated under reduced pressure to provide the title compound. $^1$H NMR (400 MHz, DMSO-D6) δ ppm 11.77-12.49 (m, 1H) 7.27 (d, J=7.98 Hz, 1H) 3.76 (d, J=6.75 Hz, 1H) 3.19-3.28 (m, 1H) 0.98-1.96 (m, 28H) 0.85-0.96 (m, 3H) MS (ESI+) m/z 378 (M+H)$^+$

EXAMPLE 4

E-4-[2-methyl-2-(3-methyl-cyclohexyloxy)-propionylamino]-adamantane-1-carboxylic Acid The title compound was prepared according to the procedure outlined in Example 3 substituting 3-methylcyclohexanol for 2-methylcyclohexanol. $^1$H NMR (400 MHz, DMSO-D6) δ ppm 11.70-12.38 (m, 1H) 7.16 (d, J=7.36 Hz, 1H) 3.76 (s, 1H) 3.41-3.53 (m, 1H) 1.33-1.96 (m, 18H) 1.05-1.31 (m, 8H) 0.66-0.99 (m, 5H). MS (ESI+) m/z 378 (M+H)$^+$

EXAMPLE 5

E-4-(2-cycloheptyloxy-2-methyl-propionylamino)-adamantane-1-carboxylic Acid

The title compound was prepared according to the procedure outlined in Example 3 substituting cycloheptanol for 2-methylcyclohexanol. $^1$H NMR (400 MHz, DMSO-D6) δ ppm 11.85-12.35 (m, 1H) 7.21 (d, J=7.67 Hz, 1H) 3.70-3.88 (m, 2H) 1.37-1.96 (m, 25H) 1.27 (s, 6H). MS (ESI+) m/z 378 (M+H)$^+$

EXAMPLE 6

E-4-(2-(cyclohexylmethoxy-2-methyl-propionylamino)-adamantane-1-carboxylic Acid

The title compound was prepared according to the procedure outlined in Example 3 substituting cyclohexylmethanol for 2-methylcyclohexanol. $^1$H NMR (400 MHz, DMSO-D6) δ ppm 11.70-12.50 (m, 1H) 7.06 (d, J=7.36 Hz, 1H) 3.76 (d, J=7.98 Hz, 1H) 3.19 (d, J=6.14 Hz, 2H) 1.41-1.95 (m, 19H) 1.26 (s, 6H) 0.90-1.25 (m, 5H). MS (ESI+) m/z 378 (M+H)$^+$

EXAMPLE 7

E-4-[2-(4-chloro-phenoxy)-2-methyl-propionylamino]-adamantane-1-carboxylic Acid

EXAMPLE 7A

E-4-Amino-adamantane-1-carboxylic Acid

To 1.0 g (10 wt %) of 5% Pd/C is added 4-oxo-adamantane-1-carboxylic acid (10.0 g, 51.5 mmol) followed by 7M $NH_3$ in MeOH (200 mL). The reaction mixture is stirred under an atmosphere of $H_2$ at 23° C. for 16-24 hours; water (200 mL) is added; and the catalyst is removed by filtration. The catalyst is washed with methanol and the filtrate solution is concentrated under reduced pressure at a bath temperature of 35° C. until solvent stops coming over. Approximately 150 mL of a slurry remains. Acetonitrile (300 mL) is added to the slurry which is then stirred for 3 hours at 23° C. The slurry is filtered and washed once with acetonitrile (100 mL). The wet cake is dried at 50° C. and 20 mmHg under $N_2$ to yield E-4-amino-adamantane-1-carboxylic acid (8.65 g, 86%, 13.1:1.0 E:Z ratio by $^1$H-NMR in $D_2O$).

EXAMPLE 7B

E-4-Amino-adamantane-1-carboxylic Acid Methyl Ester

Methanol (85 mL) was cooled to 0° C.; acetyl chloride (15.5 mL) was added dropwise; and then the solution was warmed to 23° C. for 15-20 minutes. E-4-Amino-adamantane-1-carboxylic acid (8.53 g, 43.7 mmol) was added and the reaction solution was heated to 45° C. for 16 hours. The reaction solution was cooled to 23° C. and acetonitrile (85 mL) was added. The reaction solution was concentrated under reduced pressure to ~1/4 volume. The reaction solution was further chase distilled with acetonitrile (2×85 mL). The resulting suspension was cooled to 23° C. and filtered. The filtrate was recirculated twice to wash the wet cake. The product was dried at 50° C., 20 mmHg for 16 hours to afford E-4-amino-adamantane-1-carboxylic acid methyl ester as a white crystalline solid (10.02 g, 93%).

EXAMPLE 7C

E-4-[2-(4-chloro-phenoxy)-2-methyl-propionylamino]-adamantane-1-carboxylic Acid

To the solution of E-4-Adamantamine-1-carboxylic acid methyl ester (49 mg, 0.2 mmoles) and triethylamine (0.097 mL, 0.7 mmoles) in DCM (1.0 mL) was added a solution of 2-(4-chlorophenoxy)-2-methylpropionyl chloride (55 mg, 0.24 mmoles) in DCM (1.0 mL). The resulting reaction mixture was stirred at room temperature for 20 hours and concentrated under reduced pressure. The residue was partitioned between ethylacetate and water. The organic layer was separated and washed with 1N HCl, water and brine, dried (MgSO4) and filtered. The filtrate was concentrated under reduced pressure to provide the crude methyl ester of the title compound that was purified on reverse phase HPLC and hydrolyzed with 2N aqueous NaOH, THF and ethanol (2:1:1, 2 mL) at room temperature for 20 hours. The reaction mixture was acidified with 1N HCl and extracted with ethyl acetate. The organic layer was separated, washed with water and brine respectively, dried (MgSO$_4$) and filtered. The filtrate was concentrated under reduced pressure to provide the title compound. $^1$H NMR (500 MHz, DMSO-D6) δ ppm 11.94-12.25 (m, 1H) 7.30-7.36 (m, 3H) 6.87-6.94 (m, 2H) 3.80-3.87 (m, 1H) 1.93 (s, 2 H) 1.85 (d, J=2.44 Hz, 3H) 1.80 (d, J=2.75 Hz, 2H) 1.75 (s, 2H) 1.68 (d, J=12.82 Hz, 2H) 1.46 (s, 6H) 1.38 (d, J=12.82 Hz, 2H). MS (ESI+) m/z 392 (M+H)$^+$

EXAMPLE 8

E-4-[2-(4-chloro-phenoxy)-2-methyl-propionylamino]-adamantane-1-carboxylic Acid Amide The title compound was prepared according to the procedure outlined in Example 1E from E-4-[2-(4-chloro-phenoxy)-2-methyl-propionylamino]-adamantane-1-carboxylic acid (Example 7C). $^1$H NMR (400 MHz, DMSO-D6) δ ppm 7.25-7.36 (m, 3H) 6.94-6.99 (m, 1H) 6.89-6.94 (m, 2H) 6.69 (s, 1H) 3.83 (d, J=7.67 Hz, 1H) 1.91 (s, 2H) 1.75-1.87 (m, 5H) 1.63-1.73 (m, 4H) 1.46 (s, 6H) 1.32-1.42 (m, 2H). MS (ESI+) m/z 391 (M+H)$^+$

EXAMPLE 9

E-4-[2-methyl-2-(4-methyl-cyclohexyloxy)-propionylamino]-adamantane-1-carboxylic Acid Amide The title compound was prepared according to the procedures outlined in Example 3 and 1E, substituting 4-methyl-cyclohexanol for 2-methylcyclohexanol. $^1$H NMR (400 MHz, DMSO-D6) δ ppm 7.14 (d, 1H) 6.98 (s, 1H) 6.70 (s, 1H) 3.72-3.82 (m, 1H) 3.39-3.50 (m, 1H) 1.19-1.96 (m, 26H) 0.91-1.05 (m, 2H) 0.81-0.89 (m, 3H). MS (ESI+) m/z 377 (M+H)$^+$.

EXAMPLE 10

E-4-[(2-phenoxypropanoyl)amino]adamantane-1-carboxamide

The title compound was prepared according to the procedure outlined in Example 7C and 1E substituting 2-phenoxypropionyl chloride for 2-(4-chlorophenoxy)-2-methylpropionyl chloride. $^1$H NMR (400 MHz, DMSO-D6) δ ppm 7.74 (d, J=7.36 Hz, 1H) 7.26 (t, J=7.98 Hz, 2H) 6.83-6.99 (m, 4H) 6.68 (s, 1H) 4.86 (q, J=6.55 Hz, 1H) 3.78 (d, J=7.06 Hz, 1H) 1.69-1.92 (m, 11H) 1.43 (d, J=6.44 Hz, 3H) 1.37 (d, J=12.89 Hz, 2H). MS (ESI+) m/z 343 (M+H)$^+$

EXAMPLE 11

E-4-{[2-methyl-2-(2-methylphenoxy)propanoyl]amino}adamantane-1-carboxylic Acid

The title compound was prepared according to the procedure outlined in Example 1D substituting 2-methylphenol for phenol. $^1$H NMR (500 MHz, DMSO-D6) δ ppm 11.58-12.61 (br. s, 1H) 7.28 (d, J=7.32 Hz, 1H) 7.19 (d, J=7.32 Hz, 1H) 7.05-7.13 (m, 1H) 6.91 (t, J=6.87 Hz, 1H) 6.82 (d, J=7.93 Hz, 1H) 3.79-3.88 (m, 1H) 2.22 (s, 3H) 1.95 (s, 2H) 1.86 (d, J=2.75 Hz, 3H) 1.82 (s, 2H) 1.76 (s, 2H) 1.68 (d, J=13.12 Hz, 2H) 1.46 (s, 6H) 1.43 (d, J=13.73 Hz, 2H). MS (ESI+) m/z 372 (M+H)$^+$

EXAMPLE 12

E-4-{[2-methyl-2-(4-methylphenoxy)propanoyl]
amino}adamantane-1-carboxylic Acid

The title compound was prepared according to the procedure outlined in Example 1D substituting 4-methylphenol for phenol. $^1$H NMR (500 MHz, DMSO-D6) δ ppm 11.75-12.46 (br.s, 1H) 7.30 (d, J=7.32 Hz, 1H) 7.08 (d, J=8.24 Hz, 2H) 6.81 (d, J=8.54 Hz, 2H) 3.80-3.86 (m, 1H) 2.23 (s, 3H) 1.94 (s, 2H) 1.86 (d, J=2.44 Hz, 3H) 1.82 (s, 2H) 1.76 (s, 2H) 1.69 (d, J=12.82 Hz, 2H) 1.38-1.45 (m, 8H). MS (ESI+) m/z 372 (M+H)$^+$

EXAMPLE 13

E-4-{[2-(2-chlorophenoxy)-2-methylpropanoyl]
amino}adamantane-1-carboxylic Acid

The title compound was prepared according to the procedure outlined in Example 1D substituting 2-chlorophenol for phenol. $^1$H NMR (500 MHz, DMSO-D6) δ ppm 11.50-12.76 (br. s, 1H) 7.63 (d, J=7.63 Hz, 1H) 7.57 (dd, J=7.93, 1.53 Hz, 1H) 7.36 (t, 1H) 7.24 (dd, J=8.24, 1.22 Hz, 1H) 7.16 (t, 1H) 3.88-3.98 (m, 1H) 2.04 (s, 2H) 1.94 (d, J=2.44 Hz, 5H) 1.82-1.88 (m, 4H) 1.52-1.59 (m, 8H). MS (ESI+) m/z 392 (M+H)$^+$

EXAMPLE 14

E-4-{[2-(2-methoxyphenoxy)-2-methylpropanoyl]
amino}adamantane-1-carboxamide

The title compound was prepared according to the procedure outlined in Example 1D and 1E substituting 2-methoxyphenol for phenol. $^1$H NMR (400 MHz, DMSO-D6) δ ppm 7.91 (d, J=7.67 Hz, 1H) 7.05-7.11 (m, 3H) 7.00 (s, 1H) 6.86-6.93 (m, 1H) 6.71 (s, 1H) 3.81-3.88 (m, 1H) 3.79 (s, 3H) 1.96 (s, 2H) 1.76-1.92 (m, 9H) 1.54 (d, J=13.20 Hz, 2H) 1.36 (s, 6H). MS (ESI+) m/z 387 (M+H)$^+$

EXAMPLE 15

E-4-{[2-(4-methoxyphenoxy)-2-methylpropanoyl]
amino}adamantane-1-carboxamide

The title compound was prepared according to the procedure outlined in Example 1D and 1E substituting 4-methoxyphenol for phenol. $^1$H NMR (400 MHz, DMSO-D6) δ ppm 7.30 (d, J=7.36 Hz, 1H) 6.93-7.01 (m, 1H) 6.82-6.92 (m, 4H) 6.70 (s, 1H) 3.85 (d, J=7.06 Hz, 1H) 3.71 (s, 3H) 1.92-1.97 (m, 2H) 1.77-1.89 (m, 5H) 1.74 (s, 3H) 1.71 (s, 1H) 1.44 (d, J=12.58 Hz, 2H) 1.37 (s, 6H). MS (ESI+) m/z 387 (M+H)$^+$

EXAMPLE 16

E-4-({2-methyl-2-[3-(trifluoromethyl)phenoxy]
propanoyl}amino)adamantane-1-carboxamide The title compound was prepared according to the procedure outlined in Example 1D and 1E substituting 3-trifluoromethylphenol for phenol. $^1$H NMR (400 MHz, DMSO-D6) δ ppm 7.53 (t, J=7.98 Hz, 1H) 7.37 (dd, J=12.12, 7.21 Hz, 2H) 7.19 (dd, 1H) 7.14 (s, 1H) 6.95 (s, 1H) 6.68 (s, 1H) 3.81 (s, 1H) 1.90 (s, 2H) 1.80 (d, J=7.67 Hz, 4H) 1.76 (s, 1H) 1.70 (s, 2H) 1.61 (d, 2H) 1.52 (s, 6H) 1.32 (d, J=13.50 Hz, 2H). MS (ESI+) m/z 425 (M+H)$^+$

EXAMPLE 17

E-4-{[2-(3-methoxyphenoxy)-2-methylpropanoyl]
amino}adamantane-1-carboxamide

The title compound was prepared according to the procedure outlined in Example 1D and 1E substituting 3-methoxyphenol for phenol. $^1$H NMR (500 MHz, DMSO-D6) δ ppm 7.26 (d, J=7.32 Hz, 1H) 7.17 (t, J=8.24 Hz, 1H) 6.98 (s, 1H) 6.71 (s, 1H) 6.60 (dd, J=8.39, 1.98 Hz, 1H) 6.43-6.48 (m, 2H) 3.82 (d, J=7.02 Hz, 1H) 3.70 (s, 3H) 1.91 (s, 2H) 1.76-1.86 (m, 5H) 1.71 (s, 2H) 1.66 (d, J=12.82 Hz, 2H) 1.46 (s, 6H) 1.36 (d, J=12.51 Hz, 2H). MS (ESI+) m/z 387 (M+H)$^+$

EXAMPLE 18

N-adamantan-2-yl-2-(4-chloro-phenoxy)-2-methyl-
propionamide

The title compound was prepared according to the procedure outlined in Example 7C substituting 4-adamantamine hydrochloride for E-4-adamantamine-1-carboxylic acid methyl ester. $^1$H NMR (400 MHz, DMSO-D6) δ ppm 7.30-7.35 (m, 2H) 7.25 (d, J=7.36 Hz, 1H) 6.89-6.94 (m, 2H) 3.83-3.91 (m, 1H) 1.82 (d, J=10.74 Hz, 2H) 1.77 (s, 5H) 1.64-1.73 (m, 5H) 1.42-1.49 (m, 8H). MS (ESI+) m/z 348 (M+H)$^+$.

EXAMPLE 19

E-2-(4-Chloro-phenoxy)-N-(5-hydroxy-adamantan-
2-yl)-2-methyl-propionamide

The title compound was prepared according to the procedure outlined in Example 7C substituting E-4-aminoadamantan-1-ol for E-4-adamantamine-1-carboxylic acid methyl ester. $^1$H NMR (400 MHz, DMSO-D6) δ ppm 7.30-7.35 (m, 2H) 7.22 (d, J=7.06 Hz, 1H) 6.88-6.94 (m, 2H) 4.21-4.52 (br s, 1H) 3.75-3.80 (m, 1H) 1.96 (s, 2H) 1.91 (s, 1H) 1.64-1.71 (m, 2H) 1.53-1.62 (m, 6H) 1.45 (s, 6H) 1.27 (d, J=12.58 Hz, 2H). MS (ESI+) m/z 364 (M+H)$^+$.

EXAMPLE 20

E-{[2-Methyl-2-(4-methylphenoxy)propanoyl]
amino}adamantane-1-carboxamide

A solution of the product of Example 12 (24 mg, 0.064 mmol) in DCM (2 mL) was treated with HOBt (9.5 mg, 0.07 mmol) and EDCI (14.7 mg, 0.077 mmol) and stirred at room temperature for 1 hour. Excess of aqueous (30%) ammonia (2 mL) was added and the reaction was stirred for additional 20 hours. The layers were separated and the aqueous layer extracted with DCM (2×2 mL). The combined organic extracts were washed with water (3×2 mL), brine (2 mL), dried (MgSO$_4$) and filtered. The filtrate was concentrated under reduced pressure to provide the crude compound that was purified by reverse phase preparative HPLC on a Waters Symmetry C8 column (25 mm×100 mm, 7 um particle size) using a gradient of 10% to 100% acetonitrile:0.1% aqueous TFA over 8 min (10 min run time) at a flow rate of 40 mL/min. to provide the title compound. $^1$H NMR (500 MHz, DMSO-d$_6$) δ ppm 7.28 (d, J=7.36 Hz, 1H), 7.08 (d, J=8.12 Hz, 2H), 6.98-6.99 (bs, 1H), 6.80-6.82 (m, 2H), 6.71-6.73 (bs, 1H), 3.81-3.86 (m, 1H), 2.23 (s, 3H), 1.91-1.93 (m, 2H), 1.77-1.87 (m, 5H), 1.71-1.73 (m, 2H), 1.65-1.70 (m, 2H), 1.41 (s, 6H), 1.37-1.42 (m, 2H). MS (ESI+) m/z 371 (M+H)$^+$.

EXAMPLE 21

E-4-{[2-(3-Chlorophenoxy)-2-methylpropanoyl]amino}adamantane-1-carboxamide

EXAMPLE 21A

Example 21A was prepared according to the procedure outlined in Example 1D, substituting 3-chlorophenol for phenol.

EXAMPLE 21B

E-4-{[2-(3-Chlorophenoxy)-2-methylpropanoyl]amino}adamantane-1-carboxamide

The title compound was prepared using the procedure as described in Example 1E, substituting the product of Example 21A for the product of Example 1D. $^1$H NMR (500 MHz, DMSO-$d_6$) δ ppm 7.35 (d, J=6.93 Hz, 1H), 7.31 (t, J=8.10 Hz, 1H), 7.07 (dd, J=7.83, 1.91 Hz, 1H), 6.97-6.98 (bs, 1H), 6.92 (t, J=2.15 Hz, 1H), 6.87 (dd, J=8.22, 2.29 Hz, 1H), 6.70-6.72 (bs, 1H), 1.90-1.93 (m, 2H), 1.70-1.71 (m, 2H), 1.49 (s, 6H), 3.80-3.84 (m, 1H), 1.76-1.85 (m, 5H), 1.60-1.68 (m, 2H), 1.33-1.37 (m, 2H). MS (ESI+) m/z 391 (M+H)$^+$.

EXAMPLE 22

E-4-({2-Methyl-2-[4-(trifluoromethoxy)phenoxy]propanoyl}amino)adamantane-1-carboxamide

EXAMPLE 22A

Example 22A was prepared according to the procedure outlined in Example 1D, substituting 4-trifluoromethoxyphenol for phenol.

EXAMPLE 22B

E-4-({2-Methyl-2-[4-(trifluoromethoxy)phenoxy]propanoyl}amino)adamantane-1-carboxamide The title compound was prepared using the procedure as described in Example 1E, substituting the product of Example 22A for the product of Example 1D. $^1$H NMR (400 MHz, DMSO-$d_6$) δ ppm 7.41 (t, J=8.25 Hz, 1H), 7.33 (d, J=6.94 Hz, 1H), 7.00 (d, J=8.15 Hz, 1H), 6.90-6.96 (m, 2H), 6.82-6.84 (bs, 1H), 6.67-6.69 (bs, 1H), 3.79-3.84 (m, 1H), 1.87-1.90 (m, 2H), 1.75-1.86 (m, 5H), 1.69-1.71 (m, 2H), 1.63-1.69 (m, 2H), 1.51 (s, 6H), 1.29-1.37 (m, 2H). MS (ESI+) m/z 441 (M+H)$^+$.

EXAMPLE 23

E-4-{[2-(3-Bromophenoxy)-2-methylpropanoyl]amino}adamantane-1-carboxylic Acid

The title compound was prepared according to the procedure outlined in Example 1D, substituting 3-bromo-phenol for phenol. $^1$H NMR (500 MHz, DMSO-$d_6$) δ ppm 12.05-12.10 (s, 1H), 7.38 (d, J=6.82 Hz, 1H), 7.19-7.27 (m, 2H), 7.06 (t, J=2.06 Hz, 1H), 6.91 (ddd, J=8.09, 2.36, 1.18 Hz, 1H), 3.80-3.84 (m, 1H), 1.93-1.96 (m, 2H), 1.84-1.85 (m, 4H), 1.77-1.80 (m, 1H), 1.74-1.76 (m, 2H), 1.65-1.70 (m, 2H), 1.48 (s, 6H), 1.36-1.40 (m, 2H). MS (ESI+) m/z 437 (M+H)$^+$.

EXAMPLE 24

4-({[((E)-4-{[2-(4-Chlorophenoxy)-2-methylpropanoyl]amino}-1-adamantyl)carbonyl]amino}methyl)benzoic Acid To a solution of the product of Example 7C (200 mg, 0.51 mmol) and TBTU (246 mg, 0.77 mmol) in DMF (5 mL) was added N,N-diisopropylethylamine (0.27 mL, 1.53 mmol) followed by 4-aminomethyl-benzoic acid methyl ester hydrochloride (123 mg, 0.61 mmol) and stirred at room temperature for 20 hours. The reaction mixture was concentrated in vacuo. The residue was taken in ethyl acetate and washed with water and brine respectively, dried (MgSO$_4$) and concentrated in vacuo to get crude methyl ester of the title compound that was purified by reverse phase preparative HPLC on a Waters Symmetry C8 column (40 mm×100 mm, 7 um particle size) using a gradient of 10% to 100% acetonitrile:0.1% aqueous TFA over 12 min (15 min run time) at a flow rate of 70 mL/min. and concentrated. The methyl ester of the title compound was hydrolyzed as described in step B of Example 1D. The crude acid product was purified by reverse phase preparative HPLC on a Waters Symmetry C8 column (40 mm×100 mm, 7 um particle size) using a gradient of 10% to 100% acetonitrile:0.1% aqueous TFA over 12 min (15 min run time) at a flow rate of 70 mL/min. to provide the title compound. $^1$H NMR (400 MHz, DMSO-$d_6$) δ ppm 12.77-12.82 (bs, 1H), 8.08 (t, J=5.96 Hz, 1H), 7.88 (d, J=7.99 Hz, 2H), 7.29-7.36 (m, 5H), 6.91-6.93 (m, 2H), 4.31 (d, J=5.86 Hz, 2H), 3.84-3.89 (m, 1H), 1.93-1.96 (m, 2H), 1.82-1.91 (m, 5H), 1.77-1.79 (m, 2H), 1.67-1.72 (m, 2H), 1.47 (s, 6H), 1.32-1.45 (m, 2H). MS (ESI+) m/z 525 (M+H)$^+$.

EXAMPLE 25

E-4-{[2-(2,3-Dimethylphenoxy)-2-methylpropanoyl]amino}adamantane-1-carboxylic Acid

EXAMPLE 25A 2-(2,3-Dimethylphenoxy)-2-methyl-propionic Acid

To an ice cold solution of 2,3-dimethylphenol (136 mg, 1.0 mmol) and 1,1,1-trichloro-2-methyl-2-propanol hydrate (492 mg, 2.75 mmol) in acetone (2 mL) was added powdered sodium hydroxide (393 mg, 9.83 mmol) in three equal portions at 1 hour interval. After each addition reaction mixture was allowed to come to room temperature. Before last addition of sodium hydroxide, acetone (2 mL) was added to the reaction mixture. The reaction mixture was stirred at room temperature for 48 hours and concentrated in vacuo. The residue was diluted with water and acidified to pH 1 with aqueous HCl and extracted with diethyl ether (3×5 mL). The organic layers were pooled, dried (Na$_2$SO$_4$) and filtered. The filtrate was concentrated under reduced pressure to provide the crude that was purified by reverse phase preparative HPLC on a Waters Symmetry C8 column (40 mm×100 mm, 7 um particle size) using a gradient of 10% to 100% acetonitrile:0.1% aqueous TFA over 12 min (15 min run time) at a flow rate of 70 mL/min. to provide the title compound as a pale yellow solid (158 mg, 76%).

EXAMPLE 25B

E-4-{[2-(2,3-Dimethylphenoxy)-2-methylpropanoyl] amino}adamantane-1-carboxylic Acid To a solution of the product of Example 25A (20.8 mg, 0.1 mmol) and TBTU (48 mg, 0.15 mmol) in DMF (1 mL) was added N,N-diisopropylethylamine (0.052 mL, 0.3 mmol) followed by the product of Example 7B (30 mg, 0.12 mmol) and stirred at room temperature for 20 hours. The reaction mixture was concentrated in vacuo. The residue was purified by reverse phase preparative HPLC on a Waters Symmetry C8 column (25 mm×100 mm, 7 um particle size) using a gradient of 10% to 100% acetonitrile:0.1% aqueous TFA over 8 min (10 min run time) at a flow rate of 40 mL/min. and hydrolyzed as described in step B of Example 1D to provide the title compound. $^1$H NMR (500 MHz, DMSO-$d_6$) δ ppm 12.03-12.14 (bs, 1H), 7.30 (d, J=7.30 Hz, 1H), 6.98 (t, J=7.79 Hz, 1H), 6.84 (d, J=7.44 Hz, 1H), 6.68 (d, J=8.14 Hz, 1H), 3.84-3.88 (m, 1H), 2.22 (s, 3H), 2.14 (s, 3H), 1.95-1.97 (m, 2H), 1.83-1.88 (m, 5H), 1.76-1.78 (m, 2H), 1.69-1.73 (m, 2H), 1.41-1.48 (m, 2H), 1.43 (s, 6H). MS (ESI+) m/z 386 (M+H)$^+$.

EXAMPLE 26 tert-Butyl 4-(2-{[(E)-5-(aminocarbonyl)-2-adamantyl]amino}-1,1-dimethyl-2-oxoethoxy)phenylcarbamate

EXAMPLE 26A

Example 26A was prepared according to the procedure outlined in Example 25A, substituting (4-hydroxy-phenyl)-carbamic acid tert-butyl ester for 2,3-dimethylphenol.

EXAMPLE 26B

Example 26B was prepared using the procedure as described in Example 25B, substituting the product of Example 26A for the product of Example 25A.

EXAMPLE 26C tert-Butyl 4-(2-{[(E)-5-(aminocarbonyl)-2-adamantyl]amino}-1,1-dimethyl-2-oxoethoxy)phenylcarbamate The title compound was prepared using the procedure as described in Example 1E, substituting the product of Example 26B for the product of Example 1D. $^1$H NMR (400 MHz, DMSO-$d_6$) δ ppm 9.18-9.20 (bs, 1H), 7.34 (d, J=8.50 Hz, 2H), 7.28 (d, J=7.37 Hz, 1H), 6.96-6.98 (bs, 1H), 6.84 (d, J=8.77 Hz, 2H), 6.68-6.70 (bs, 1H), 3.81-3.87 (m, 1H), 1.92-1.95 (m, 2H), 1.80-1.89 (m, 5H), 1.68-1.75 (m, 4H), 1.46 (s, 9H), 1.39-1.46 (m, 2H), 1.39 (s, 6H). MS (ESI+) m/z 472 (M+H)$^+$.

EXAMPLE 27

E-N-[4-(Aminocarbonyl)benzyl]-4-{[2-(4-chlorophenoxy)-2-methylpropanoyl]amino}adamantane-1-carboxamide The title compound was prepared according to the procedure outlined in Example 1E substituting the product of Example 24 for the product of Example 1D. $^1$H NMR (400 MHz, DMSO-$d_6$) δ ppm 8.03-8.08 (m, 1H), 7.86-7.88 (bs, 1H), 7.80 (d, J=8.09 Hz, 2H), 7.32-7.35 (m, 2H), 7.26-7.32 (m, 2H), 7.24-7.27 (m, 2H), 6.91-6.93 (m, 2H), 4.29 (d, J=5.87 Hz, 2H), 3.83-3.89 (m, 1H), 1.82-1.96 (m, 7H), 1.77-1.79 (m, 2H), 1.66-1.72 (m, 2H), 1.46 (s, 6H), 1.37-1.42 (m, 2H). MS (ESI+) m/z 524 (M+H)$^+$.

EXAMPLE 28

E-N-[4-(Aminocarbonyl)methyl]-4-{[2-(4-chlorophenoxy)-2-methylpropanoyl]amino}adamantane-1-carboxamide

EXAMPLE 28A

Example 28A was prepared according to the procedure outlined in Example 24, substituting glycine methyl ester hydrochloride for 4-aminomethyl-benzoic acid methyl ester hydrochloride.

EXAMPLE 28B

E-N-[4-(Aminocarbonyl)methyl]-4-{[2-(4-chlorophenoxy)-2-methylpropanoyl]amino}adamantane-1-carboxamide The title compound was prepared using the procedure as described in Example 1E, substituting the product of Example 28A for the product of Example 1D. $^1$H NMR (400 MHz, DMSO-$d_6$) δ ppm 7.49-7.54 (m, 1H), 7.32-7.35 (m, 2H), 7.31 (d, J=7.21 Hz, 1H), 7.08-7.11 (bs, 1H), 6.93-6.97 (m, 1H), 6.91-6.93 (m, 2H), 3.82-3.87 (m, 1H), 3.58 (d, J=5.68 Hz, 2H), 1.92-1.98 (m, 2H), 1.80-1.90 (m, 5H), 1.74-1.76 (m, 2H), 1.65-1.71 (m, 2H), 1.46 (s, 6H), 1.36-1.41 (m, 2H). MS (ESI+) m/z 448 (M+H)$^+$.

EXAMPLE 29

3-({[((E)-4-{[2-(4-Chlorophenoxy)-2-methylpropanoyl]amino}-1-adamantyl)carbonyl] amino}methyl)benzoic Acid The title compound was prepared according to the procedure outlined in Example 24, substituting 3-aminomethyl-benzoic acid methyl ester hydrochloride for 4-aminomethyl-benzoic acid methyl ester hydrochloride. $^1$H NMR (400 MHz, DMSO-$d_6$) δ ppm 12.81-12.91 (m, 1H), 8.06-8.12 (m, 1H), 7.77-7.82 (m, 2H), 7.40-7.44 (m, 2H), 7.31-7.35 (m, 2H), 7.30-7.32 (m, 1H), 6.91-6.93 (m, 2H), 4.30 (d, J=5.89 Hz, 2H), 3.83-3.88 (m, 1H), 1.93-1.96 (m, 2H), 1.82-1.90 (m, 5H), 1.77-1.79 (m, 2H), 1.67-1.72 (m, 2H), 1.46 (s, 6H), 1.37-1.42 (m, 2H). MS (ESI+) m/z 525 (M+H)$^+$.

EXAMPLE 30

E-4-({2-[(5-Bromopyridin-2-yl)oxy]-2-methylpropanoyl}amino)adamantane-1-carboxamide

EXAMPLE 30A 2-(5-Bromo-pyridin-2-yloxy)-2-methyl-propionic Acid

Step A

To a stirred and cooled (0° C.) solution of 2-hydroxy-2-methyl-propionic acid methyl ester (2.6 mL, 22.70 mmol) and 5-bromo-2-fluoro-pyridine (3.32 g, 18.92 mmol) in THF (26 mL) and DMPU (13 mL) was added portionwise NaH (1 g, 60% in oil, 24.59 mmol). After the addition, the resulting mixture was warmed to room temperature and stirred overnight. Saturated NH$_4$Cl was then added to quench the reaction and Et$_2$O was used to partition the mixture. The organic phase was washed with water, brine, dried over MgSO$_4$, and filtered. After concentration, the residue was purified over silica gel using 20% EtOAc/hexane and concentrated to give a clear oil.

Step B

The product of Step A (1.56 g, 5.71 mmol) was dissolved in THF (30 mL) and KOTMS (1.1 g, 8.57 mmol) was added in one portion. The resulting solution was stirred at room temperature overnight. Et$_2$O (30 mL) and water (40 mL) were added to the reaction to partition the mixture. The phases were separated, and the aqueous phase was acidified using 10% NaHSO$_4$ solution and extracted with EtOAc. The combined organic phases were dried over MgSO$_4$, filtered and concentrated to give the title compound as a white solid.

EXAMPLE 30B

E-4-({2-[(5-Bromopyridin-2-yl)oxy]-2-methylpropanoyl}amino)adamantane-1-carboxamide Step A HATU (2.46 g, 6.48 mmol) was added in one portion to a solution of the product of Step B of Example 30A (1.40 g, 5.40 mmol), the product of Example 7B (1.45 g, 5.95 mmol), and DIPEA (2.82 mL, 16.2 mmol) in dry CH$_2$Cl$_2$ (20 mL). The resulting solution was allowed to stir at room temperature overnight before it was diluted with CH$_2$Cl$_2$ and washed with aqueous NaHSO$_4$ solution, 1 M NaOH, dried (Na$_2$SO$_4$) and evaporated. The residue was purified over silica gel using 30% EtOAc/hexanes and concentrated to give an oil.

Step B

To the product of Step A (2.27 g, 5.04 mmol) in THF (15 mL) was added KOTMS (1.42 g, 11.08 mmol) and the resulting solution was stirred at room temperature overnight before it was diluted with Et$_2$O and water. The phases were separated and the aqueous phase was acidified with NaHSO$_4$ solution and extracted with EtOAc. The combined organic phases were dried (MgSO$_4$) and evaporated to give a white solid.

Step C

EDCI (1.40 g, 7.25 mmol) was added to a solution of the product of Step B (2.17 g, 4.84 mmol), HOBt (1.17 g, 8.71 mmol), DIPEA (2.5 mL, 14.4 mmol) in dry CH$_2$Cl$_2$ (20 mL). The resulting solution was allowed to stir at room temperature for 1 hr before NH$_3$ solution was added (12 mL, 2M in iPrOH). The mixture was stirred for 2 hours at 25° C., diluted with CH$_2$Cl$_2$ and washed with NaHSO$_4$ solution, 1M NaOH, brine, dried (Na$_2$SO$_4$) and evaporated. The residue was purified over silica gel using 5% MeOH/CH$_2$Cl$_2$ to give the title compound as a white solid. $^1$H NMR (300 MHz, CD$_3$OD) δ ppm 8.11 (d, J=2.52 Hz, 1H), 7.82 (dd, J=8.74, 2.60 Hz, 1H), 6.84 (d, J=8.74 Hz, 1H), 3.89-3.92 (m, 1H), 1.91-1.99 (m, 6H), 1.83 (s, 3H), 1.66 (s, 6H), 1.41-1.62 (m, 4H). MS (ESI+) m/z 436 (M+H)$^+$.

EXAMPLE 31

E-4-{[2-(2-Cyanophenoxy)-2-methylpropanoyl]amino}adamantane-1-carboxamide

EXAMPLE 31A

Example 31A was prepared according to the procedure outlined in Example 25A, substituting 2-hydroxy-benzonitrile for 2,3-dimethylphenol.

EXAMPLE 31B

Example 31B was prepared using the procedure as described in Example 25B, substituting the product of Example 31A for the product of Example 25A.

EXAMPLE 31C

E-4-{[2-(2-Cyanophenoxy)-2-methylpropanoyl]amino}adamantane-1-carboxamide

The title compound was prepared using the procedure as described in Example 1E, substituting the product of Example 31B for the product of Example 1D. $^1$H NMR (500 MHz, DMSO-d$_6$) δ ppm 7.78 (dd, J=7.68, 1.75 Hz, 1H), 7.62 (ddd, J=8.54, 7.48, 1.68 Hz, 1H), 7.49 (d, J=6.94 Hz, 1H), 7.17 (td, J=7.58, 0.87 Hz, 1H), 7.08 (d, J=8.53 Hz, 1H), 6.98-6.99 (bs, 1H), 6.71-6.72 (bs, 1H), 3.83-3.87 (m, 1H), 1.94-1.96 (m, 2H), 1.75-1.88 (m, 7H), 1.71-1.73 (m, 2H), 1.60 (s, 6H), 1.35-1.39 (m, 2H). MS (ESI+) m/z 382 (M+H)$^+$.

EXAMPLE 32

E-4-{[2-(4-Hydroxyphenoxy)-2-methylpropanoyl]amino}adamantane-1-carboxamide

EXAMPLE 32A

Example 32A was prepared according to the procedure outlined in Example 25A, substituting 4-benzyloxy-phenol for 2,3-dimethylphenol.

EXAMPLE 32B

Example 32B was prepared according to the procedure outlined in Example 25B, substituting the product of Example 32A for the product of Example 25A.

EXAMPLE 32C

Example 32C was prepared according to the procedure outlined in Example 1E, substituting the product of Example 32B for the product of Example 1D.

EXAMPLE 32D

E-4-{[2-(4-Hydroxyphenoxy)-2-methylpropanoyl]amino}adamantane-1-carboxamide

The product of Example 32C (62 mg, 0.13 mmol) was debenzylated using 20% Pd(OH)$_2$/C (63 mg) and methanol (2 mL) at 60 psi at room temperature for 20 hours. The reaction mixture was filtered and concentrated under reduced pressure to provide the crude product that was purified by reverse phase preparative HPLC on a Waters Symmetry C8 column (25 mm×100 mm, 7 um particle size) using a gradient of 10% to 100% acetonitrile: 0.1% aqueous TFA over 8 min (10 min run time) at a flow rate of 40 mL/min. to provide title compound as a white solid. $^1$H NMR (400 MHz, DMSO-$d_6$) δ ppm 9.12 (s, 1H), 7.28 (d, J=7.49 Hz, 1H), 6.96-6.99 (bs, 1H), 6.77-6.79 (m, 2H), 6.69-6.71 (bs, 1H), 6.63-6.69 (m, 2H), 3.81-3.87 (m, 1H), 1.93-1.95 (m, 2H), 1.78-1.89 (m, 5H), 1.69-1.76 (m, 4H), 1.42-1.47 (m, 2H), 1.35 (s, 6H). MS (ESI+) m/z 373 (M+H)$^+$.

EXAMPLE 33

((E)-4-{[2-(4-Chlorophenoxy)-2-methylpropanoyl] amino}-1-adamantyl)acetic Acid

EXAMPLE 33A 2-(4-chlorophenoxy)-N-[(E)-5-(hydroxymethyl)-2-adamantyl]-2-methylpropanamide To a cold (−30° C.) solution of the methyl ester of Example 7C (870 mg, 2.15 mmol) in THF (3.0 mL) was added 1N LAH in THF solution (3.22 ml, 3.22 mmol) slowly under $N_2$ flow. The reaction mixture was stirred from −30° C. to 0° C. for 3 hours. It was quenched with water carefully, acidified with 1N HCl and extracted with DCM 3 times. The combined organic layer was dried over $Na_2SO_4$, filtered, concentrated under reduced pressure and the residue purified by flash chromatography with 30% ethyl acetate/70% hexane to provide the title compound (690 mg, 85%). $^1$H NMR (300 MHz, CDCl$_3$) δ ppm 9.32-9.39 (m, 1H), 7.17-7.29 (m, 2H), 7.00 (d, 1H), 6.81-6.91 (m, 2H), 3.99-4.12 (m, 1H), 1.44-2.15 (m, 21H). MS (ESI+) m/z 378 (M+H)$^+$.

EXAMPLE 33B

E-4-[2-(4-Chlorophenoxy)-2-methyl-propionylamino]-adamantane-1-carbaldehyde

To a solution of the product of Example 33A (990 mg, 2.63 mmol) in DCE (8.0 mL) were added NMO (461 mg, 3.94 mmol), TPAP (46 mg, 0.13 mmol) and molecular sieves at room temperature under $N_2$ flow. The reaction mixture was stirred overnight at room temperature. It was filtered through Celite and washed with DCM 3 times. The combined filtrate was concentrated under reduced pressure and purified by flash chromatography with 30% ethyl acetate/70% hexane to provide the title compound (740 mg, 75%). $^1$H NMR (300 MHz, CDCl$_3$) δ ppm 9.36 (m, 1H), 7.20-7.26 (m, 2H), 6.95-7.05 (m, 1H), 6.82-6.91 (m, 2H), 4.00-4.10 (m, 1H), 1.48-2.13 (m, 19H). MS (ESI+) m/z 376 (M+H)$^+$.

EXAMPLE 33C

E-{4-[2-(4-Chlorophenoxy)-2-methyl-propionylamino]-adamantan-1-yl}-acetonitrile

To a cold (0° C.) solution of the product of Example 33B (375 mg, 1 mmol) in DME (5.0 mL)/EtOH (0.15 ml) was added TosMIC (254 mg, 1.3 mmol) and t-BuOK (281 mg, 2.5 mmol) under $N_2$ flow. The reaction mixture was stirred at room temperature for 2 hrs, then heated to 35-40° C. for 30 minutes. It was filtered through $Al_2O_3$ plug after it was cool down to room temperature and washed with DME (3×). The combined filtrate was concentrated under reduced pressure and purified by flash chromatography with 30% ethyl acetate/70% hexane to provide the title compound (200 mg, 52%). $^1$H NMR (400 MHz, CDCl$_3$) δ ppm 7.19-7.29 (m, 2H), 6.91-7.01 (m, 1H), 6.81-6.90 (m, 2H), 3.96-4.05 (m, 1H), 2.14 (s, 2H), 1.94-2.08 (m, 3H), 1.47-1.75 (m, 15H). MS (ESI+) m/z 387 (M+H)$^+$.

EXAMPLE 33D ((E)-4-{[2-(4-Chlorophenoxy)-2-methylpropanoyl] amino}-1-adamantyl)acetic Acid To a solution of the product of Example 33C (40 mg, 0.1 mmol) in ethylene glycol (0.5 ml) was added 25% KOH solution (0.2 ml). The reaction mixture was heated to 150° C. overnight and concentrated. The residue was purified by reverse phase preparative HPLC on a Waters Symmetry C8 column (25 mm×100 mm, 7 um particle size) using a gradient of 10% to 100% acetonitrile:0.1% aqueous TFA over 8 min (10 min run time) at a flow rate of 40 mL/min. to provide the title compound (19 mg, 45%). $^1$H NMR (400 MHz, CDCl$_3$) δ ppm 7.19-7.25 (m, 2H), 6.96-7.02 (m, 1H), 6.82-6.90 (m, 2H), 3.98-4.07 (m, 1H), 2.11-2.18 (m, 2H), 1.88-2.03 (m, 3H), 1.47-1.85 (m, 16H). MS (ESI+) m/z 406 (M+H)$^+$.

EXAMPLE 34

N-[(E)-5-(2-Amino-2-oxoethyl)-2-adamantyl]-2-(4-chlorophenoxy)-2-methylpropanamide To a solution of the product of Example 33C (22 mg, 0.057 mmol) in MeOH (0.15 ml)/DMSO (0.005 ml) were added 30% $H_2O_2$ (0.011 ml) and 0.2 M NaOH (0.006 ml). The reaction mixture was heated to 50° C. overnight and concentrated. The residue was purified by reverse phase preparative HPLC on a Waters Symmetry C8 column (25 mm×100 mm, 7 um particle size) using a gradient of 10% to 100% acetonitrile:0.1% aqueous TFA over 8 min (10 min run time) at a flow rate of 40 mL/min. to provide the title compound (13 mg, 56%). $^1$H NMR (500 MHz, CDCl$_3$) δ ppm 7.21-7.26 (m, 2H), 6.94-7.04 (m, 1H), 6.84-6.91 (m, 2H), 5.62-5.72 (m, 1H), 5.35-5.43 (m, 1H), 3.97-4.06 (m, 1H), 1.89-2.05 (m, 5H), 1.48-1.80 (m, 18H). MS (ESI+) m/z 405 (M+H)$^+$.

EXAMPLE 35

2-(4-Chlorophenoxy)-2-methyl-N-[(E)-5-(2H-tetraazol-5-ylmethyl)-2-adamantyl]propanamide To a solution of the product of Example 33C (65 mg, 0.168 mmol) in water (0.2 ml)/isopropanol (0.1 ml) were added NaN$_3$ (22 mg, 0.337 mmol) and ZnBr$_2$ (19 mg, 0.084 mmol). The reaction mixture was heated to 150° C. in a sealed tube for two days and concentrated. The residue was purified by reverse phase preparative HPLC on a Waters Symmetry C8 column (25 mm×100 mm, 7 um particle size) using a gradient of 10% to 100% acetonitrile:0.1% aqueous TFA over 8 min (10 min run time) at a flow rate of 40 mL/min. to provide the title compound (43 mg, 45%). $^1$H NMR (400 MHz, CD$_3$OD) δ ppm 7.34-7.43 (m, 1H), 7.23-7.31 (m, 2H), 6.89-6.96 (m, 2H), 3.84-3.92 (m, 1H), 2.75 (s, 2H), 1.86-2.02 (m, 3H), 1.43-1.74 (m, 16H). MS (ESI+) m/z 430 (M+H)$^+$.

EXAMPLE 36

N-{(E)-5-[(Aminosulfonyl)methyl]-2-adamantyl}-2-(4-chlorophenoxy)-2-methylpropanamide

EXAMPLE 36A

N-{(E)-5-[(Thioacetyl)methyl]-2-adamantyl}-2-(4-chlorophenoxy)-2-methylpropanamide To a 0° C. solution of the product of Example 33A (0.71 g, 1.88 mmol) in CH$_2$Cl$_2$ (5.0 mL) and pyridine (0.46 mL, 5.64 mmol) was added trifluoromethanesulfonic anhydride (0.35 mL, 2.07 mmol). The reaction mixture was stirred under an atmosphere of N$_2$ for 30 min at 0° C. The crude products were diluted with EtOAc, washed with water and brine, dried over Na$_2$SO$_4$, filtered, and concentrated in vacuo. The resulting crude material was dissolved in DMF (5.0 mL), treated with potassium thioacetate (0.43 g, 3.76 mmol), and heated to 70° C. overnight. The crude reaction mixture was diluted with EtOAc, washed with water (3×) and brine, dried over Na$_2$SO$_4$, filtered, and concentrated in vacuo. The crude product was purified by silica gel chromatography employing a solvent gradient (hexane→60:40 hexane:EtOAc) to yield the title compound (0.74 g, 90%) as a white solid. $^1$H NMR (300 MHz, CDCl$_3$) δ ppm 7.23 (d, J=8.82 Hz, 2H), 6.95 (m, 1H), 6.86 (d, J=8.82 Hz, 2H), 3.98 (m, 1H), 2.76 (s, 2H), 2.35 (s, 3H), 1.89-1.97 (m, 3H) 1.45-1.68 (m, 10H), 1.50 (s, 6H). MS (ESI+) m/z 436 (M+H)$^+$.

EXAMPLE 36B

N-{(E)-5-[(Sulfonic acid)methyl]-2-adamantyl}-2-(4-chlorophenoxy)-2-methylpropanamide To a solution of the product of Example 36A (0.74 g, 1.70 mmol) and NaOAc (0.1392 g, 1.70 mmol) in acetic acid (10 mL) was added 30% hydrogen peroxide in water (1.6 mL, 15.3 mmol). The reaction solution was stirred at room temperature overnight and excess peroxide quenched by adding dimethylsulfide (1.9 mL, 25.5 mmol) and stirring for 2 h. The reaction solution was concentrated under reduced pressure to provide the crude product as a white solid. $^1$H NMR (300 MHz, CDCl$_3$) δ ppm 7.22 (d, J=8.85 Hz, 2H), 7.07 (d, J=7.94 Hz, 1H), 6.86 (d, J=8.85 Hz, 2H), 3.95 (m, 1H), 2.80 (s, 2H), 1.51-2.17 (m, 13H) 1.46 (s, 6H). MS (ESI+) m/z 442 (M+H)$^+$.

EXAMPLE 36C

N-{(E)-5-[(Aminosulfonyl)methyl]-2-adamantyl}-2-(4-chlorophenoxy)-2-methylpropanamide To a solution of the product of Example 36B (55.8 mg, 0.126 mmol) in DCM (1.2 mL) and DMF (1 drop) was added triphosgene (27.4 mg, 0.0922 mmol) and triethylamine (0.018 mL, 0.126 mmol). The resulting reaction mixture was stirred at room temperature for 2 hours and ammonia (0.5 M in dioxane, 2.5 mL, 1.26 mmol) was added. After stirring for 2 h at room temperature the reaction was quenched with water and extracted with EtOAc. The organic layer was then rinsed with brine, dried over Na$_2$SO$_4$, filtered, and concentrated in vacuo. The crude product was purified by reverse phase preparative HPLC using acetonitrile: 10 mM NH$_4$OAc on YMC Guardpak column to provide the title compound (20 mg, 36%) as a white solid. $^1$H NMR (400 MHz, CDCl$_3$) δ ppm 7.24 (d, J=8.9 Hz, 2H), 6.98 (d, J=8.28 Hz, 1H), 6.86 (d, J=8.9 Hz, 2H), 4.79 (s, 2H), 4.04 (m, 1H), 3.04 (s, 2H), 1.87-2.04 (m, 8H), 1.54-1.66 (m, 5H), 1.50 (s, 6H). MS (ESI+) m/z 441 (M+H)$^+$.

EXAMPLE 37

N-{(E)-5-[(Z)-Amino(hydroxyimino)methyl]-2-adamantyl}-2-(4-chlorophenoxy)-2-methylpropanamide

EXAMPLE 37A (5-Carbamoyl-adamantan-2-yl)-carbamic Acid Benzyl Ester

Step A

CbzCl (3.48 mL, 24.72 mmol) was added dropwise to a stirred and cooled (0° C.) solution of the product of Example 7B (5.05 g, 20.60 mmol) and DIPEA (7.9 mL, 45.32 mmol) in dry CH$_2$Cl$_2$ (100 mL). After the addition, the solution was allowed to warm to room temperature and stirred for another 2 hrs. Saturated NaHCO$_3$ solution was added to quench the reaction and the phases were separated. The organic phase was washed with NaHSO$_4$ solution, NaHCO$_3$ solution, dried (Na$_2$SO$_4$), filtered, and concentrated. The residue was purified over silica gel using 20% EtOAc in hexanes and concentrated.

Step B

The product of step A (6.49 g, 18.91 mmol) was dissolved in dry THF (90 mL) and KOTMS (4.85 g, 37.82 mmol) was added at room temperature. The resulting solution was stirred overnight before water (100 mL) and Et$_2$O (100 mL) were added and the phases were separated. The aqueous phase was acidified using solid NaHSO$_4$ until pH 1 was reached. The aqueous phase was then extracted using EtOAc. The combined organic extract was dried (MgSO$_4$), filtered, and concentrated.

Step C

The product of Step B (18.91 mmol) was dissolved in dry CH$_2$Cl$_2$ (60 mL) and DIPEA (10 mL, 56.7 mmol), HOBt (5.1 g, 37.82 mmol), and EDCI (5.4 g, 28.36 mmol) were added to the solution. The resulting mixture was stirred for 1 h before NH$_3$ (30 mL, 2 M in iPrOH, 56.7 mmol) was added. After 1 h of stirring at 25° C., the solution was diluted with CH$_2$Cl$_2$ (200 mL) and washed with NaHSO$_4$ solution, 1 M NaOH, water, dried (Na$_2$SO$_4$) and filtered. The residue was purified over silica gel using 5% MeOH in CH$_2$Cl$_2$ to provide the title compound as a solid.

EXAMPLE 37B

E-4-Amino-adamantane-1-carbonitrile

Step A

The product of Step C of Example 37A, 18.91 mmol) was dissolved in dry CH$_2$Cl$_2$ (60 mL) and Et$_3$N (10.5 mL, 75.64 mmol). TFAA (7.9 mL, 56.73 mmol) was added dropwise to the solution at 0° C. After the addition, the solution was allowed to warm to room temperature and stirred for 3 hours before MeOH was added to quench the reaction. The solution was washed with NaHSO$_4$ solution, NaHCO$_3$ solution, dried (Na$_2$SO$_4$), filtered and concentrated. The residue was purified over silica gel using 30% EtOAc in hexanes and concentrated to yield an oil.

Step B

Pd(OH)$_2$/C (0.9 g) was added to a solution of the product of Step A (3.22 g, 10.38 mmol). The solution was stirred at room temperature under H$_2$ (balloon) until starting material was consumed. The mixture was filtered through a pad of Celite and concentrated in vacuo to provide the title compound as a solid.

EXAMPLE 37C 2-(4-Chloro-phenoxy)-N-[(E)-5-(N-hydroxycarbamimidoyl)-adamantan-2-yl]-2-methyl-propionamide Step A HATU (0.64 g, 1.67 mmol) was added in one portion to a stirred solution of 2-(4-chloro-phenoxy)-2-methyl-propionic acid (0.3 g, 1.50 mmol) and the product of Step B of Example 37B (0.27 g, 1.53 mmol), and DIPEA (0.73 mL, 4.2 mmol) in dry DMF (7 mL). The reaction was allowed to stir for 5 hours before it was diluted with CH$_2$Cl$_2$ and washed with NaHSO$_4$ solution, 1M NaOH, brine, and dried (Na$_2$SO$_4$), and evaporated. The residue was purified over silica gel using 20% EtOAc/hexanes and concentrated to yield a white solid.

Step B

To the product of Step A (87 mg, 0.209 mmol) was added NH$_3$OHCl (87 mg, 1.25 mmol), DIPEA (0.29 mL, 1.67 mmol) and dry DMSO (1 mL). The resulting solution was heated at 80° C. for 8 hrs. The solvent was evaporated and the residue was purified on HPLC using CH$_3$CN/water 1% TFA as eluent to provide the title compound as an oil. $^1$H NMR (300 MHz, CD$_3$OD) δ ppm 7.49-7.54 (m, 1H), 7.26-7.30 (m, 2H), 6.92-6.96 (m, 2H), 3.97-4.03 (m, 1H), 2.10-2.15 (m, 2H), 1.98-2.08 (m, 5H), 1.92-1.94 (m, 2H), 1.76-1.83 (m, 2H), 1.57-1.64 (m, 2H), 1.53 (s, 6H). MS (ESI+) m/z 406.1 (M+H)$^+$.

EXAMPLE 38

E-N-[4-(Aminosulfonyl)benzyl]-4-{[2-(4-chlorophenoxy)-2-methylpropanoyl]amino}adamantane-1-carboxamide The title compound was prepared according to the procedure outlined in Example 24, substituting 4-aminomethyl-benzenesulfonamide hydrochloride for 4-aminomethyl-benzoic acid methyl ester hydrochloride. $^1$H NMR (500 MHz, DMSO-d$_6$) δ ppm 8.10-8.15 (m, 1H), 7.75 (d, J=8.08 Hz, 2H), 7.37 (d, J=8.03 Hz, 2H), 7.31-7.35 (m, 3H), 7.29-7.29 (bs, 2H), 6.91-6.93 (m, 2H), 4.30 (d, J=5.87 Hz, 2H), 3.84-3.88 (m, 1H), 1.93-1.95 (m, 2H), 1.82-1.92 (m, 5H), 1.76-1.78 (m, 2H), 1.67-1.71 (m, 2H), 1.46 (s, 6H), 1.37-1.41 (m, 2H). MS (ESI+) m/z 560 (M+H)$^+$.

EXAMPLE 39

E-4-{[2-(4-Chlorophenoxy)-2-methylpropanoyl]amino}-N-(4-{[(methylsulfonyl)amino]carbonyl}benzyl)adamantane-1-carboxamide To a solution of the product of Example 24 (26 mg, 0.05 mmol) in DMF (1 mL) were added DMAP (7 mg, 0.055 mmol), EDCI (12 mg, 0.06 mmol) and methylsulfonamide (7 mg, 0.075 mmol). The reaction mixture was stirred at room temperature for 72 hours, concentrated in vacuo, and the residue was purified by reverse phase preparative HPLC on a Waters Symmetry C8 column (25 mm×100 mm, 7 um particle size) using a gradient of 10% to 100% acetonitrile:0.1% aqueous TFA over 8 min (10 min run time) at a flow rate of 40 mL/min. to provide the title compound. $^1$H NMR (400 MHz, DMSO-d$_6$) δ ppm 12.01-12.05 (bs, 1H), 8.11 (t, J=6.06 Hz, 1H), 7.87 (d, J=8.19 Hz, 2H), 7.30-7.37 (m, 5H), 6.91-6.93 (m, 2H), 4.31 (d, J=5.89 Hz, 2H), 3.83-3.87 (m, 1H), 3.36 (s, 3H), 1.82-1.96 (m, 7H), 1.77-1.79 (m, 2H), 1.67-1.72 (m, 2H), 1.47 (s, 6H), 1.37-1.42 (m, 2H). MS (ESI+) m/z 602 (M+H)$^+$.

EXAMPLE 40

E-4-({2-[(4-Chlorophenyl)thio]-2-methylpropanoyl}amino)adamantane-1-carboxylic Acid

EXAMPLE 40A

Example 40A was prepared according to the procedure outlined in Example 25A, substituting 4-chloro-benzenethiol for 2,3-dimethylphenol.

EXAMPLE 40B

E-4-({2-[(4-Chlorophenyl)thio]-2-methylpropanoyl}amino)adamantane-1-carboxylic Acid The title compound was prepared according to the procedure outlined in Example 25B, substituting the product of Example 40A for the product of Example 25A. $^1$H NMR (400 MHz, DMSO-d$_6$) δ ppm 7.42-7.45 (m, 2H), 7.36-7.39 (m, 2H), 7.11-7.21 (m, 1H), 3.72-3.78 (m, 1H), 1.91-1.94 (m, 2H), 1.79-1.92 (m, 6H), 1.75-1.80 (m, 3H), 1.44 (s, 8H). MS (ESI+) m/z 408 (M+H)$^+$.

EXAMPLE 41

E-4-({2-[(4-Methoxyphenyl)thio]-2-methylpropanoyl}amino)adamantane-1-carboxamide Amide

EXAMPLE 41A

E-4-(2-Bromo-2-methyl-propionylamino)-adamantane-1-carboxylic Acid

A solution of the product of Example 1B (0.78 g, 2.48 mmol) in 99% formic acid (2.5 mL) was added dropwise with vigorous gas evolution over 10 minutes to a rapidly stirred 30% oleum solution (7.5 mL) heated to 60° C. (W. J. le Noble, S. Srivastava, C. K. Cheung, J. Org. Chem. 48: 1099-1101, 1983). Upon completion of addition, more 99% formic acid (2.5 mL) was slowly added over the next 10 minutes. The mixture was stirred for another 60 minutes at 60° C. and then slowly poured into vigorously stirred iced water (30.0 mL) cooled to 0° C. The mixture was allowed to slowly warm to 23° C., filtered and washed with water to neutral pH (100 mL). The precipitate was dried in a vacuum oven overnight to provide the title compound.

EXAMPLE 41B

E-4-(2-Bromo-2-methyl-propionylamino)-adamantane-1-carboxylic Acid Amide

A solution of the product of Example 41A (250 mg, 0.670 mmol) in DCM (30 mL) was treated with HOBt (109 mg, 0.80 mmol) and EDCI (154 mg, 0.80 mmol) and stirred at room temperature for 3 hour. Excess of aqueous (30%) ammonia (20 mL) was added and the reaction was stirred for additional 20 hours. The layers were separated and the aqueous layer extracted twice more with methylene chloride (2×40 mL). The combined organic extracts were washed with water (3×20 mL) and brine (20 mL); dried (MgSO$_4$) and filtered. The filtrate was concentrated under reduced pressure to provide the crude title compound that was purified by normal phase column chromatography (silica gel, 5% methanol in DCM) to afford the title compound. MS (ESI+) m/z 343 (M+H)$^+$.

EXAMPLE 41C

E-4-[2-(4-Methoxy-phenylsulfanyl)-2-methyl-propionylamino]-adamantane-1-carboxylic Acid Amide A solution of 4-methoxy-benzenethiol (44 mg, 0.31 mmol) and sodium hydride (60%, 15.0 mg, 0.37 mmol) in toluene (4 mL) was stirred at room temperature for 1 hour. The product of Example 41B (106.0 mg, 0.31 mmol) was added to the solution and the resulting mixture was stirred at 100° C. for 24 hours. The reaction mixture was cooled and filtered. The filtrate was concentrated under reduced pressure to provide crude product that was purified by reverse phase preparative HPLC on a Waters Symmetry C8 column (25 mm×100 mm, 7 um particle size) using a gradient of 10% to 100% acetonitrile:0.1% aqueous TFA over 8 min (10 min run time) at a flow rate of 40 mL/min. to afford the title compound. $^1$H NMR (500 MHz, DMSO-d$_6$) δ ppm 7.33-7.35 (m, 2H), 7.11 (d, J=7.18 Hz, 1H), 6.99-7.01 (s, 1H), 6.93-6.95 (m, 2H), 6.72-6.74 (s, 1H), 3.75-3.79 (m, 1H), 3.77 (s, 3H), 1.79-1.95 (m, 9H), 1.75-1.77 (m, 2H), 1.44-1.48 (m, 2H), 1.39 (s, 6H). MS (ESI+) m/z 403 (M+H)$^+$.

EXAMPLE 42

E-4-({2-[(4-Methoxyphenyl)sulfinyl]-2-methylpropanoyl}amino)adamantane-1-carboxamide A solution of the product of Example 41C (53 mg, 0.087 mmol) in methanol (5 mL) was treated with OXONE (80 mg, 0.130 mmol) and stirred at room temperature for 7 hours. The reaction mixture was filtered. The filtrate was concentrated under reduced pressure to provide crude title compound that was subsequently purified by reverse phase preparative HPLC on YMC Guardpak column using a gradient of 0% to 70% acetonitrile:0.1% aqueous TFA over 8 min (10 min run time) at a flow rate of 40 mL/min. to afford the title compound. $^1$H NMR (400 MHz, DMSO-d$_6$) δ ppm 7.49-7.52 (m, 2H), 7.32 (d, J=6.93 Hz, 1H), 7.09-7.12 (m, 2H), 6.96-6.99 (s, 1H), 6.68-6.71 (s, 1H), 3.82 (s, 3H), 3.75-3.81 (m, 1H), 1.89-1.92 (m, 3H), 1.73-1.86 (m, 8H), 1.42-1.51 (m, 2H), 1.34 (s, 3H), 1.25 (s, 3H). MS (ESI+) m/z 419 (M+H)$^+$.

EXAMPLE 43

E-4-({2-[(4-Methoxyphenyl)sulfonyl]-2-methylpropanoyl}amino)adamantane-1-carboxamide A solution of the product of Example 41C (53 mg, 0.087 mmol) in methanol (5 mL) was treated with OXONE (80 mg, 0.130 mmol) and stirred at room temperature for 24 hour. The reaction mixture was filtered. The filtrate was concentrated under reduced pressure to provide crude title compound that was subsequently purified by reverse phase preparative HPLC on a Waters Symmetry C8 column (25 mm×100 mm, 7 um particle size) using a gradient of 10% to 100% acetonitrile:0.1% aqueous TFA over 8 min (10 min run time) at a flow rate of 40 mL/min. to afford the title compound. $^1$H NMR (400 MHz, DMSO-d$_6$) δ ppm 7.72 (d, J=8.65 Hz, 2H), 7.17-7.20 (m, 3H), 6.97-6.99 (s, 1H), 6.70-6.72 (s, 1H), 3.88 (s, 3H), 3.77-3.83 (m, 1H), 1.94-1.97 (m, 3H), 1.82-1.89 (m, 6H), 1.76-1.78 (m, 2H), 1.49-1.54 (m, 2H), 1.45 (s, 6H). MS (ESI+) m/z 435 (M+H)$^+$.

EXAMPLE 44

E-4-({2-[4-Chloro-2-(pyrrolidin-1-ylsulfonyl)phenoxy]-2-methylpropanoyl}amino)adamantane-1-carboxamide

EXAMPLE 44A

2-Hydroxy-5-chlorobenzene Sulfonyl Chloride

4-Chlorophenol (4 g, 31.25 mmol) was added in portions to chlorosulfonic acid (10.3 mL, 156 mmol) while cooling in an ice bath. The resulting solution was stirred at 25° C. for 20 hrs. This was then added drop-wise to ice and water resulting in an emulsion. This was extracted with CHCl$_3$, dried (Na$_2$SO$_4$) and concentrated in vacuo. Heptane was added and evaporated and replaced with cyclohexane. The resulting mixture was filtered and concentrated to give the title compound as an oil (2.16 g).

EXAMPLE 44B

2-Hydroxy-5-chlorobenzene Sulfonyl Pyrrolidine

To a solution of the product of Example 44A (2.16 g, 9.51 mmol) in CHCl$_3$ (8 mL) was added, with ice cooling, pyrrolidine (4.05 g, 57.04 mmol). The mixture was stirred at 25° C. for 2 hrs, then concentrated in vacuo. The residue was dissolved in toluene, washed with HCl and water, dried (Na$_2$SO$_4$) and concentrated. The resulting oil was crystallized from hexane and chromatographed (CH$_2$Cl$_2$) to yield the title compound (1.92 g), m.p. 101-102° C.

EXAMPLE 44C

2-[4-Chloro-2-(pyrrolidine-1-sulfonyl)-phenoxy]-2-methyl-propionic Acid

The product of Example 44B (1.0 g, 3.82 mmol) and 1,1,1-trichloro-2-methyl-2-propanol hydrate (1.832 g, 10.32 mmol) were dissolved in acetone (8.5 mL). Powdered NaOH (0.47 g. 11.75 mmol) was added with cooling. The resulting mixture was stirred for 1.5 hr at 25° C. A second batch of powdered NaOH (0.47 g) was added and stirred for another 1.5 hrs. The last batch of powdered NaOH (0.47 g) was then added along with acetone (2.5 mL). The resulting mixture was stirred for 15 hrs at 25° C. Acetone was added and the solution was filtered. The resulting solution was concentrated. Water (3 mL) was added and concentrated HCl was added to acidify the mixture, which was extracted with toluene, dried and concentrated. The residue was chromatographed on silica gel. Eluting with CH$_2$Cl$_2$ gave 380 mg recovered starting material. Changing to 5% MeOH in ethyl acetate gave the title compound (357 mg, 27% yield).

EXAMPLE 44D

E-4-({2-[4-Chloro-2-(pyrrolidin-1-ylsulfonyl)phenoxy]-2-methylpropanoyl}amino)adamantane-1-carboxamide The product of Example 7B (75 mg, 0.305 mmol), the product of Example 44C (116 mg, 0.335 mmol), and TBTU (108 mg, 0.336 mmol) were suspended in dimethylacetamide (0.5 mL). Diisopropylethylamine (135 mg, 1.05 mmol) was added and the resulting solution stirred at 25° C. for 15 hrs. Toluene was added, and concentrated. More toluene was added, and washed with dil $H_3PO_4$, $H_2O$, and then $KHCO_3$. The organic phase was dried ($Na_2SO_4$), and filtered. The solvents were removed in vacuo and the residue crystallized from ether and heptane to yield the title compound (133 mg), m.p. 152-154° C.

EXAMPLE 44E

E-4-{2-[4-Chloro-2-(pyrrolidine-1-sulfonyl)-phenoxy]-2-methyl-propionylamino}-adamantane-1-carboxylic Acid A solution of the product of Example 44D (125 mg, 0.231 mmol) in MeOH (0.75 mL) was treated with NaOH (100 mg) in water (0.5 mL). The mixture was heated until all was soluble and stirred at 60° C. for 1 hour. The solvent was removed in vacuo and the residue acidified with HCl, extracted with $CHCl_3$, dried ($Na_2SO_4$), filtered, and concentrated. The residue was crystallized from ether to yield the title compound (92 mg, 77% yield), m.p. 226-228° C.

EXAMPLE 44F

E-4-({2-[4-Chloro-2-(pyrrolidin-1-ylsulfonyl)phenoxy]-2-methylpropanoyl}amino)adamantane-1-carboxamide The product of Example 44E (76 mg, 0.145 mmol), TBTU (52 mg, 0.162 mmol), and diisopropylethylamine (40 mg, 0.31 mmol) were dissolved in N,N-dimethylacetamide (0.3 mL). After 25 min. at 25° C., a solution of 10% ammonia in THF was added. A solid formed and the mixture was stirred for 3 hrs at 25° C. Toluene was added and the mixture concentrated in vacuo. The residue was dissolved in $CHCl_3$ and washed with dil $H_3PO_4$, $H_2O$, and $KHCO_3$; dried ($Na_2SO_4$), filtered and concentrated in vacuo. The residue was crystallized from ether to yield the title compound (64 mg, m.p. 249-252° C.). $^1H$ NMR (400 MHz, $CDCl_3$) δ ppm 7.85 (d, J=2 Hz, 1H), 7.37 (dd, J=2, 9 Hz, 1H), 7.25 (d, J=8 Hz, 1H), 7.05 (d, J=9 Hz, 1H), 5.62 (br s 1H), 5.40 (br s, 1H), 3.96 (d, J=8 Hz, 1H), 3.38-3.46 (m, 4H), 1.81-2.03, (m, 9H), 1.86-1.94 (m, 4H), 1.76 (s, 6H), 1.63 (d, J=12 Hz, 2H), 1.44 (d, J=12 Hz, 2H). MS (ESI+) m/z 524, 526 (M+H)$^+$.

EXAMPLE 45

E-4-({2-Methyl-2-[4-(methylsulfonyl)phenoxy] propanoyl}amino)adamantane-1-carboxamide

EXAMPLE 45A

Example 45A was prepared according to the procedure outlined in Example 44C, substituting 4-(methanesulfonyl)-phenol for the product of Example 44B.

EXAMPLE 45B

Example 45B was prepared according to the procedure outlined in Example 44D, substituting the product of Example 45A for the product of Example 44C.

EXAMPLE 45C

Example 45C was prepared according to the procedure outlined in Example 44E, substituting the product of Example 45B for the product of Example 44D.

EXAMPLE 45D

E-4-({2-Methyl-2-[4-(methylsulfonyl)phenoxy] propanoyl}amino)adamantane-1-carboxamide The title compound was prepared according to the procedure outlined in Example 44F, substituting the product of Example 45C for the product of Example 44E. The product had m.p. 217-219° C. $^1H$ NMR (500 MHz, $CDCl_3$) δ ppm 7.85 (d, J=8 Hz, 2H), 7.05 (d, J=8 Hz, 2H), 6.66 (d, J=7 Hz, 1H), 5.65 (br s, 1H), 5.49 (br s 1H), 4.06 (d, J=7 Hz, 1H), 3.05 (s, 3H), 1.86-2.10 (m, 9H), 1.62 (s, 6H), 1.52 (s, 4H). MS (ESI+) m/z 435 (M+H)$^+$.

EXAMPLE 46

E-4-({2-Methyl-2-[2-(methylsulfonyl)phenoxy] propanoyl}amino)adamantane-1-carboxamide

EXAMPLE 46A

2-Methyl-2-(2-methylsulfanyl-phenoxy)-propionic Acid, Ethyl Ester

2-Methylsulfanyl-phenol (2.00 g, 14.29 mmol), 2-bromo-2-methyl-propionic acid, ethyl ester (28 g, 142.8 mmol) and powdered $K_2CO_3$ (4.93 g, 35.7 mmol) were mixed (no solvent) and stirred at 105° C. for 8 hrs. After cooling, water and $CHCl_3$ were added. The $CHCl_3$ was separated, dried ($MgSO_4$) and concentrated. Xylene was added and concentrated in vacuo (4 times) to remove the bromo ester. The resulting oil was chromatographed on silica, eluting with $CH_2Cl_2$ to obtain the title compound (2.30 g, 63% yield).

EXAMPLE 46B

2-Methyl-2-(2-methanesulfonyl-phenoxy)-propionic Acid, Ethyl Ester

To the product of Example 46A (1.00 g, 3.93 mmol) in $CH_2Cl_2$ (15 mL), was added, in portions, 3-chloroperoxybenzoic acid (3.00 g of 70%, 12.16 mmol) while stirring and cooling in a water bath. The mixture was stirred at 25° C. for 20 hrs. Chloroform was added and the mixture was washed with $KHCO_3$, $Na_2S_2O_3$, and again with $KHCO_3$. The solution was dried ($Na_2SO_4$), filtered and concentrated. Heptane was added and concentrated to obtain an oil that solidified (1.22 g, theory=1.142 g).

EXAMPLE 46C

2-Methyl-2-(2-methanesulfonyl-phenoxy)-propionic Acid

The product of Example 46B (1.22 g) was dissolved in MeOH (8 mL) and treated with 50% NaOH (1.75 g, 21.27 mmol) and water (6 mL). The mixture was heated until all was soluble and stirred at 25° C. for 1 hr. The solvents were removed in vacuo, water (6 mL) was added and the solution acidified with HCl. The mixture was extracted with CHCl₃, dried (Na₂SO₄), filtered and concentrated in vacuo. The residue was crystallized from ether and heptane (1:4) to yield the title compound (0.953 g), m.p. 114-116° C.

EXAMPLE 46D

Example 46D was prepared according to the procedure outlined in Example 44D substituting the product of Example 46C for the product of Example 44C.

EXAMPLE 46E

Example 46E was prepared according to the procedures outlined in Example 44E substituting the product of Example 46D for the product of Example 44D.

EXAMPLE 46F

E-4-({2-Methyl-2-[2-(methylsulfonyl)phenoxy]propanoyl}amino)adamantane-1-carboxamide The title compound was prepared according to the procedure outlined in Example 44F, substituting the product of Example 46E for the product of Example 44E. $^1$H NMR (500 MHz, CDCl₃) δ ppm 7.99 (dd, J=7, 2 Hz, 1H), 7.53 (m, 1H), 7.10-7.16 (m, 2H), 5.60 (br s 1H), 5.40 (br s, 1H), 3.95 (d, J=8 Hz, 1H), 3.27 (s, 3H), 1.80-1.96 (m, 9H), 1.55 (d, J=12 Hz, 2H), 1.37 (d, J=12 Hz, 2H). MS (ESI+) m/z 435 (M+H)⁺.

EXAMPLE 47

E-4-[(2-{4-Chloro-2-[(diethylamino)sulfonyl]phenoxy}-2-methylpropanoyl)amino]adamantane-1-carboxamide

EXAMPLE 47A

Example 47A was prepared according to the procedure outlined in Example 44B, substituting diethylamine for pyrrolidine.

EXAMPLE 47B

Example 47B was prepared according to the procedure outlined in Example 44C, substituting the product of Example 47A for the product of Example 44B.

EXAMPLE 47C

Example 47C was prepared according to the procedure outlined in Example 44D, substituting the product of Example 47B for the product of Example 44C.

EXAMPLE 47D

Example 47D was prepared according to the procedure outlined in Example 44E, substituting the product of Example 47C for the product of Example 44D.

EXAMPLE 47E

E-4-[(2-{4-Chloro-2-[(diethylamino)sulfonyl]phenoxy}-2-methylpropanoyl)amino]adamantane-1-carboxamide The title compound was prepared according to the procedure outlined in Example 44F, substituting the product of Example 47D for the product of Example 44E. The compound had m.p. 159-161° C. $^1$H NMR (400 MHz, CDCl₃) δ ppm 7.83 (d, J=2 Hz, 1H), 7.34 (dd, J=2, 9 Hz, 1H), 7.05 (d, J=8 Hz, 1H), 6.98 (d, J=9 Hz, 1H), 5.58 (br s 1H), 5.38 (br s, 1H), 3.95 (d, J=8 Hz, 1H), 3.40 (q, J=7 Hz, 4H), 1.81-1.98, (m, 9H), 1.75 (s, 6H), 1.56 (d, J=12 Hz, 2H), 1.42 (d, J=12 Hz, 2H), 1.17 (t, J=7 Hz, 6H). MS (ESI+) m/z 526, 528 (M+H)⁺.

EXAMPLE 48

E-4-({2-Methyl-2-[4-(pyrrolidin-1-ylsulfonyl)phenoxy]propanoyl}amino)adamantane-1-carboxamide

EXAMPLE 48A 1-(4-Methoxy-benzenesulfonyl)-pyrrolidine

4-Methoxy-benzenesulfonyl chloride (3.00 g, 14.52 mmol) was slowly added to a solution of pyrrolidine (5.15 g, 72.6 mmol) in CHCl₃ (15 mL) with stirring at 0° C. The reaction mixture was allowed to warm up to room temperature and then stirred for 1 hour. After that the reaction mixture was concentrated in vacuo. The residue was dissolved in toluene and washed with aqueous H₃PO₄ solution, and then aqueous KHCO₃ solution. The organic phase was dried with Na₂SO₄, and filtered. The solvents were removed in vacuo and the residue crystallized from ether and heptane to provide the title compound (3.21 g, m.p. 88-89° C.).

EXAMPLE 48B 1-(4-Hydroxy-benzenesulfonyl)-pyrrolidine

The product of Example 48A (3.21 g, 13.3 mmol) was dissolved in CH₂Cl₂ (30 mL), cooled to −78° C. and treated with BBr₃ (8.31 g, 3.26 mmol). The resulting dark red solution was stirred at 25° C. for 4 min, then cooled to −78° C. Methanol (100 mL) was added slowly. The solution was concentrated in vacuo. Toluene was added to the crude and concentrated again. After adding more toluene, the solution was washed with water and concentrated in vacuo. The residue was dissolved in ether and extracted with NaOH (1.0 g) in water (8 mL). The aqueous layer was removed and stirred 15 minutes, then acidified with concentrated HCl. This mixture was extracted with toluene, dried (Na₂SO₄), filtered, concentrated in vacuo and the residue crystallized from ether and heptane (2:1) to provide the title compound (1.063 g, m.p. 122-125° C.).

EXAMPLE 48C

Example 48C was prepared according to the procedure outlined in Example 44C, substituting the product of Example 48B for the product of Example 44B.

EXAMPLE 48D

Example 48D was prepared according to the procedure outlined in Example 44D, substituting the product of Example 48C for the product of Example 44C.

EXAMPLE 48E

Example 48E was prepared according to the procedure outlined in Example 44E, substituting the product of Example 48D for the product of Example 44D.

EXAMPLE 48F

E-4-({2-Methyl-2-[4-(pyrrolidin-1-ylsulfonyl)phenoxy]propanoyl}amino)adamantane-1-carboxamide The title compound was prepared according to the procedure outlined in Example 44F, substituting the product of Example 48E for the product of Example 44E. The compound had m.p. 206-209° C. $^1$H NMR (500 MHz, CDCl$_3$) δ ppm 7.76 (d, J=8 Hz, 2H), 7.02 (d, J=8 Hz, 2H), 6.71 (d, J=8 Hz, 1H), 5.65 (br s, 1H), 5.54 (br s, 1H), 4.067 (d, J=8 Hz, 1H), 3.20-3.26 (m, 4H), 1.86-2.06 (m, 9H), 1.77-1.82 (m, 4H), 1.61 (s, 6H), 1.51 (s, 4H). MS (ESI+) m/z 490 (M+H)$^+$.

EXAMPLE 49

2-(2-Chloro-4-fluorophenoxy)-N-[(E)-5-hydroxy-2-adamantyl]-2-methylpropanamide

EXAMPLE 49A 2-(4-Fluoro-2-chlorophenoxy)-2-methyl-propionic Acid

4-Fluoro-2-chlorophenol (6.00 g, 41.1 mmol) was reacted with 1,1,1-trichloro-2-methyl-2-propanol hydrate (120 g, 12.70 mmol) as described in Example 44C to provide the title compound (6.075 g, 64% yield, m.p. 63-65° C.).

EXAMPLE 49B 2-(2-Chloro-4-fluorophenoxy)-N-[(E)-5-hydroxy-2-adamantyl]-2-methylpropanamide The product of Example 1A (175 mg, 1.05 mmol), 2-(4-fluoro-2-chlorophenoxy)-2-methyl-propionic acid (232 mg, 1.00 mmol), and TBTU (353 mg, 1.1 mmol) were dissolved in N,N-dimethylacetamide. Di-isopropylethylamine (258 mg, 2.0 mmol) was added and the mixture was stirred for 18 hrs at 25° C. After that the reaction mixture was concentrated in vacuo. The residue was dissolved in toluene and washed with aqueous H$_3$PO$_4$ solution, and then aqueous KHCO$_3$ solution. The organic phase was dried with Na$_2$SO$_4$, and filtered. The solvents were removed in vacuo and the residue crystallized from ether and heptane to provide the title compound (262 mg, m.p. 177-179° C.). $^1$H NMR (500 MHz, CDCl$_3$) δ ppm 7.47 (d, J=8 Hz, 1H), 7.18 (dd, J=2, 8 Hz, 1H), 7.08 (dd, J=5 Hz, 8 Hz, 1H), 6.94 (m, 1H), 4.07 (d, J=8 Hz, 1H), 2.12-2.21 (m, 3H), 1.91 (d, J=11 Hz, 2H), 1.70-1.84 (m, 6H), 1.43-1.65 (m, 3H), 1.53 (s, 6H). MS (ESI+) m/z 382, 384 (M+H)$^+$.

EXAMPLE 50

2-(2-Chloro-4-fluorophenoxy)-2-methyl-N-[(E)-5-(2H-tetraazol-5-yl)-2-adamantyl]propanamide

EXAMPLE 50A

Example 50A was prepared according to the procedure outlined in Example 44D, substituting the product of Example 49A for the product of Example 44C.

EXAMPLE 50B

Example 50B was prepared according to the procedure outlined in Example 44E, substituting the product of Example 50A for the product of Example 44D.

EXAMPLE 50C

E-4-[2-(2-Chloro-4-fluorophenoxy)-2-methyl-propionylamino]-adamantane-1-carbonitrile Step A E-4-[2-(2-Chloro-4-fluoro-phenoxy)-2-methyl-propionylamino]-adamantane-1-carboxylic acid amide was prepared according to the procedure outlined in Example 44F, substituting the product of Example 50B for the product of Example 44E.

Step B

The solution of the product of Step A (207 mg, 0.506 mmol) in dioxane (0.5 mL) and pyridine (100 mg) was treated with trifluoroacetic anhydride (167 mg, 0.795 mmol). The mixture was stirred 5 hr at 25° C. and concentrated in vacuo after adding toluene. More toluene was added and the solution was washed with dilute H$_3$PO$_4$, water, and aqueous KHCO$_3$ solution respectively. After drying with Na$_2$SO$_4$, the solution was filtered, concentrated in vacuo and the residue crystallized from ether and heptane to yield the title compound (115 mg, m.p. 159-160° C.).

EXAMPLE 50D 2-(2-Chloro-4-fluorophenoxy)-2-methyl-N-[(E)-5-(2H-tetraazol-5-yl)-2-adamantyl]propanamide A solution of the product of step B of Example 50C (50 mg, 0.128 mmol), trimethyltin chloride (31 mg, 0.153 mmol) and NaN$_3$ (10 mg, 0.153 mmol) in toluene (0.3 mL) was stirred and heated for 64 hrs in a sealed vial at 120° C. The mixture was cooled and 4N HCl in dioxane (1 mL) was added. After stirring 90 min at 25° C. the solution was concentrated in vacuo. Water and HCl were added and the mixture was extracted with CHCl$_3$, dried with Na$_2$SO$_4$, filtered, concentrated and treated with ether to provide the title compound (33 mg, m.p. 256-257° C.). $^1$H NMR (400 MHz, DMSO-d$_6$) δ ppm 7.52 (d, J=8 Hz, 1H), 7.15-7.23 (m, 2H), 3.98 (d, J=8 Hz 1H), 1.98-2.12 (m, 9H), 1.90 (d, J=13 Hz, 2H), 1.60 (d, J=13 Hz, 2H), 1.46 (s, 6H). MS (ESI+) m/z 434, 435 (M+H)$^+$.

EXAMPLE 51

2-(2-Chloro-4-fluorophenoxy)-2-methyl-N-[(E)-5-(methylthio)-2-adamantyl]propanamide A solution of the product of Example 49B (150 mg, 0.392 mmol) in CF$_3$COOH (750 mg) was treated with trifluoroacetic anhydride (375 mg, 1.78 mmol) for 5 min. Then, CF$_3$COOH (1.68 g, 14.9 mmol) and NaSCH$_3$ (549 mg, 7.8 mmols) were added to the 7 mL sealed tube. This mixture was heated at 120° C. for 20 hrs. After cooling, toluene was added, and the mixture concentrated in vacuo. More toluene was added and this was shaken with K$_2$CO$_3$ solution. The toluene layer was separated, dried (Na$_2$SO$_4$), concentrated and chromatographed in 4% EtOAc in DCM to give the title compound (132 mg, m.p. 100-101° C.). $^1$H NMR (400 MHz, CDCl$_3$) δ ppm 7.50 (d, J=8 Hz, 1H), 7.17 (dd, J=2, 8 Hz, 1H), 7.08 (dd, J=5, 8 Hz, 1H), 6.93 (m, 1H), 4.07 (d, J=8 Hz, 1H), 1.82-2.15 (m, 9H), 2.03 (s, 3H), 1.82 (d, J=13 Hz, 2H), 1.59 (d, J=13 Hz, 2H), 1.54 (s, 6H), MS (ESI+) m/z 412, 414 (M+H)$^+$.

EXAMPLE 52

2-(2-Chloro-4-fluorophenoxy)-2-methyl-N-[(E)-5-(methylsulfonyl)-2-adamantyl]propanamide A solution of the product of Example 51 (100 mg, 0.235 mmol) in CH$_2$Cl$_2$ (1 ml) was treated with 3-chloroperbenzoic acid (180 mg, 70%, 1.05 mmol). After stirring for 17 hrs at 25° C., CHCl$_3$ was added to the reaction mixture and the solution was extracted with KHCO$_3$, Na$_2$S$_2$O$_3$, and KHCO$_3$. After drying (Na$_2$SO$_4$), filtered and concentrating, the residue was crystallized from heptane and ether to provide the title compound (89 mg, m.p. 172-173° C.). $^1$H NMR (400 MHz, CDCl$_3$) δ ppm 7.55 (d, J=8 Hz, 1H), 7.18 (dd, J=2, 8 Hz, 1H), 7.09 (dd, J=5, 8 Hz, 1H), 6.95 (m, 1H), 4.09 (d, J=8 Hz, 1H), 2.76 (s, 3H), 2.07-2.25 (m, 9H), 1.90 (d, J=13 Hz, 2H), 1.65 (d, J=13 Hz, 2H), 1.54 (s, 6H). MS (ESI+) m/z 444, 446 (M+H)$^+$.

EXAMPLE 53

2-(2-Chloro-4-fluorophenoxy)-2-methyl-N-[(E)-5-(methylsulfinyl)-2-adamantyl]propanamide A-solution of the product of Example 51 (71 mg, 0.172 mmol) in acetic acid (75 mL) was prepared. Sodium perborate (NaBO$_3$.H$_2$O, 18 mg, 0.18 mmol) was added and the mixture was stirred 16 hr at 25° C. Toluene was added. The mixture was concentrated and more toluene added. This was washed with K$_2$CO$_3$, dried (Na$_2$SO$_4$), filtered, and concentrated in vacuo. The residue was crystallized from ether to get the title compound (44 mg, m.p. 134-135° C.). $^1$H NMR (500 MHz, CDCl$_3$) δ ppm 7.58 (d, J=8 Hz, 1H), 7.19 (dd, J=2, 8 Hz, 1H), 7.10 (dd, J=5, 8 Hz, 1H), 6.95 (m, 1H), 4.10 (d, J=8 Hz, 1H), 2.42 (s, 3H), 2.17-2.30 (m, 3H), 2.01 (d, J=13 Hz, 2H), 1.82-2.05 (m, 6H), 1.55 (d, J=13 Hz, 2H), 1.54 (s, 6H). MS (ESI+) m/z 428, 430 (M+H)$^+$.

EXAMPLE 54

N-[(E)-5-(Aminosulfonyl)-2-adamantyl]-2-(4-chlorophenoxy)-2-methylpropanamide

EXAMPLE 54A

1-Bromoadaman-4-one

5-Hydroxy-2-adamantanone (5.00 g, 30.1 mmol) was mixed with 48% hydrobromic acid (50 mL) and heated at 100° C. for 48 hours (H. W. Geluk, J. L. M. A. Schlatmann, Tetrahedron 24: 5369-5377, 1968). Reaction diluted with water and extracted twice with ether. Combined extracts dried (Na$_2$SO$_4$), decanted, and evaporated under reduced pressure. The residue was purified on normal phase HPLC (silica gel, 5-10% ethyl acetate in hexane) to provide the title compound (4.19 g, 61%).

EXAMPLE 54B

1-Bromoadamantan-4-one Ethylene Ketal

The product of Example 54A (4.19 g, 18.3 mmol), ethylene glycol (2.05 mL, 36.6 mmol), and a catalytic amount of p-toluenesulfonic acid (20 mg) were dissolved in benzene (100 mL) and heated at reflux with a Dean-Stark apparatus attached for 16 hours (M. Xie, W. J. le Noble, J. Org. Chem. 54: 3836-3839, 1989). The reaction was cooled, washed with 2N sodium carbonate, water, and brine. The organic solution was dried (Na$_2$SO$_4$), filtered, and evaporated under reduced pressure to provide the title compound.

EXAMPLE 54C (1R,2S)-1-Amino-2-indanol-N-4-toluene Sulfonamide (1R,2S)-Aminoindanol (5.00 g, 33.5 mmol) and ethyl acetate (75 mL) were added to a solution of sodium carbonate (6.89 g, 65.0 mmol) in water (30 mL) that had been stirring at room temperature for 20 minutes. After stirring this mixture for 20 minutes, a solution of p-toluenesulfonyl chloride (6.20 g, 32.5 mmol) in 1:1 THF/ethyl acetate (12 mL) was added drop-wise using an addition funnel over a period of 20 minutes (Z. Han, D. Krishnamurthy, P. Grover, Q. K. Fang, C. H. Senanayake, J. Am. Chem. Soc. 124: 7880-7881, 2002). Reaction stirred 16 hours at room temperature. Stirring was stopped, and the layers separated. The organic phase was washed with water, 1N hydrochloric acid, and brine. The organic solution was dried (Na$_2$SO$_4$), filtered, and evaporated under reduced pressure to provide the title compound.

EXAMPLE 54D (2R,4R,5S)-3-(4-Toluenesulfonyl)-3,3a,8,8a-tetrahydro-1-oxa-2-thia-3-aza-cyclopenta[a]indene-2-oxide and (2S,4R,5S)-3-(4-Toluenesulfonyl)-3,3a,8,8a-tetrahydro-1-oxa-2-thia-3-aza-cyclopenta[a]indene-2-oxide A solution of the product of Example 54C (10.2 g, 33.5 mmol) at −45° C. in anhydrous THF (50 mL) was treated slowly, in one portion, with thionyl chloride (3.67 mL, 50.3 mmol). A solution of imidazole (6.84 g, 101 mmol) in anhydrous THF (50 mL) was then added drop-wise to this solution over 40 minutes using an addition funnel (Z. Han, D. Krishnamurthy, P. Grover, Q. K. Fang, C. H. Senanayake, J. Am. Chem. Soc. 124: 7880-7881, 2002). Reaction stirred two hours at −45° C. and was then quenched at −45° C. with saturated sodium bicarbonate. The mixture was then diluted with ethyl acetate and warmed to room temperature with stirring. The layers were allowed to separate and the organic phase was washed with water and brine. The organic solution was dried (Na$_2$SO$_4$), filtered, and evaporated under reduced pressure to provide the title compounds.

EXAMPLE 54E (S)-(4-Adamantanone ethylene ketal)-1-sulfinic acid-(1R,2S)-1-(4-toluenesulfonylamino)-indan-2-yl ester and (R)-(4-Adamantanone ethylene ketal)-1-sulfinic acid-(1R,2S)-1-(4-toluenesulfonylamino)-indan-2-yl Ester A 0.76M solution of Rieke Zinc (57 mL, 43.0 mmol) in THF was added at room temperature to a degassed solution under nitrogen containing the product of Example 54B (7.82 g, 28.6 mmol) in anhydrous THF (10 mL). Reaction stirred 16 hours at room temperature. More 0.76M Rieke Zinc (50 mL, 38.0 mmol) in THF was added, and reaction mixture stirred an additional 20 hours. This reaction mixture containing the zinc bromide was added drop-wise using a cannule to a −45° C. solution under nitrogen of the product of Example 54D (6.66 g, 19.1 mmol) in anhydrous THF (10 mL). Reaction stirred 16 hours at room temperature. Reaction mixture diluted with ethyl acetate, washed with brine, dried ($Na_2SO_4$), filtered, and evaporated under reduced pressure. The residue was purified on normal phase HPLC (silica gel, 30-40% ethyl acetate in hexane) to provide the title compound.

EXAMPLE 54F 1-((S)-Aminosulfinyl)adamantan-4-one ethylene ketal and 1-((R)-Aminosulfinyl)adamantan-4-one Ethylene Ketal A three-necked flask under argon equipped with a glass stir bar, a thermometer, a gas inlet, and an ammonia condenser (−78° C.) in a −50° C. bath was charged with anhydrous liquid ammonia (40 mL). A few crystals of iron nitrate nonahydrate (5 mg) were added to the ammonia, followed by portion-wise addition of lithium wire (650 mg, 93.7 mmol) in a controlled manner keeping the internal temperature at about −45° C. When all the lithium was added and the blue solution became a grey suspension, the mixture was stirred for an additional two hours at −45° C. The mixture was then cooled to −78° C., and a solution of the product of Example 54E (7.00 g, 12.9 mmol) in anhydrous THF (30 mL) was added drop-wise over a period of 30 minutes. Reaction mixture stirred 2 hours at −78° C. and then quenched with saturated ammonium chloride. Reaction mixture allowed to warm to room temperature, and product extracted with ethyl acetate. Extracts washed with brine, dried ($Na_2SO_4$), filtered, and evaporated under reduced pressure. The residue was purified on normal phase HPLC (silica gel, 5% methanol in ethyl acetate) to provide the title compound (1.19 g, 36%).

EXAMPLE 54G

1-Aminosulfonyladamantan-4-one Ethylene Ketal

A solution of the product of Example 54F (1.19 g, 4.63 mmol) in anhydrous THF (10 mL) at room temperature was treated with a 2.5 wt. % solution of osmium tetroxide (0.35 mL) in 2-propanol and 4-methylmorpholine N-oxide (0.55 g, 4.67 mmol). Reaction stirred at room temperature for 16 hours. Reaction diluted with ethyl acetate, washed with water and brine, dried ($Na_2SO_4$), filtered, and evaporated under reduced pressure to provide the title compound.

EXAMPLE 54H

1-Aminosulfonyladamantan-4-one

A solution of the product of Example 54G (1.26 g, 4.63 mmol) in THF (15 mL) at room temperature was treated with 1N hydrochloric acid (14 mL). Reaction heated at 60° C. for 16 hours. Reaction quenched with saturated sodium bicarbonate, and product extracted with 20% methanol in chloroform (2×) and 40% THF in DCM (2×). Extracts dried ($Na_2SO_4$), filtered, and evaporated under reduced pressure to provide the title compound (0.880 g, 82%).

EXAMPLE 54I

E-4-Amino-adamantane-1-sulfonic Acid Amide

The title compound was prepared according to the procedure outlined in Example 7A substituting the product of Example 54H for 4-oxo-adamantane-1-carboxylic acid.

EXAMPLE 54J

N-[(E)-5-(Aminosulfonyl)-2-adamantyl]-2-(4-chlorophenoxy)-2-methylpropanamide

The product of Example 54I (100 mg, 0.44 mmol), 2-(4-chlorophenoxy)-2-methylpropionic acid (93 mg, 0.44 mmol), and TBTU (209 mg, 0.65 mmol) were mixed in DMF (2 mL) at room temperature for 10 minutes. N,N-diisopropylethylamine (0.15 mL, 0.87 mmol) was added to this solution, and the reaction stirred 16 hours at room temperature. Reaction was diluted with ethyl acetate, washed with water, saturated sodium bicarbonate, 1N phosphoric acid, and brine. Organic phase dried ($Na_2SO_4$), filtered, and evaporated under reduced pressure. The residue was purified by flash chromatography on silica gel (20-30% ethyl acetate in hexane) to provide the title compound. $^1$H NMR (500 MHz, DMSO-$d_6$) δ ppm 7.43 (d, J=6 hz, 1H) 7.33 (d, J=8 Hz, 2H) 6.91 (d, J=8 Hz, 2H) 6.58 (s, 2H) 3.79 (m, 1H) 2.04 (bs, 2H) 2.00-1.80 (m, 7H) 1.71 (m, 2H) 1.46 (s, 6H) 1.35 (m, 2H). MS (ESI+) m/z 427 (M+H)$^+$.

EXAMPLE 55

E-4-({[1-(4-Chlorophenoxy)cyclobutyl]carbonyl}amino)adamantane-1-carboxamide

EXAMPLE 55A

Ethyl 1-(4-chlorophenoxy)cyclobutanecarboxylic Acid

A mixture of p-chlorophenol (621 mg, 4.83 mmol), ethyl 1-bromocyclobutanecarboxylate (1.0 g, 4.83 mmol) and potassium carbonate (1.33 g, 9.66 mmol) in DMF (14.5 ml) was stirred and heated to about 55-60° C. under a nitrogen atmosphere for about 18 hours. The solvent was removed under high vacuum, the residue was taken up in diethyl ether (50 ml) and was washed with water and brine (15 ml each). The organic layer was dried (MgSO$_4$), and filtered. The solvent was removed under vacuum and the residue was purified by flash column chromatography on silica gel using hexanes/ ethyl acetate (2:1) as the mobile phase to provide 320 mg (26%) of the title compound. MS (DCI): m/z 272 (M+NH$_4$)$^+$.

EXAMPLE 55B 1-(4-Chlorophenoxy)cyclobutanecarboxylic Acid

To the product of Example 55A (320 mg, 1.26 mmol) was added glacial acetic acid (10 ml) followed by 5% aqueous hydrochloric acid (2.5 ml) and the mixture was heated to reflux for about 18 hours. The mixture was cooled and was evaporated to dryness. The residue was taken up in toluene and was evaporated to dryness two times to provide 250 mg (87%) of the title compound. MS (DCI): m/z 244 (M+NH$_4$)$^+$.

EXAMPLE 55C

E-4-({[1-(4-Chlorophenoxy)cyclobutyl]carbonyl}amino)adamantane-1-carboxylic Acid Methyl Ester A mixture of the product of Example 55B (207 mg, 0.81 mmol), the product of Example 7B (200 mg, 0.81 mmol), O-benzotriazol-1-yl-N,N,N',N'-tetramethyluronium tetrafluoroborate (523 mg, 1.63 mmol) and N,N-diisopropylethylamine (0.57 ml, 3.26 mmol) in DMF (11 ml) was stirred at ambient temperature under a nitrogen atmosphere for about 18 hours. The solvent was evaporated in high vacuum and the residue was purified by flash column chromatography on silica gel using hexanes/ethyl acetate (2:1) as the mobile phase to provide 240 mg (70%) of the title compound. MS (DCI) m/z 418 (M+H)$^+$.

EXAMPLE 55D

E-4-({[1-(4-Chlorophenoxy)cyclobutyl]carbonyl}amino)adamantane-1-carboxylic Acid To a solution of the product of Example 55C (240 mg, 0.57 mmol) in dioxane (8 ml) was added 2N aqueous hydrochloric acid (8 ml) and the mixture was heated to about 60° C. for about 18 hours. The mixture was cooled and concentrated in vacuo down to the water phase. The precipitate was filtered off and was dried under high vacuum to provide 200 mg (86%) of the title compound. MS (DCI) m/z 404 (M+H)$^+$.

EXAMPLE 55E

E-4-({[1-(4-Chlorophenoxy)cyclobutyl]carbonyl}amino)adamantane-1-carboxamide

A solution of the product of Example 55D (200 mg, 0.5 mmol), N-(3-dimethylaminopropyl)-N'-ethylcarbodiimide hydrochloride (380 mg, 2.0 mmol) and 1-hydroxybenzotriazole hydrate (217 mg, 1.61 mmol) in dichloromethane (17 ml) was stirred at ambient temperature under a nitrogen atmosphere for about 1 hour. A 0.5 M solution of ammonia in dioxane (9.9 ml, 4.95 mmol) was added and stirring was continued for about 2 hours. Ammonium hydroxide (8.5 ml) was added to the reaction mixture and stirring was continued for about 2 hours. The mixture was diluted with dichloromethane (55 ml), the layers were separated, the organic layer was dried (MgSO$_4$), filtered, and was evaporated in vacuo. The residue was purified by flash column chromatography on silica gel using dichloromethane/methanol (15:1) as the mobile phase to provide 113 mg (57%) of the title compound. $^1$H NMR (400 MHz, DMSO-d$_6$) δ ppm 7.33-7.29 (m, 2H), 7.08-7.07 (m, 1H), 6.92 (bs, 1H), 6.74-6.70 (m, 2H), 6.66 (bs, 1H), 3.76-3.74 (m, 1H), 2.68-2.62 (m, 2H), 2.33-2.25 (m, 2H), 1.89-1.64 (m, 11H), 1.37-1.34 (m, 2H), 1.22-1.19 (m, 2H). MS (ESI+) m/z 403 (M+H)$^+$.

EXAMPLE 56

4-[({[((E)-4-{[2-(4-Chlorophenoxy)-2-methylpropanoyl]amino}-1-adamantyl)methyl]sulfonyl}amino)methyl]benzoic Acid Step A To a solution of the product of Example 36B (395 mg, 0.895 mmol) in DCM (8.9 mL) and DMF (1 drop) was added triphosgene (194 mg, 0.653 mmol) and triethylamine (0.125 mL, 0.895 mmol). The resulting reaction mixture was stirred at room temperature for 1.5 hours and then one half of the solution was added dropwise to a solution of methyl 4-(aminomethyl)-benzoate hydrochloride (67.6 mg, 0.447 mmol) and triethylamine (0.16 mL, 1.12 mmol) in DCM (1.0 mL). After stirring at room temperature overnight, the reaction was quenched with water and extracted with EtOAc. The organic layer was then rinsed with brine, dried over Na$_2$SO$_4$, filtered, and concentrated in vacuo.

Step B

The product of Step A was dissolved in a mixture of THF, water, and ethanol and treated with excess NaOH. After stirring at room temperature overnight the reaction was concentrated in vacuo. The crude product was purified by reverse phase preparative HPLC using acetonitrile: 10 mM NH$_4$OAc on YMC Guardpak column to provide the title compound (25 mg, 10%). $^1$H NMR (500 MHz, CDCl$_3$) δ ppm 8.06 (d, J=8.6 Hz, 2H), 7.44 (d, J=8.6 Hz, 2H), 7.24 (d, J=8.6 Hz, 2H), 6.98 (d, J=8.2 Hz, 1H), 6.86 (d, J=8.6 Hz, 2H), 4.92 (m, 1H), 4.37 (d, J=5.5 Hz, 2H), 4.03 (m, 1H), 2.83 (s, 2H), 1.50-2.17 (m, 11H), 1.50 (s, 6H). MS (ESI+) m/z 575 (M+H)$^+$.

EXAMPLE 57

2-(4-Chlorophenoxy)-N-[(E)-5-(1H-imidazol-2-yl)-2-adamantyl]-2-methylpropanamide The product of Example 33B (0.1 g, 0.266 mmol) and glyoxal (0.11 g, 40 wt % in water, 0.8 mmol) was dissolved in ammonia solution (6 mL, 7 N). The reaction vessel was sealed and stirred at room temperature for 1 day. The volatiles were evaporated and the residue was purified by reverse phase HPLC using CH$_3$CN/0.1% TFA in water to provide the title compound as an oil. $^1$H NMR (300 MHz, CD$_3$OD) δ ppm 1.48-1.59 (s, 6H) 1.60-1.73 (m, 2H) 1.77-1.94 (m, 2H) 2.02-2.12 (m, 3H) 2.12-2.27 (m, 6H) 4.01-4.12 (m, 1H) 6.88-7.02 (m, 2H) 7.21-7.35 (m, 2H) 7.44-7.49 (m, 2H) 7.49-7.60 (m, 1H). MS (ESI+) m/z 414.1 (M+H)$^+$.

EXAMPLE 58

(2E)-3-((E)-4-{[2-(4-Chlorophenoxy)-2-methylpropanoyl]amino}-1-adamantyl)acrylic Acid

EXAMPLE 58A (2E)-3-((E)-4-{[2-(4-Chlorophenoxy)-2-methylpropanoyl]amino}-1-adamantyl)acrylic Acid Ethyl Ester To a cold (0° C.) solution of triethyl phosphonoacetate (0.22 ml, 1.1 mmol) in DME (1.0 mL) was added NaH (60% in oil, 42 mg, 1.1 mmol) under N$_2$ flow. The reaction mixture was stirred for 10 minutes and a solution of the product of Example 33B (375 mg, 1 mmol) in DME (0.2 ml) was added slowly at 0° C. It was allowed to warm up to room temperature and stirred for 5 hours. It was quenched with water and extracted with DCM 3 times. The combined organic layer was dried over Na$_2$SO$_4$, filtered, concentrated under reduced pressure and purified by flash chromatography with 30% ethyl acetate/70% hexane to provide the title compound, 350 mg (79%). $^1$H NMR (300 MHz, CDCl$_3$) δ ppm 7.20-7.26 (m, 2H), 6.94-7.03 (m, 1H), 6.84-6.91 (m, 2H), 6.80 (d, 1H), 5.69 (d, 1H), 4.19 (q, 2H), 3.98-4.08 (m, 1H), 1.91-2.08 (m, 3H), 1.46-1.83 (m, 16H), 1.29 (t, 3H). %). MS (ESI+) m/z 446 (M+H)$^+$.

EXAMPLE 58B (2E)-3-((E)-4-{[2-(4-Chlorophenoxy)-2-methylpropanoyl]amino}-1-adamantyl)acrylic Acid To a solution of the product of Example 58A (45 mg, 0.1 mmol) in THF/water (0.1 ml/0.05 ml) was added LiOH.H$_2$O (26 mg, 0.6 mmol). It was stirred at room temperature overnight. It was acidified with 1N HCl and extracted with DCM 3 times. The combined organic layer was dried over Na$_2$SO$_4$, filtered, concentrated under reduced pressure and purified by flash chromatography with 30% ethyl acetate/70% hexane to provide the title compound 35 mg (83%). $^1$H NMR (400 MHz, CDCl$_3$) δ ppm 7.20-7.28 (m, 2H), 6.96-7.04 (m, 1H), 6.82-6.95 (m, 3H), 5.70 (d, 1H), 4.00-4.09 (m, 1H), 1.93-2.08 (m, 3H), 1.47-1.85 (m, 16H). MS (ESI+) m/z 418 (M+H)$^+$.

EXAMPLE 59

(E)-4-[(2-Methyl-2-{[5-(1H-pyrazol-1-yl)pyridin-2-yl]oxy}propanoyl)amino]adamantane-1-carboxamide CuI (10.5 mg, 0.055 mmol), N,N,-dimethylglycine (11.3 mg, 0.109 mmol), K$_2$CO$_3$ (76 mg, 0.549 mmol), pyrazole (22 mg, 0.329 mmol), and the product of step C of Example 30B (80 mg, 0.183 mmol) was dissolved in DMSO (1 mL) and the resulting mixture was heated in Personal Chemistry's Emry Optimizer microwave instrument at 160° C. for 20 minutes. The mixture was diluted with EtOAc and filtered through a pad of silica and after evaporation the residue was purified by reverse phase HPLC using CH$_3$CN/0.1% TFA in water to give the title compound. $^1$H NMR (300 MHz, CD$_3$OD) δ ppm 1.40-1.64 (m, 4H) 1.66-1.76 (m, 7H) 1.77-1.87 (m, 3H) 1.90-2.04 (m, 7H) 3.93 (s, 1H) 6.53 (dd, J=2.54, 1.86 Hz, 1H) 7.01 (d, J=8.82 Hz, 1H) 7.72 (d, J=2.03 Hz, 1H) 8.07 (dd, J=8.99, 2.88 Hz, 1H) 8.15 (d, J=3.05 Hz, 1H) 8.45 (d, J=2.71 Hz, 1H) 8.45 (d, J=2.71 Hz, 1H). MS (ESI+) m/z 424.2 (M+H)$^+$.

EXAMPLE 60

2-(4-Chlorophenoxy)-N-[(E)-5-isoxazol-5-yl-2-adamantyl]-2-methylpropanamide

EXAMPLE 60A 2-(4-Chlorophenoxy)-2-methyl-N-[(E)-5-propynoyl-adamantan-2-yl]-propionamide Step A
Acetylenemagnesium chloride (8.22 mL, 0.5 M in THF, 4.11 mmol) was added dropwise to a stirred and cooled (−78° C.) solution of the product of Example 33B (0.514 g, 1.37 mmol) in dry THF. The resulting solution was warmed gradually to room temperature before it was quenched with saturated NH$_4$Cl solution. The mixture was partitioned with Et$_2$O and water. The organic phase was washed with brine, dried (MgSO$_4$), filtered, and evaporated to give crude alcohol as an oil.

Step B
Dess-Martin periodinane (1 g, 2.43 mmol) was added in one portion to a solution of the product of Step A (0.65 g, 1.62 mmol) in dry CH$_2$Cl$_2$. The resulting solution was stirred for 3 hours at room temperature before it was quenched with saturated NaHCO$_3$ solution and Na$_2$S$_2$O$_3$ solution. The mixture was stirred for 1 hour before the phases were separated. The organic phase was dried (Na$_2$SO$_4$), filtered, and the solvent was evaporated. The residue was purified over silica gel using 30% EtOAc in hexanes to provide the title compound as a yellow solid.

EXAMPLE 60B 2-(4-Chlorophenoxy)-N-[(E)-5-isoxazol-5-yl-2-adamantyl]-2-methylpropanamide NH$_2$OH.HCl (0.23 g, 2.75 mmol) and K$_2$CO$_3$ (0.38 g, 2.75 mmol) was added to a solution of the product of Step B of Example 60A (0.11 g, 0.275 mmol) in isopropanol. The reaction was heated (80° C.) for 3 hours. The reaction mixture was diluted with EtOAc and filtered through a pad of Celite and after evaporation the residue was purified by reverse phase HPLC using CH$_3$CN/0.1% TFA in water to provide the title compound. $^1$H NMR (300 MHz, CD$_3$OD) δ ppm 1.53 (s, 6H) 1.65 (d, 2H) 1.91-2.04 (m, 4H) 2.11 (s, 6H) 4.06 (d, J=7.46 Hz, 1H) 6.12 (d, J=2.03 Hz, 1H) 6.96 (d, J=8.82 Hz, 2H) 7.29 (d, J=9.16 Hz, 2H) 7.48 (d, J=6.78 Hz, 1H) 8.25 (d, J=2.03 Hz, 1H). MS (ESI+) m/z 415.1 (M+H)$^+$.

EXAMPLE 61

2-(4-Chlorophenoxy)-2-methyl-N-{(E)-5-[(2-morpholin-4-ylethoxy)methyl]-2-adamantyl}propanamide A solution of the product of Example 33A (61 mg, 0.16 mmol) and 4-(2-Chloro-ethyl)-morpholine hydrochloride (36 mg, 0.19 mmol) in DMF (4 mL) was treated with sodium hydride (60%, 20.0 mg, 0.5 mmol) and was stirred at 100° C. for 24 hours. Then the reaction mixture was cooled and filtered. The filtrate was concentrated under reduced pressure to provide crude title compound that was purified by reverse phase preparative HPLC using acetonitrile: 10 mM NH$_4$OAc on YMC Guardpak column to afford the title compound. $^1$H NMR (500 MHz, CD$_3$OD) δ ppm 7.41 (s, 1H) 7.26-7.30 (m, 2H) 6.93-6.96 (m, 2H) 3.92 (s, 1H) 3.66-3.72 (m, 4H) 3.56 (t, J=5.49 Hz, 2H) 3.03 (s, 2H) 2.59 (t, J=5.49 Hz, 2H) 2.52-2.57 (m, 4H) 1.96 (d, J=2.14 Hz, 2H) 1.86 (s, 1H) 1.72 (s, 1H) 1.69 (s, 1H) 1.67 (s, 4H) 1.57 (d, J=3.36 Hz, 2H) 1.53 (s, 2H) 1.51 (s, 6H). MS (ESI+) m/z 491 (M+H)$^+$.

EXAMPLE 62

N-[(E)-5-(Aminosulfonyl)-2-adamantyl]-2-(2-chlorophenoxy)-2-methylpropanamide

EXAMPLE 62A 2-(2-Chlorophenoxy)-2-methylpropionic Acid

The title compound was prepared according to the procedure outlined in Example 44C substituting 2-chlorophenol for the product of Example 44B.

EXAMPLE 62B

N-[(E)-5-(Aminosulfonyl)-2-adamantyl]-2-(2-chlorophenoxy)-2-methylpropanamide

The title compound was prepared according to the procedure outlined in Example 54J substituting the product of Example 62A for 2-(4-chlorophenoxy)-2-methylpropionic acid. $^1$H NMR (400 MHz, CDCl$_3$) δ ppm 7.61 (d, J=8 Hz, 1H), 7.42 (dd, J=8 & 2 Hz, 1H), 7.21 (m, 1H), 7.13 (dd, J=8 & 2 Hz, 1H), 7.05 (m, 1H), 4.32 (s, 2H), 4.09 (m, 1H), 2.30-2.10 (m, 8H), 1.90 (m, 2H), 1.60 (m, 3H), 1.46 (s, 6H). MS (ESI+) m/z 427 (M+H)$^+$.

EXAMPLE 63

N-[(E)-5-(Aminosulfonyl)-2-adamantyl]-2-methyl-2-(2-methylphenoxy)propanamide

EXAMPLE 63A

2-Methyl-2-(2-methylphenoxy)propionic Acid

The title compound was prepared according to the procedure outlined in Example 44C, substituting 2-methylphenol for the product of Example 44B.

EXAMPLE 63B

N-[(E)-5-(Aminosulfonyl)-2-adamantyl]-2-methyl-2-(2-methylphenoxy)propanamide

The title compound was prepared according to the procedure outlined in Example 54J substituting the product of Example 63A for 2-(4-chlorophenoxy)-2-methylpropionic acid. $^1$H NMR (400 MHz, CDCl$_3$) δ ppm 7.19 (dd, J=8 & 2 Hz, 1H), 7.14 (d, J=8 Hz, 1H), 7.09 (m, 1H), 6.96 (m, 1H), 6.86 (dd, J=8 & 2 Hz, 1H), 4.33 (s, 2H), 4.09 (m, 1H), 2.28 (s, 3H), 2.30-2.05 (m, 8H), 1.71 (m, 2H), 1.59 (m, 3H), 1.52 (s, 6H). MS (ESI+) m/z 407 (M+H)$^+$.

EXAMPLE 64

N-[(E)-5-(Aminosulfonyl)-2-adamantyl]-2-methyl-2-(4-methylphenoxy)propanamide

EXAMPLE 64A

2-Methyl-2-(4-methylphenoxy)propionic Acid

The title compound was prepared according to the procedure outlined in Example 44C, substituting 4-methylphenol for the product of Example 44B.

EXAMPLE 64B

N-[(E)-5-(Aminosulfonyl)-2-adamantyl]-2-methyl-2-(4-methylphenoxy)propanamide

The title compound was prepared according to the procedure outlined in Example 54J substituting the product of Example 64A for 2-(4-chlorophenoxy)-2-methylpropionic acid. $^1$H NMR (400 MHz, CDCl$_3$) δ ppm 7.14 (d, J=8 Hz, 2H), 7.08 (d, J=8 Hz, 2H), 6.82 (d, J=8 Hz, 1H), 4.46 (s, 2H), 4.06 (m, 1H), 2.31 (s, 3H), 2.30-2.00 (m, 8H), 1.72 (m, 2H), 1.59 (m, 3H), 1.49 (s, 6H). MS (ESI+) m/z 407 (M+H)$^+$.

EXAMPLE 65

N-[(E)-5-(Aminosulfonyl)-2-adamantyl]-2-methyl-2-[2-(trifluoromethyl)phenoxy]propanamide

EXAMPLE 65A

2-Methyl-2-(2-trifluoromethylphenoxy)propionic Acid

The title compound was prepared according to the procedure outlined in Example 44C, substituting 2-trifluoromethylphenol for the product of Example 44B.

EXAMPLE 65B

N-[(E)-5-(Aminosulfonyl)-2-adamantyl]-2-methyl-2-[2-(trifluoromethyl)phenoxy]propanamide The title compound was prepared according to the procedure outlined in Example 54J substituting the product of Example 65A for 2-(4-chlorophenoxy)-2-methylpropionic acid. $^1$H NMR (400 MHz, CDCl$_3$) δ ppm 7.61 (dd, J=8 & 2 Hz, 1H), 7.45 (m, 1H), 7.11 (m, 2H), 7.01 (d, J=8 Hz, 1H), 4.42 (s, 2H), 4.06 (m, 1H), 2.30-2.05 (m, 8H), 1.70 (m, 3H), 1.64 (s, 6H), 1.55 (m, 2H). MS (ESI+) m/z 461 (M+H)$^+$.

EXAMPLE 66

N-[(E)-5-(Aminosulfonyl)-2-adamantyl]-2-methyl-2-[2-(trifluoromethoxy)phenoxy]propanamide

EXAMPLE 66A

2-Methyl-2-(2-trifluoromethoxyphenoxy)propionic Acid

The title compound was prepared according to the procedure outlined in Example 44C, substituting 2-trifluoromethoxylphenol for the product of Example 44B.

EXAMPLE 66B

N-[(E)-5-(Aminosulfonyl)-2-adamantyl]-2-methyl-2-[2-(trifluoromethoxy)phenoxy]propanamide The title compound was prepared according to the procedure outlined in Example 54J substituting the product of Example 66A for 2-(4-chlorophenoxy)-2-methylpropionic acid. $^1$H NMR (400 MHz, CDCl$_3$) δ ppm 7.31 (dd, J=8 & 2 Hz, 1H), 7.22 (m, 1H), 7.18 (d, J=8 Hz, 1H), 7.08 (m, 2H), 4.39 (s, 2H), 4.05 (m, 1H), 2.30-2.05 (m, 8H), 1.75 (m, 2H), 1.59 (m, 3H), 1.55 (s, 6H). MS (ESI+) m/z 427 (M+H)$^+$.

EXAMPLE 67

N-[(E)-5-(Aminosulfonyl)-2-adamantyl]-2-(2-chloro-4-fluorophenoxy)-2-methylpropanamide The title compound was prepared according to the procedure outlined in Example 54J substituting the product of Example 49A for 2-(4-chlorophenoxy)-2-methylpropionic acid. $^1$H NMR (400 MHz, CDCl$_3$) δ ppm 7.54 (d, J=8 Hz, 1H), 7.17 (m, 1H), 7.08 (m, 1H), 6.93 (m, 1H), 4.26 (s, 2H), 4.08 (m, 1H), 2.35-2.05 (m, 8H), 1.87 (m, 2H), 1.60 (m, 3H), 1.54 (s, 6H). MS (ESI+) m/z 445 (M+H)$^+$.

Biological Data

Measurement of Inhibition Constants:

The ability of test compounds to inhibit human 11β-HSD-1 enzymatic activity in vitro was evaluated in a Scintillation Proximity Assay (SPA). Tritiated-cortisone substrate, NADPH cofactor and titrated compound were incubated with truncated human 11β-HSD-1 enzyme (24-287AA) at room temperature to allow the conversion to cortisol to occur. The reaction was stopped by adding a non-specific 11β-HSD inhibitor, 18β-glycyrrhetinic acid. The tritiated cortisol was captured by a mixture of an anti-cortisol monoclonal antibody and SPA beads coated with anti-mouse antibodies. The reaction plate was shaken at room temperature and the radioactivity bound to SPA beads was then measured on a β-scintillation counter. The 11-βHSD-1 assay was carried out in 96-well microtiter plates in a total volume of 220 µl. To start the assay, 188 µl of master mix which contained 17.5 nM $^3$H-cortisone, 157.5 nM cortisone and 181 mM NADPH was added to the wells. In order to drive the reaction in the forward direction, 1 mM G-6-P was also added. Solid compound was dissolved in DMSO to make a 10 mM stock followed by a subsequent 10-fold dilution with 3% DMSO in Tris/EDTA buffer (pH 7.4). 22 µl of titrated compounds was then added in triplicate to the substrate. Reactions were initiated by the addition of 10 µl of 0.1 mg/ml E. coli lysates overexpressing 11β-HSD-1 enzyme. After shaking and incubating plates for 30 minutes at room temperature, reactions were stopped by adding 10 µl of 1 mM glycyrrhetinic acid. The product, tritiated cortisol, was captured by adding 10 µl of 1 µM monoclonal anti-cortisol antibodies and 100 µl SPA beads coated with anti-mouse antibodies. After shaking for 30 minutes, plates were read on a liquid scintillation counter Topcount. Percent inhibition was calculated based on the background and the maximal signal. Wells that contained substrate without compound or enzyme were used as the background, while the wells that contained substrate and enzyme without any compound were considered as maximal signal. Percent of inhibition of each compound was calculated relative to the maximal signal and IC$_{50}$ curves were generated. This assay was applied to 11β-HSD-2 as well, whereby tritiated cortisol and NAD$^+$ were used as substrate and cofactor, respectively.

Compounds of the present invention are active in the 11-βHSD-1 assay described above and show selectivity for human 11-βHSD-1 over human 11-β-HSD-2, as indicated in Table 1.

TABLE 1

11-β-HSD-1 and 11-β-HSD-2 activity for representative compounds.

| Compound | 11-β-HSD-1 IC$_{50}$ (nM) | 11-β-HSD-2 IC$_{50}$ (nM) |
| --- | --- | --- |
| A | 28 | >10,000 |
| B | 35 | 10,000 |
| C | 35 | |
| D | 34 | |
| E | 72 | 29,000 |
| F | 24 | 32,000 |
| G | 44 | 11,000 |
| H | 40 | 2,600 |
| I | 38 | 15,000 |
| J | 45 | 37,000 |
| K | 18 | 35,000 |
| L | 45 | 59,000 |
| M | 43 | 21,000 |
| N | 41 | >100,000 |
| O | 96 | 100,000 |
| P | 41 | >100,000 |
| Q | 29 | 10,000 |
| R | 68 | 65,000 |
| S | 53 | 10,000 |
| T | 28 | 10,000 |
| U | 26 | 14,000 |
| V | 89 | 90,000 |
| W | 48 | 18,000 |
| X | 30 | >100,000 |
| Y | 30 | >100,000 |
| Z | 89 | >100,000 |

The data in Table 1 demonstrates that compounds A, B, C, D and E are active in the human 11β-HSD-1 enzymatic SPA assay described above and that the tested compound showed selectivity for 11β-HSD-1 over 11β-HSD-2. The 11β-HSD-1 inhibitors of this invention generally have an inhibition constant IC$_{50}$ of less than 600 nM and preferably less than 50 nM. The compounds preferably are selective, having an inhibition constant IC$_{50}$ against 11β-HSD-2 greater than 1000 nM and preferably greater than 10,000 nM. Generally, the IC$_{50}$ ratio for 11β-HSD-2 to 11β-HSD-1 of a compound is at least 10 or greater and preferably 100 or greater.

Metabolic Stability

Incubation Conditions:

Metabolic stability screen: each substrate (10 µM) was incubated with microsomal protein (0.1-0.5 mg/ml) in 50 mM potassium phosphate buffer (pH 7.4) in 48-Well plate. The enzyme reaction was initiated by the addition of 1 mM NADPH, then incubated at 37° C. in a Form a Scientific incubator (Marietta, Ohio, USA) with gentle shaking. The reactions were quenched by the addition of 800 µl of ACN/MeOH (1:1, v/v), containing 0.5 µM of internal standard (IS), after 30 min incubation. Samples were then filtered by using Captiva 96-Well Filtration (Varian, Lake Forest, Calif., USA) and analyzed by LC/MS (mass spectrometry). Liver microsomal incubations were conducted in duplicate.

LC/MS Analysis:

The parent remaining in the incubation mixture was determined by LC/MS. The LC/MS system consisted of an Agilent 1100 series (Agilent Technologies, Waldbronn, Germany) and API 2000 (MDS SCIEX, Ontario, Canada). A Luna C8(2) (50×2.0 mm, particle size 3 µm, Phenomenex, Torrance, Calif., USA) was used to quantify each compound at ambient temperature. The mobile phase consisted of (A): 10 mM NH$_4$AC (pH 3.3) and (B): 100% ACN and was delivered at a flow rate of 0.2 ml/min. Elution was achieved using a linear gradient of 0-100% B over 3 min, then held 100% B for 4 min and returned to 100% A in 1 min. The column was equilibrated for 7 min before the next injection.

The peak area ratios (each substrate over IS) at each incubation time were expressed as the percentage of the ratios (each substrate over IS) of the control samples (0 min incubation). The parent remaining in the incubation mixture was expressed as the percentage of the values at 0 min incubation. The percentage turnover is calculated using the following equation (%turnover=100%turnover−%parent remaining) and is recorded as the percentage turnover in the Table 2.

TABLE 2

Microsomal metabolic stability.

| Compound | Human Liver Microsomal Turnover (%) | Mouse Liver Microsomal Turnover (%) |
|---|---|---|
| A | 19 | 37 |
| B | 47 | 25 |
| E | 0 | 0 |
| EE | 88 | 86 |

Compounds A, B and E contain a substituted adamantane, whereas the adamantane ring of compound EE is unsubstituted. The microsomal, metabolic, stability data in Table 2 demonstrates that substituted adamantane compounds of the present invention may exhibit an increase in metabolic stability compared to unsubstituted adamantane compounds which may lead to longer in vivo half lives and pharmacokinetic advantages over unsubstituted adamantanes.

Biochemical Mechanism

Glucocorticoids are steroid hormones that play an important role in regulating multiple physiological processes in a wide range of tissues and organs. For example, glucocorticoids are potent regulators of glucose and lipid metabolism. Excess glucocorticoid action may lead to insulin resistance, type 2 diabetes, dyslipidemia, visceral obesity and hypertension. Cortisol is the major active and cortisone is the major inactive form of glucocorticoids in humans, while corticosterone and dehydrocorticosterone are the major active and inactive forms in rodents.

Previously, the main determinants of glucocorticoid action were thought to be the circulating hormone concentration and the density of glucocorticoid receptors in the target tissues. In the last decade, it was discovered that tissue glucocorticoid levels may also be controlled by 11β-hydroxysteroid dehydrogenases enzymes (11β-HSDs). There are two 11β-HSD isozymes which have different substrate affinities and cofactors. The 11β-hydroxysteroid dehydrogenases type 1 enzyme (11β-HSD-1) is a low affinity enzyme with $K_m$ for cortisone in the micromolar range that prefers NADPH/NADP$^+$ (nicotinamide adenine dinucleotide) as cofactors. 11β-HSD-1 is widely expressed and particularly high expression levels are found in liver, brain, lung, adipose tissue and vascular smooth muscle cells. In vitro studies indicate that 11β-HSD-1 is capable of acting both as a reductase and a dehydrogenase. However, many studies have shown that it is predominantly a reductase in vivo and in intact cells. It converts inactive 11-ketoglucocorticoids (i.e., cortisone or dehydrocorticosterone) to active 11-hydroxyglucocorticoids (i.e., cortisol or corticosterone) and therefore amplifies the glucocorticoid action in a tissue-specific manner.

With only 20% homology to 11β-HSD-1, the 11β-hydroxysteroid dehydrogenases type 2 enzyme (11β-HSD-2) is a NAD$^+$-dependent, high affinity dehydrogenase with a $K_m$ for cortisol in the nanomolar range. 11β-HSD-2 is found primarily in mineralocorticoid target tissues, such as kidney, colon and placenta. Glucocorticoid action is mediated by the binding of glucocorticoids to receptors, such as mineralocorticoid receptors and glucocorticoid receptors. Through binding to its receptor, the main mineralocorticoid aldosterone controls the water and salts balance in the body. However, the mineralocorticoid receptors have a high affinity for both cortisol and aldosterone. 11β-HSD-2 converts cortisol to inactive cortisone, therefore preventing the non-selective mineralocorticoid receptors from being exposed to high levels of cortisol. Mutations in the gene encoding 11β-HSD-2 cause Apparent Mineralocorticoid Excess Syndrome (AME), which is a congenital syndrome resulting in hypokaleamia and severe hypertension. AME Patients have elevated cortisol levels in mineralocorticoid target tissues due to reduced 11β-HSD-2 activity. The AME symptoms may also be induced by administration of 11β-HSD-2 inhibitor, glycyrrhetinic acid. The activity of 11β-HSD-2 in placenta is probably important for protecting the fetus from excess exposure to maternal glucocorticoids, which may result in hypertension, glucose intolerance and growth retardation. Due to the potential side effects resulting from 11β-HSD-2 inhibition, the present invention describes selective 11β-HSD-1 inhibitors.

Glucocorticoid levels and/or activity may contribute to numerous disorders, including Type II diabetes, obesity, dyslipidemia, insulin resistance and hypertension. Administration of the compounds of the present invention decreases the level of cortisol and other 11β-hydroxysteroids in target tissues, thereby reducing the effects of glucocorticoid activity in key target tissues. The present invention could be used for the treatment, control, amelioration, prevention, delaying the onset of or reducing the risk of developing the diseases and conditions that are described herein.

Since glucocorticoids are potent regulators of glucose and lipid metabolism, glucocorticoid action may contribute or lead to insulin resistance, type 2 diabetes, dyslipidemia, visceral obesity and hypertension. For example, cortisol antagonizes the insulin effect in liver resulting in reduced insulin sensitivity and increased gluconeogenesis. Therefore, patients who already have impaired glucose tolerance have a greater probability of developing type 2 diabetes in the presence of abnormally high levels of cortisol. Previous studies (B. R. Walker et al., J. of Clin. Endocrinology and Met., 80: 3155-3159, 1995) have demonstrated that administration of non-selective 11β-HSD-1 inhibitor, carbenoxolone, improves insulin sensitivity in humans. Therefore, administration of a therapeutically effective amount of an 11β-HSD-1 inhibitor may treat, control, ameliorate, delay, or prevent the onset of type 2 diabetes.

Administration of glucocorticoids in vivo has been shown to reduce insulin secretion in rats (B. Billaudel et al., Horm. Metab. Res. 11: 555-560, 1979). It has also been reported that conversion of dehydrocorticosterone to corticosterone by 11β-HSD-1 inhibits insulin secretion from isolated murine pancreatic β cells. (B. Davani et al., J. Biol. Chem., 275: 34841-34844, 2000), and that incubation of isolated islets with an 11β-HSD-1 inhibitor improves glucose-stimulated insulin secretion (H Orstater et al., Diabetes Metab. Res. Rev. 21: 359-366, 2005). Therefore, administration of a therapeutically effective amount of an 11β-HSD-1 inhibitor may treat, control, ameliorate, delay, or prevent the onset of type 2 diabetes by improving glucose-stimulated insulin secretion in the pancreas.

Abdominal obesity is closely associated with glucose intolerance (C. T. Montaque et al., Diabetes, 49: 883-888, 2000), hyperinsulinemia, hypertriglyceridemia and other factors of metabolic syndrome (also known as syndrome X), such as high blood pressure, elevated VLDL and reduced HDL. Animal data supporting the role of 11β-HSD-1 in the pathogenesis of the metabolic syndrome is extensive (Masuzaki, et al. *Science.* 294: 2166-2170, 2001; Paterson, J. M., et al.; *Proc Natl. Acad. Sci. USA.* 101: 7088-93, 2004; Montague and O'Rahilly. *Diabetes.* 49: 883-888, 2000). Therefore, administration of a therapeutically effective amount of an 11β-HSD-1 inhibitor may treat, control, ameliorate, delay, or prevent the onset of obesity. Long-term treatment with an 11β-HSD-1 inhibitor may also be useful in delaying the onset of obesity, or perhaps preventing it entirely if the patients use an 11β-HSD-1 inhibitor in combination with controlled diet, exercise, or in combination or sequence with other pharmacological approaches.

By reducing insulin resistance and/or maintaining serum glucose at normal concentrations and/or reducing obesity compounds of the present invention also have utility in the treatment and prevention of conditions that accompany Type 2 diabetes and insulin resistance, including the metabolic syndrome or syndrome X, obesity, reactive hypoglycemia, and diabetic dyslipidemia.

11β-HSD-1 is present in multiple tissues, including vascular smooth muscle, where local glucocorticoid levels that are thought to increase insulin resistance, leading to reductions in nitric oxide production, and potentiation of the vasoconstrictive effects of both catecholamines and angiotensin II (M. Pirpiris et al., Hypertension, 19:567-574, 1992, C. Kornel et al., Steroids, 58: 580-587, 1993, B. R. Walker and B. C. Williams, Clin. Sci. 82:597-605, 1992; Hodge, G. et al Exp. Physiol 87: 1-8, 2002). High levels of cortisol in tissues where the mineralocorticoid receptor is present may lead to hypertension, as observed in Cushing's patients (See, D. N. Orth, N. Engl. J. Med. 332:791-803, 1995, M. Boscaro, et al., Lancet, 357: 783-791, 2001, X. Bertagna, et al, Cushing's Disease. In: Melmed S., Ed. The Pituitary. 2$^{nd}$ ed. Malden, Mass.: Blackwell; 592-612, 2002). Transgenic mice overexpressing 11β-HSD-1 in liver and fat are also hypertensive, a phenotype believed to result from glucocorticoid activation of the renin angiotensin system (Paterson, J. M. et al, PNAS. 101: 7088-93, 2004; Masuzaki, H. et al, J. Clin. Invest. 112: 83-90, 2003). Therefore, administration of a therapeutically effective dose of an 11β-HSD-1 inhibitor may treat, control, ameliorate, delay, or prevent the onset of hypertension.

Cushing's syndrome is a life-threatening metabolic disorder characterized by sustained and elevated glucocorticoid levels caused by the endogenous and excessive production of cortisol from the adrenal glands. Typical Cushingoid characteristics include central obesity, diabetes and/or insulin resistance, moon face, buffalo hump, skin thinning, dyslipidemia, osteoporosis, reduced cognitive capacity, dementia, hypertension, sleep deprivation, and atherosclerosis among others (Principles and Practice of Endocrinology and Metabolism. Edited by Kenneth Becker, Lippincott Williams and Wilkins Publishers, Philadelphia, 2001; pg. 723-8). The same characteristics can also arise from the exogenous administration of high doses of exogenous glucocorticoids, such as prednisone or dexamethasone, as part of an anti-inflammatory treatment regimen. Endogenous Cushings typically evolves from pituitary hyperplasia, some other ectopic source of ACTH, or from an adrenal carcinoma or nodular hyperplasia. Administration of a therapeutically effective dose of an 11β-HSD-1 inhibitor may reduce local glucocorticoid concentrations and therefore treat, control, ameliorate, delay, or prevent the onset of Cushing's disease and/or similar symptoms arising from glucocorticoid treatment.

11β-HSD-1 is expressed in mammalian brain, and published data indicates that glucocorticoids may cause neuronal degeneration and dysfunction, particularly in the aged (de Quervain et al.; *Hum Mol Genet.* 13: 47-52, 2004; Belanoff et al. *J. Psychiatr Res.* 35: 127-35, 2001). Evidence in rodents and humans suggests that prolonged elevation of plasma glucocorticoid levels impairs cognitive function that becomes more profound with aging. (Issa, A. M. et al. J. Neurosci. 10: 3247-54, 1990; Lupien, S. J et al. Nat. Neurosci. 1: 69-73, 1998; Yau, J. L. W. et al *Proc Natl Acad Sci USA.* 98: 4716-4712, 2001). Thekkapat et al has recently shown that 11β-HSD-1 mRNA is expressed in human hippocampus, frontal cortex and cerebellum, and that treatment of elderly diabetic individuals with the non-selective HSD1/2 inhibitor carbenoxolone improved verbal fluency and memory (*Proc Natl Acad Sci USA.* 101: 6743-9, 2004). Additional CNS effects of glucocorticoids include glucocorticoid-induced acute psychosis which is of major concern to physicians when treating patients with these steroidal agents (Wolkowitz et al.; *Ann NY Acad Sci.* 1032: 191-4, 2004). Conditional mutagenesis studies of the glucocorticoid receptor in mice have also provided genetic evidence that reduced glucocorticoid signaling in the brain results in decreased anxiety (Tronche, F. et al. (1999) Nature Genetics 23: 99-103). Therefore, it is expected that potent, selective 11β-HSD-1 inhibitors would treat, control, ameliorate, delay, or prevent the onset of cognitive decline, dementia, steroid-induced acute psychosis, depression, and/or anxiety.

In Cushing's patients, excess cortisol levels contributes to the development of hypertension, dyslipidemia, insulin resistance, and obesity, conditions characteristic of metabolic syndrome (Orth, D. N. et al N. Engl. J. Med. 332:791-803, 1995; Boscaro, M. et al., Lancet, 357: 783-791, 2001, Bertagna, X. et al, Cushing's Disease. In: Melmed S., Ed. The Pituitary. 2$^{nd}$ ed. Malden, Mass.: Blackwell; 592-612, 2002). Hypertension and dyslipidemia are also associated with development of atherosclerosis. 11β-HSD-1 knockout mice are resistant to the dyslipidemic effects of a high fat diet and have an improved lipid profile vs wild type controls (Morton N. M. et al, JBC, 276: 41293-41300, 2001), and mice which overexpress 111-HSD-1 in fat exhibit the dyslipidemic phenotype characteristic of metabolic syndrome, including elevated circulating free fatty acids, and triclylgerides (Masuzaki, H., et al Science. 294: 2166-2170, 2001). Administration of a selective 11β-HSD-1 inhibitor has also been shown to reduce elevated plasma triglycerides and free fatty acids in mice on a high fat diet, and significantly reduce aortic content of cholesterol esters, and reduce progression of atherosclerotic plaques in mice (Hermanowski-Vosatka, A. et al. J. Exp. Med. 202: 517-27, 2005). The administration of a therapeutically effective amount of an 11β-HSD-1 inhibitor would therefore be expected to treat, control, ameliorate, delay, or prevent the onset of dyslipidemia and/or atherosclerosis.

Glucocorticoids are known to cause a variety of skin related side effects including skin thinning, and impairment of wound healing (Anstead, G. *Adv Wound Care.* 11: 277-85, 1998; Beer, et al.; *Vitam Horm.* 59: 217-39, 2000). 11β-HSD-1 is expressed in human skin fibroblasts, and it has been shown that the topical treatment with the non-selective HSD1/2 inhibitor glycerrhetinic acid increases the potency of topically applied hydrocortisone in a skin vasoconstrictor assay (Hammami, M M, and Siiteri, P K. *J. Clin. Endocrinol. Metab.* 73: 326-34, 1991). Advantageous effects of selective 11β-HSD-1 inhibitors such as BVT.2733 on wound healing have also been reported (WO 2004/11310). High levels of glucocorticoids inhibit blood flow and formation of new blood vessels to healing tissues. In vitro and in vivo models of angiogenesis have shown that systemic antagonism with the glucocorticoid receptor RU-486 enchances angiogenesis in subcutaneous sponges as well as in mouse myocardium following coronary artery ligation (Walker, et al, PNAS, 102: 12165-70, 2005). 11β-HSD-1 knockout mice also showed enhanced angiogenesis in vitro and in vivo within sponges, wounds, and infarcted myocardium. It is therefore expected that potent, selective 11β-HSD-1 inhibitors would treat, control, ameliorate, delay, or prevent the onset of skin thinning and/or promote wound healing and/or angiogenesis.

Although cortisol is an important and well-recognized anti-inflammatory agent (J. Baxer, Pharmac. Ther., 2:605-659, 1976), if present in large amount it also has detrimental effects. In certain disease states, such as tuberculosis, psoriasis and stress in general, high glucocorticoid activity shifts the immune response to a humoral response, when in fact a cell based response may be more beneficial to patients. Inhibition of 11β-HSD-1 activity may reduce glucocorticoid levels, thereby shifting the immuno response to a cell based response. (D. Mason, Immunology Today, 12: 57-60, 1991, G. A. W. Rook, Baillier's Clin. Endocrinol. Metab. 13: 576-581, 1999). Therefore, administration of 11β-HSD-1 specific inhibitors could treat, control, ameliorate, delay, or prevent the onset of tuberculosis, psoriasis, stress, and diseases or conditions where high glucocorticoid activity shifts the immune response to a humoral response.

One of the more significant side effects associated with topical and systemic glucocorticoid therapy is glaucoma, resulting in serious increases in intraocular pressure, with the potential to result in blindness (Armaly et al.; *Arch Opthalmol.* 78: 193-7, 1967; Stokes et al.; *Invest Opthalmol Vis Sci.* 44: 5163-7, 2003;). The cells that produce the majority of aqueous humor in the eye are the nonpigmented epithelial cells (NPE). These cells have been demonstrated to express 11β-HSD-1, and consistent with the expression of 11β-HSD-1, is the finding of elevated ratios of cortisol:cortisone in the aqueous humor (Rauz et al. *Invest Opthalmol Vis Sci.* 42: 2037-2042, 2001). Furthermore, it has been shown that patients who have glaucoma, but who are not taking exogenous steroids, have elevated levels of cortisol vs. cortisone in their aqueous humor (Rauz et al. *QJM.* 96: 481-490, 2003.) Treatment of patients with the nonselective HSD1/2 inhibitor carbenoxolone for 4 or 7 days significantly lowered intraocular pressure and local cortisol generation within the eye (Rauz et al.; *QJM.* 96: 481-490, 2003.). It is therefore expected that potent, selective 11β-HSD-1 inhibitors would treat, control, ameliorate, delay, or prevent the onset of glaucoma.

Glucocorticoids (GCs) are known to increase bone resorption and reduce bone formation in mammals (Turner et al. *Calcif Tissue Int.* 54: 311-5, 1995; Lane, N E et al. *Med Pediatr Oncol.* 41: 212-6, 2003). 11β-HSD-1 mRNA expression and reductase activity have been demonstrated in primary cultures of human osteoblasts in homogenates of human bone (Bland et al.; *J. Endocrinol.* 161: 455-464, 1999; Cooper et al.; *Bone,* 23: 119-125, 2000). In surgical explants obtained from orthopedic operations, 11β-HSD-1 expression in primary cultures of osteoblasts was found to be increased approximately 3-fold between young and old donors (Cooper et al.; *J. Bone Miner Res.* 17: 979-986, 2002). Glucocorticoids, such as prednisone and dexamethasone, are also commonly used to treat a variety of inflammatory conditions including arthritis, inflammatory bowl disease, and asthma. These steroidal agents have been shown to increase expression of 11β-HSD-1 mRNA and activity in human osteoblasts (Cooper et al.; *J. Bone Miner Res.* 17: 979-986, 2002). These studies suggest that 11β-HSD-1 plays a potentially important role in the development of bone-related adverse events as a result of excessive glucocorticoid levels or activity. Bone samples taken from healthy human volunteers orally dosed with the non-selective HSD1/2 inhibitor carbenoxolone showed a significant decrease in markers of bone resorption (Cooper et al.; *Bone.* 27: 375-81, 2000). It is therefore expected that potent, selective 11β-HSD-1 inhibitors would treat, control, ameliorate, delay, or prevent the onset of conditions of glucocorticoid-induced or age-dependent osteoporosis The following diseases, disorders and conditions can be treated, controlled, prevented or delayed, by treatment with the compounds of this invention: (1) hyperglycemia, (2) low glucose tolerance, (3) insulin resistance, (4) lipid disorders, (5) hyperlipidemia, (6) hypertriglyceridemia, (9) hypercholesterolemia, (10) low HDL levels, (11) high LDL levels, (12), atherosclerosis and its sequelae, (13) vascular restensosis, (14) pancreatitis, (15) abdominal obesity, (16) neurodegenerative disease, (17) retinopathy, (18) nephropather, (19), neuropathy, (20) hypertension and other disorders where insulin resistance is a component, and (21) other diseases, disorders, and conditions that can benefit from reduced local glucocorticoid levels.

Therapeutic compositions of the present compounds comprise an effective amount of the same formulated with one or more therapeutically suitable excipients. The term "therapeutically suitable excipient," as used herein, generally refers to pharmaceutically suitable, solid, semi-solid or liquid fillers, diluents, encapsulating material, formulation auxiliary and the like. Examples of therapeutically suitable excipients include, but are not limited to, sugars, cellulose and derivatives thereof, oils, glycols, solutions, buffers, colorants, releasing agents, coating agents, sweetening agents, flavoring agents, perfuming agents and the like. Such therapeutic compositions may be administered parenterally, intracistemally, orally, rectally, intraperitoneally or by other dosage forms known in the art.

Liquid dosage forms for oral administration include, but are not limited to, emulsions, microemulsions, solutions, suspensions, syrups and elixirs. Liquid dosage forms may also contain diluents, solubilizing agents, emulsifying agents, inert diluents, wetting agents, emulsifiers, sweeteners, flavorants, perfuming agents and the like.

Injectable preparations include, but are not limited to, sterile, injectable, aqueous, oleaginous solutions, suspensions, emulsions and the like. Such preparations may also be formulated to include, but are not limited to, parenterally suitable diluents, dispersing agents, wetting agents, suspending agents and the like. Such injectable preparations may be sterilized by filtration through a bacterial-retaining filter. Such preparations may also be formulated with sterilizing agents that dissolve or disperse in the injectable media or other methods known in the art.

The absorption of the compounds of the present invention may be delayed using a liquid suspension of crystalline or amorphous material having poor water solubility. The rate of absorption of the compounds generally depends upon the rate of dissolution and crystallinity. Delayed absorption of a parenterally administered compound may also be accomplished by dissolving or suspending the compound in oil. Injectable depot dosage forms may also be prepared by microencapsulating the same in biodegradable polymers. The rate of drug release may also be controlled by adjusting the ratio of compound to polymer and the nature of the polymer employed. Depot injectable formulations may also prepared by encapsulating the compounds in liposomes or microemulsions compatible with body tissues.

Solid dosage forms for oral administration include, but are not limited to, capsules, tablets, gels, pills, powders, granules and the like. The drug compound is generally combined with at least one therapeutically suitable excipient, such as carriers, fillers, extenders, disintegrating agents, solution retarding agents, wetting agents, absorbents, lubricants and the like. Capsules, tablets and pills may also contain buffering agents. Suppositories for rectal administration may be prepared by mixing the compounds with a suitable non-irritating excipient that is solid at ordinary temperature but fluid in the rectum.

The present drug compounds may also be microencapsulated with one or more excipients. Tablets, dragees, capsules, pills and granules may also be prepared using coatings and shells, such as enteric and release or rate controlling polymeric and nonpolymeric materials. For example, the compounds may be mixed with one or more inert diluents. Tableting may further include lubricants and other processing aids. Similarly, capsules may contain opacifying agents that delay release of the compounds in the intestinal tract.

Transdermal patches have the added advantage of providing controlled delivery of the present compounds to the body. Such dosage forms are prepared by dissolving or dispensing the compounds in suitable medium. Absorption enhancers may also be used to increase the flux of the compounds across the skin. The rate of absorption may be controlled by employing a rate controlling membrane. The compounds may also be incorporated into a polymer matrix or gel.

For a given dosage form, disorders of the present invention may be treated, prophylatically treated, or have their onset delayed in a patient by administering to the patient a therapeutically effective amount of compound of the present invention in accordance with a suitable dosing regimen. In other words, a therapeutically effective amount of any one of compounds of formulas I thru IX is administered to a patient to treat and/or prophylatically treat disorders modulated by the 11-beta-hydroxysteroid dehydrogenase type 1 enzyme. The specific therapeutically effective dose level for a given patient population may depend upon a variety of factors including, but not limited to, the specific disorder being treated, the severity of the disorder; the activity of the compound, the specific composition or dosage form, age, body weight, general health, sex, diet of the patient, the time of administration, route of administration, rate of excretion, duration of the treatment, drugs used in combination, coincidental therapy and other factors known in the art.

The present invention also includes therapeutically suitable metabolites formed by in vivo biotransformation of any of the compounds of formula I thru IX. The term "therapeutically suitable metabolite", as used herein, generally refers to a pharmaceutically active compound formed by the in vivo biotransformation of compounds of formula I thru IX. For example, pharmaceutically active metabolites include, but are not limited to, compounds made by adamantane hydroxylation or polyhydroxylation of any of the compounds of formulas I thru IX. A discussion of biotransformation is found in Goodman and Gilman's, The Pharmacological Basis of Therapeutics, seventh edition, MacMillan Publishing Company, New York, N.Y., (1985).

The total daily dose (single or multiple) of the drug compounds of the present invention necessary to effectively inhibit the action of 11-beta-hydroxysteroid dehydrogenase type 1 enzyme may range from about 0.01 mg/kg/day to about 50 mg/kg/day of body weight and more preferably about 0.1 mg/kg/day to about 25 mg/kg/day of body weight. Treatment regimens generally include administering from about 10 mg to about 1000 mg of the compounds per day in single or multiple doses.

It is understood that the foregoing detailed description and accompanying examples are merely illustrative and are not to be taken as limitations upon the scope of the invention, which is defined solely by the appended claims and their equivalents. Various changes and modifications to the disclosed aspects will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed:
1. A compound of formula (I)

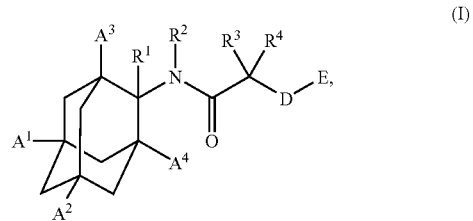

wherein $A^1$ is alkenyl, alkyl-NH-alkyl, alkyl-NH-heteroaryl, alkylcarbonyl, carboxyalkyl, carboxycycloalkyl, cyano, cycloalkyl, cycloalkylalkyl, cycloalkylcarbonyl, aryl, arylalkyl, aryloxyalkyl, arylcarbonyl, heteroaryl, heteroarylalkyl, heteroaryloxyalkyl, heterocycle, heterocyclealkyl, heterocycleoxyalkyl, halogen, haloalkyl, $-NR^5-[C(R^6R^7)]$, $-C(O)-R^8$, $-O-[C(R^9R^{10})]_p$$-C(O)-R^{11}$, $-OR^{12}$, $-N(R^{13}R^{14})$, $-CO_2R^{15}$, $-C(O)-N(R^{16}R^{17})$, $-C(R^{18}R^{19})-OR^{20}$, $-C(R^{21}R^{22})-N(R^{23}R^{24})$, $-C(=NOH)-N(H)_2$, $-C(R^{18a}R^{19a})-C(O)N(R^{23}R^{24})$, or $-C(R^{18a}R^{19a})-S(O)_2-N(R^{25}R^{26})$;

$A^2$, $A^3$ and $A^4$ are each individually hydrogen, alkenyl, alkyl, alkyl-NH-alkyl, alkylcarbonyl, alkylsulfonyl, carboxyalkyl, carboxycycloalkyl, cyano, cycloalkyl, cycloalkylcarbonyl, cycloalkylsulfonyl, aryl, arylalkyl, aryloxyalkyl, arylcarbonyl, arylsulfonyl, heteroaryl, heteroarylalkyl, heteroaryloxyalkyl, heteroarylsulfonyl, heterocycle, heterocyclealkyl, heterocycleoxyalkyl, heterocyclesulfonyl, halogen, haloalkyl, $-NR^5-[C(R^6R^7)]_n-C(O)-R^8$, $-O-[C(R^9R^{10})]_p-C(O)-R^{11}$, $-OR^{12}$, $-S$-alkyl, $-S(O)$-alkyl, $-N(R^{13}R^{14})$, $-CO_2R^{15}$, $-C(O)-N(R^{16}R^{17})$, $-C(R^{18}R^{19})-OR^{20}$, $-C(R^{21}R^{22})-N(R^{23}R^{24})$, $-C(=NOH)-N(H)_2$, $-C(R^{18a}R^{19a})-C(O)N(R^{23}R^{24})$, $-S(O)_2-N(R^{25}R^{26})$, or $-C(R^{18a}R^{19a})-S(O)_2-N(R^{25}R^{26})$;

n is 0 or 1;
p is 0 or 1;
D is $-O-$, $-S-$, $-S(O)-$ or $-S(O)_2-$;
E is arylalkyl or cycloalkylalkyl;
$R^1$ is hydrogen or alkyl;
$R^2$ is hydrogen, alkyl or cycloalkyl;
$R^3$ and $R^4$ are each independently hydrogen, alkyl, carboxyalkyl, carboxycycloalkyl, cycloalkyl, haloalkyl, aryl, arylalkyl, heteroaryl, heteroarylalkyl, heterocycle or heterocyclealkyl, or $R^3$ and $R^4$ taken together with the atoms to which they are attached form a ring selected from the group consisting of cycloalkyl and heterocycle;
$R^5$ is hydrogen, alkyl, carboxyalkyl, cycloalkyl, carboxycycloalkyl, aryl, arylalkyl, aryloxyalkyl, hydroxy, alkoxy, heteroaryl, heteroarylalkyl, heteroaryloxyalkyl, heterocycle, heterocyclealkyl or heterocycleoxyalkyl;

$R^6$ and $R^7$ are each independently hydrogen or alkyl, or $R^6$ and $R^7$ taken together with the atom to which they are attached form a ring of cycloalkyl or heterocycle;

$R^8$ is hydrogen, alkyl, carboxy, carboxyalkyl, cycloalkyl, carboxycycloalkyl, aryl, arylalkyl, aryloxy, aryloxyalkyl, hydroxy, alkoxy, cycloalkyloxy, heteroaryl, heteroarylalkyl, heteroaryloxy, heteroaryloxyalkyl, heterocycle, heterocyclealkyl, heterocycleoxy, heterocycleoxyalkyl or —N($R^{27}R^{28}$);

$R^9$ and $R^{10}$ are each independently hydrogen or alkyl, or $R^9$ and $R^{10}$ taken together with the atom to which they are attached form a ring of cycloalkyl or heterocycle;

$R^{11}$ is hydroxy or —N($R^{29}R^{30}$);

$R^{12}$ is hydrogen, alkyl, carboxyalkyl, cycloalkyl, carboxycycloalkyl, aryl, arylalkyl, aryloxyalkyl, haloalkyl, heteroaryl, heteroarylalkyl, heteroaryloxyalkyl, heterocycle, heterocyclealkyl or heterocycleoxyalkyl;

$R^{13}$ and $R^{14}$ are each independently hydrogen, alkyl, alkylsufonyl, aryl, arylalkyl, aryloxyalkyl, arylsulfonyl, carboxyalkyl, cycloalkyl, carboxycycloalkyl, cycloalkylsulfonyl, heteroaryl, heteroarylalkyl, heteroaryloxyalkyl, heteroarylsulfonyl, heterocycle, heterocyclealkyl, heterocycleoxyalkyl or heterocyclesulfonyl;

$R^{15}$ is hydrogen, alkyl, carboxyalkyl, cycloalkyl, carboxycycloalkyl, aryl, arylalkyl, aryloxyalkyl, heteroaryl, heteroarylalkyl, heteroaryloxyalkyl, heterocycle, heterocyclealkyl or heterocycleoxyalkyl;

$R^{16}$ and $R^{17}$ are each independently hydrogen, alkyl, alkoxy, alkylsufonyl, aryl, arylalkyl, aryloxy, aryloxyalkyl, arylsulfonyl, carboxy, carboxyalkyl, carboxycycloalkyl, cycloalkyl, cycloalkyloxy, cycloalkylsulfonyl, heteroaryl, heteroarylalkyl, heteroaryloxyalkyl, heteroaryloxy, heteroarylsulfonyl, heterocycle, heterocyclealkyl, heterocycleoxyalkyl, heterocycleoxy, heterocyclesulfonyl, hydroxy, or -alkyl-C(O)N($R^{201}R^{202}$), or $R^{16}$ and $R^{17}$ taken together with the atom to which they are attached form a heterocycle;

$R^{201}$ and $R^{202}$ are independently hydrogen or alkyl;

$R^{18}$, $R^{19}$ and $R^{20}$ are each independently hydrogen, alkyl, aryl, arylalkyl, carboxyalkyl, carboxycycloalkyl, cycloalkyl, haloalkyl, heteroaryl, heteroarylalkyl, heterocycle or heterocyclealkyl;

$R^{18a}$ and $R^{19a}$ are each independently hydrogen or alkyl;

$R^{21}$ and $R^{22}$ are each independently hydrogen, alkyl, alkylcarbonyl, alkylsulfonyl, aryl, arylcarbonyl, arylsulfonyl, cycloalkyl, carboxyalkyl, carboxycycloalkyl, cycloalkylcarbonyl, cycloalkylsulfonyl, heteroaryl, heteroarylcarbonyl, heteroarylsulfonyl, heterocycle, heterocyclecarbonyl or heterocyclesulfonyl;

$R^{23}$ and $R^{24}$ are each independently hydrogen, alkyl, alkylcarbonyl, alkoxy, alkylsulfonyl, aryl, arylcarbonyl, aryloxy, arylsulfonyl, carboxyalkyl, carboxycycloalkyl, cycloalkyl, cycloalkylcarbonyl, cycloalkyloxy, cycloalkylsulfonyl, heteroaryl, heteroarylcarbonyl, heteroaryloxy, heteroarylsulfonyl, heterocycle, heterocyclecarbonyl, heterocycleoxy, heterocyclesulfonyl or hydroxy, or $R^{23}$ and $R^{24}$ taken together with the atom to which they are attached form a ring of heteroaryl or heterocycle;

$R^{25}$ and $R^{26}$ are each independently hydrogen, alkyl, alkoxy, alkylsufonyl, aryl, arylalkyl, aryloxy, aryloxyalkyl, arylsulfonyl, carboxy, carboxyalkyl, carboxycloalkyl, cycloalkyl, cycloalkyloxy, cycloalkylsulfonyl, heteroaryl, heteroarylalkyl, heteroaryloxy, heteroaryloxyalkyl, heterocycle, heterocyclealkyl, heterocycleoxyalkyl, heterocycleoxy, heterocyclesulfonyl or hydroxy, or $R^{25}$ and $R^{26}$ taken together with the atom to which they are attached form a heterocycle;

$R^{27}$ and $R^{28}$ are each independently hydrogen, alkyl, alkoxy, alkylsufonyl, aryl, arylalkyl, aryloxy, aryloxyalkyl, arylsulfonyl, carboxy, carboxyalkyl, cycloalkyl, cycloalkyloxy, carboxycycloalkyl, cycloalkylsulfonyl, heteroaryl, heteroarylalkyl, heteroaryloxy, heteroaryloxyalkyl, heteroarylsulfonyl, heterocycle, heterocyclealkyl, heterocycleoxy, heterocycleoxyalkyl, heterocyclesulfonyl or hydroxy, or $R^{27}$ and $R^{28}$ taken together with the atom to which they are attached form a heterocycle; and $R^{29}$ and $R^{30}$ are each independently hydrogen, alkyl, alkoxy, alkylsufonyl, aryl, arylalkyl, aryloxy, aryloxyalkyl, arylsulfonyl, carboxy, carboxyalkyl, cycloalkyl, cycloalkyloxy, carboxycycloalkyl, cycloalkylsulfonyl, heteroaryl, heteroarylalkyl, heteroaryloxy, heteroaryloxyalkyl, heteroarylsulfonyl, heterocycle, heterocyclealkyl, heterocycleoxy, heterocycleoxyalkyl, heterocyclesulfonyl or hydroxyl, or $R^{29}$ and $R^{30}$ taken together with the atom to which they are attached form a heterocycle; or a salt thereof.

2. The compound according to claim 1, wherein $A^2$, $A^3$, $A^4$, $R^1$ and $R^2$ are hydrogen; D is —O—; and E is arylalkyl.

3. The compound according to claim 1, wherein $A^2$, $A^3$, $A^4$, $R^1$ and $R^2$ are hydrogen; D is —O—; and E is cycloalkylalkyl.

4. The compound as in claim 1, wherein $A^1$ is —$CO_2R^{15}$ or —C(O)—N($R^{16}R^{17}$); $A^2$, $A^3$ and $A^4$ are each hydrogen; and E is arylalkyl or cycloalkylalkyl.

5. The compound as in claim 1, selected from the group consisting of

E-4-[(2-methyl-2-{[4-(trifluoromethyl)benzyl]oxy}propanoyl)amino]adamantane-1-carboxamide;

E-4-{[2-(cyclohexylmethoxy)-2-methylpropanoyl]amino}adamantane-1-carboxylic acid; and E-4-{[2-(cyclohexylmethoxy)-2-methylpropanoyl]amino}adamantane-1-carboxamide; or a salt thereof.

6. The compound as in claim 1, that is E-4-[(2-methyl-2-{[4-(trifluoromethyl)benzyl]oxy}propanoyl)amino]adamantane-1-carboxamide; or a salt thereof.

7. The compound as in claim 1, that is E-4-{[2-(cyclohexylmethoxy)-2-methylpropanoyl]amino adamantane-1-carboxylic acid; or a salt thereof.

8. The compound as in claim 1, that is E-4-{[2-(cyclohexylmethoxy)-2-methylpropanoyl]amino adamantane-1-carboxamide; or a salt thereof.

9. A pharmaceutical composition comprising a therapeutically effective amount of the compound of formula (I) of claim 1, in combination with a pharmaceutically suitable carrier.

10. A method of inhibiting 11-beta-hydroxysteroid dehydrogenase Type I enzyme, comprising administering to a mammal, a therapeutically effective amount of the compound of formula (I) of claim 1.

11. A method of treating disorders in a mammal by inhibiting 11-beta-hydroxysteroid dehydrogenase Type I enzyme, comprising administering to a mammal, a therapeutically effective amount of the compound of formula (I) of claim 1.

12. A method of treating a disorder in a mammal in need thereof by inhibiting 11-beta-hydroxysteroid dehydrogenase Type I enzyme, comprising administering to the mammal, a therapeutically effective amount of the compound of formula (I) of claim 1, wherein the disorder is non-insulin dependent type 2 diabetes, insulin resistance, obesity, lipid disorders, metabolic syndrome, onset of cognitive decline, dementia, steroid-induced acute psychosis, depression, anxiety or a condition that involves excessive glucocorticoid action.

13. A compound of formula (I)

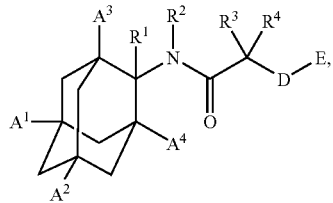

wherein $A^1$ is alkenyl, alkyl-NH-alkyl, alkyl-NH-heteroaryl, alkylcarbonyl, carboxyalkyl, carboxycycloalkyl, cyano, cycloalkyl, cycloalkylalkyl, cycloalkylcarbonyl, aryl, arylalkyl, aryloxyalkyl, arylcarbonyl, heteroaryl, heteroarylalkyl, heteroaryloxyalkyl, heterocycle, heterocyclealkyl, heterocycleoxyalkyl, halogen, haloalkyl, —NR$^5$—[C(R$^6$ R$^7$)]$_n$—C(O)—R$^8$, —O—[C(R$^9$R$^{10}$)]$_p$—C(O)—R$^{11}$, —OR$^{12}$, —N(R$^{13}$R$^{14}$), —CO$_2$R$^{15}$, —C(O)—N(R$^{16}$R$^{17}$), —C(R$^{18}$R$^{19}$)—OR$^{20}$, —C(R$^{21}$R$^{22}$)—N(R$^{23}$R$^{24}$), —C(=NOH)—N(H)$_2$, —C(R$^{18a}$R$^{19a}$)—C(O)N(R$^{23}$R$^{24}$), or —C(R$^{18a}$R$^{19a}$)—S(O)$_2$—N(R$^{25}$R$^{26}$);

$A^2$, $A^3$ and $A^4$ are each individually hydrogen, alkenyl, alkyl, alkyl-NH-alkyl, alkylcarbonyl, alkylsulfonyl, carboxyalkyl, carboxycycloalkyl, cyano, cycloalkyl, cycloalkylcarbonyl, cycloalkylsulfonyl, aryl, arylalkyl, aryloxyalkyl, arylcarbonyl, arylsulfonyl, heteroaryl, heteroarylalkyl, heteroaryloxyalkyl, heteroarylsulfonyl, heterocycle, heterocyclealkyl, heterocycleoxyalkyl, heterocyclesulfonyl, halogen, haloalkyl, —NR$^5$—[C(R$^6$R$^7$)]$_n$—C(O)—R$^8$, —O—[C(R$^9$R$^{10}$)]$_p$—C(O)—R$^{11}$, —OR$^{12}$, —S-alkyl, —S(O)-alkyl, —N(R$^{13}$R$^{14}$), —CO$_2$R$^{15}$, —C(O)—N(R$^{16}$R$^{17}$), —C(R$^{18}$R$^{19}$)—OR$^{20}$, —C(R$^{21}$R$^{22}$)—N(R$^{23}$R$^{24}$), —C(=NOH)—N(H)$_2$, —C(R$^{18a}$R$^{19a}$)—C(O)N(R$^{23}$R$^{24}$), —S(O)$_2$—N(R$^{25}$R$^{26}$), or —C(R$^{18a}$R$^{19a}$)—S(O)$_2$—N(R$^{25}$R$^{26}$);

n is 0 or 1;

p is 0 or 1;

D is —O—, —S—, —S(O)— or —S(O)$_2$—;

E is carboxyalkyl, carboxycycloalkyl, cycloalkyl, haloalkyl, heteroaryl, heterocycle, heterocyclealkyl, naphthyl or biphenyl, or R$^4$ and E taken together with the atoms to which they are attached form a heterocycle;

R$^1$ is hydrogen or alkyl;

R$^2$ is hydrogen, alkyl or cycloalkyl;

R$^3$ and R$^4$ are each independently hydrogen, alkyl, carboxyalkyl, carboxycycloalkyl, cycloalkyl, haloalkyl, aryl, arylalkyl, heteroaryl, heteroarylalkyl, heterocycle or heterocyclealkyl, or R$^3$ and R$^4$ taken together with the atoms to which they are attached form a ring selected from the group consisting of cycloalkyl and heterocycle;

R$^5$ is hydrogen, alkyl, carboxyalkyl, cycloalkyl, carboxycycloalkyl, aryl, arylalkyl, aryloxyalkyl, hydroxy, alkoxy, heteroaryl, heteroarylalkyl, heteroaryloxyalkyl, heterocycle, heterocyclealkyl or heterocycleoxyalkyl;

R$^6$ and R$^7$ are each independently hydrogen or alkyl, or R$^6$ and R$^7$ taken together with the atom to which they are attached form a ring of cycloalkyl or heterocycle;

R$^8$ is hydrogen, alkyl, carboxy, carboxyalkyl, cycloalkyl, carboxycycloalkyl, aryl, arylalkyl, aryloxy, aryloxyalkyl, hydroxy, alkoxy, cycloalkyloxy, heteroaryl, heteroarylalkyl, heteroaryloxy, heteroaryloxyalkyl, heterocycle, heterocyclealkyl, heterocycleoxy, heterocycleoxyalkyl or —N(R$^{27}$R$^{28}$);

R$^9$ and R$^{10}$ are each independently hydrogen or alkyl, or R$^9$ and R$^{10}$ taken together with the atom to which they are attached form a ring of cycloalkyl or heterocycle;

R$^{11}$ is hydroxy or —N(R$^{29}$R$^{30}$);

R$^{12}$ is hydrogen, alkyl, carboxyalkyl, cycloalkyl, carboxycycloalkyl, aryl, arylalkyl, aryloxyalkyl, haloalkyl, heteroaryl, heteroarylalkyl, heteroaryloxyalkyl, heterocycle, heterocyclealkyl or heterocycleoxyalkyl;

R$^{13}$ and R$^{14}$ are each independently hydrogen, alkyl, alkylsufonyl, aryl, arylalkyl, aryloxyalkyl, arylsulfonyl, carboxyalkyl, cycloalkyl, carboxycycloalkyl, cycloalkylsulfonyl, heteroaryl, heteroarylalkyl, heteroaryloxyalkyl, heteroarylsulfonyl, heterocycle, heterocyclealkyl, heterocycleoxyalkyl or heterocyclesulfonyl;

R$^{15}$ is hydrogen, alkyl, carboxyalkyl, cycloalkyl, carboxycycloalkyl, aryl, arylalkyl, aryloxyalkyl, heteroaryl, heteroarylalkyl, heteroaryloxyalkyl, heterocycle, heterocyclealkyl or heterocycleoxyalkyl;

R$^{16}$ and R$^{17}$ are each independently hydrogen, alkyl, alkoxy, alkylsufonyl, aryl, arylalkyl, aryloxy, aryloxyalkyl, arylsulfonyl, carboxy, carboxyalkyl, carboxycycloalkyl, cycloalkyl, cycloalkyloxy, cycloalkylsulfonyl, heteroaryl, heteroarylalkyl, heteroaryloxyalkyl, heteroaryloxy, heteroarylsulfonyl, heterocycle, heterocyclealkyl, heterocycleoxyalkyl, heterocycleoxy, heterocyclesulfonyl, hydroxy, or -alkyl-C(O)N(R$^{201}$R$^{202}$), or R$^{16}$ and R$^{17}$ taken together with the atom to which they are attached form a heterocycle;

R$^{201}$ and R$^{202}$ are independently hydrogen or alkyl;

R$^{18}$, R$^{19}$ and R$^{20}$ are each independently hydrogen, alkyl, aryl, arylalkyl, carboxyalkyl, carboxycycloalkyl, cycloalkyl, haloalkyl, heteroaryl, heteroarylalkyl, heterocycle or heterocyclealkyl;

R$^{18a}$ and R$^{19a}$ are each independently hydrogen or alkyl;

R$^{21}$ and R$^{22}$ are each independently hydrogen, alkyl, alkylcarbonyl, alkylsulfonyl, aryl, arylcarbonyl, arylsulfonyl, cycloalkyl, carboxyalkyl, carboxycycloalkyl, cycloalkylcarbonyl, cycloalkylsulfonyl, heteroaryl, heteroarylcarbonyl, heteroarylsulfonyl, heterocycle, heterocyclecarbonyl or heterocyclesulfonyl;

R$^{23}$ and R$^{24}$ are each independently hydrogen, alkyl, alkylcarbonyl, alkoxy, alkylsulfonyl, aryl, arylcarbonyl, aryloxy, arylsulfonyl, carboxyalkyl, carboxycycloalkyl, cycloalkyl, cycloalkylcarbonyl, cycloalkyloxy, cycloalkylsulfonyl, heteroaryl, heteroarylcarbonyl, heteroaryloxy, heteroarylsulfonyl, heterocycle, heterocyclecarbonyl, heterocycleoxy, heterocyclesulfonyl or hydroxy, or R$^{23}$ and R$^{24}$ taken together with the atom to which they are attached form a ring of heteroaryl or heterocycle;

R$^{25}$ and R$^{26}$ are each independently hydrogen, alkyl, alkoxy, alkylsufonyl, aryl, arylalkyl, aryloxy, aryloxyalkyl, arylsulfonyl, carboxy, carboxyalkyl, carboxycycloalkyl, cycloalkyl, cycloalkyloxy, cycloalkylsulfonyl, heteroaryl, heteroarylalkyl, heteroaryloxyalkyl, heteroaryloxy, heteroarylsulfonyl, heterocycle, heterocyclealkyl, heterocycleoxyalkyl, heterocycleoxy, heterocyclesulfonyl or hydroxy, or R$^{25}$ and R$^{26}$ taken together with the atom to which they are attached form a heterocycle;

R$^{27}$ and R$^{28}$ are each independently hydrogen, alkyl, alkoxy, alkylsufonyl, aryl, arylalkyl, aryloxy, aryloxyalkyl, arylsulfonyl, carboxy, carboxyalkyl, cycloalkyl, cycloalkyloxy, carboxycycloalkyl, cycloalkylsulfonyl, heteroaryl, heteroarylalkyl, heteroaryloxy, heteroaryloxyalkyl, heteroarylsulfonyl, heterocycle, heterocyclealkyl, heterocycleoxy, heterocycleoxyalkyl, heterocyclesulfonyl or hydroxy, or $R^{27}$ and $R^{28}$ taken together with the atom to which they are attached form a heterocycle; and $R^{29}$ and $R^{30}$ are each independently hydrogen, alkyl, alkoxy, alkylsufonyl, aryl, arylalkyl, aryloxy, aryloxyalkyl, arylsulfonyl, carboxy, carboxyalkyl, cycloalkyl, cycloalkyloxy, carboxycycloalkyl, cycloalkylsulfonyl, heteroaryl, heteroarylalkyl, heteroaryloxy, heteroaryloxyalkyl, heteroarylsulfonyl, heterocycle, heterocyclealkyl, heterocycleoxy, heterocycleoxyalkyl, heterocyclesulfonyl or hydroxyl, or $R^{29}$ and $R^{30}$ taken together with the atom to which they are attached form a heterocycle; or a salt thereof.

14. The compound according to claim 13, wherein $A^2$, $A^3$, $A^4$, $R^1$ and $R^2$ are hydrogen; D is —O—; and E is biphenyl, cycloalkyl, heteroaryl or naphthyl.

15. The compound according to claim 13, wherein $A^2$, $A^3$, $A^4$, $R^1$ and $R^2$ are hydrogen; D is —O—; and E is heteroaryl.

16. The compound as in claim 13, wherein $A^1$ is —$CO_2R^{15}$ or —C(O)—N($R^{16}R^{17}$); $A^2$, $A^3$ and $A^4$ are each hydrogen; and E is naphthyl or biphenyl.

17. The compound according to claim 13, wherein $A^2$, $A^3$, $A^4$, $R^1$ and $R^2$ are hydrogen and $R^3$ and $R^4$ taken together with the atoms to which they are attached form a ring selected from the group consisting of cycloalkyl and heterocycle.

18. A compound of formula (I)

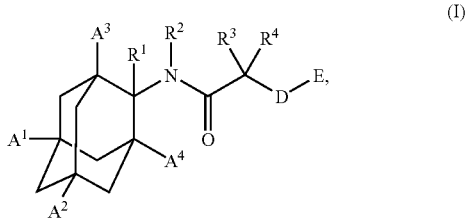

wherein
$A^1$ is alkenyl, alkyl-NH-heteroaryl, alkylcarbonyl, carboxycycloalkyl, cycloalkyl, cycloalkylcarbonyl, aryloxyalkyl, arylcarbonyl, heteroarylalkyl, heteroaryloxyalkyl, heterocyclealkyl, heterocycleoxyalkyl, heterocyclealkyloxyalkyl, imidazolyl, tetrazolyl, —C($R^{21}R^{22}$)—N($R^{23}R^{24}$), —C(=NOH)—N(H)$_2$; —C($R^{18a}R^{19a}$)—C(O)N($R^{23}R^{24}$), or —C($R^{18a}R^{19a}$)—S(O)$_2$—N($R^{25}R^{26}$);
$A^2$, $A^3$ and $A^4$, are hydrogen
D is —O—, —S—, —S(O)— or —S(O)$_2$—;
E is aryl, wherein aryl is phenyl or substituted phenyl;
$R^1$ is hydrogen or alkyl;
$R^2$ is hydrogen, alkyl or cycloalkyl;
$R^3$ and $R^4$ are each independently hydrogen, alkyl, carboxyalkyl, carboxycycloalkyl, cycloalkyl, haloalkyl, aryl, arylalkyl, heteroaryl, heteroarylalkyl, heterocycle or heterocyclealkyl, or $R^3$ and $R^4$ taken together with the atoms to which they are attached form a ring selected from the group consisting of cycloalkyl and heterocycle;
$R^{18a}$ and $R^{19a}$ are each independently hydrogen or alkyl;
$R^{201}$ and $R^{202}$ are independently hydrogen or alkyl;
$R^{21}$, $R^{22}$ and $R^{23}$ are hydrogen;
$R^{24}$ is alkoxy, alkylsulfonyl, aryl, arylcarbonyl, aryloxy, arylsulfonyl, carboxyalkyl, carboxycycloalkyl, cycloalkyl, cycloalkylcarbonyl, cycloalkyloxy, cycloalkylsulfonyl, heteroaryl, heteroarylcarbonyl, heteroaryloxy, heteroarylsulfonyl, heterocycle, heterocyclecarbonyl, heterocycleoxy, heterocyclesulfonyl or hydroxy, or $R^{23}$ and $R^{24}$ taken together with the atom to which they are attached form a ring of heteroaryl or heterocycle or a salt thereof 19. The compound according to claim 13, selected from the group consisting of
3E-4-({2-methyl-2-[(2-methylcyclohexyl)oxy]propanoyl}amino)adamantane-1carboxylic acid;
4E-4-({2-methyl-2-[(3-methylcyclohexyl)oxy]propanoyl}amino)adamantane-1-carboxylic acid;
5E-4-{[2-(cycloheptyloxy)-2-methylpropanoyl]amino)adamantane 1-carboxylic acid;
9E-4-({2-methyl-2-[(4-methylcyclohexyl)oxy]propanoyl}amino)adamantane-1-carboxamide;
E-4-({2-[(5-bromopyridin-2-yl)oxy]-2-methylpropanoyl}amino)adamantane-1-carboxamide;
59(E)-4-[(2-methyl-2-{[5-(1H-pyrazol-1-yl)pyridin-2-yl]oxy}propanoyl)amino]adamantane-1-carboxamide;
71E-4-({2-methyl-2-[(5-morpholin-4-ylpyridin-2-yl)oxy]propanoyl}amino)adamantane-1-carboxamide;
72E-4-{[2-methyl-2-(pyridin-2-yloxy)propanoyl]amino}adamantane-1-carboxamide;
E-4-[(2-{[5-(1H-imidazol-1-yl)pyridin-2-yl]oxy}-2-methylpropanoyl)amino]adamantane-1-carboxamide;
87E-4-[(2-methyl-2-{[(1S,2S)-2-methylcyclohexyl]oxy}propanoyl)amino]adamantane-1-carboxylic acid;
88E-4-({2-methyl-2-[(2-methylcyclohexyl)oxy]propanoyl}amino)adamantane-1-carboxamide;
89E-4-{[2-(cycloheptyloxy)-2-methylpropanoyl]amino}adamantane-1-carboxamide;
90E-4-{[2-(cyclohexylmethoxy)-2-methylpropanoyl]amino}adamantane-1-carboxamide;
91E-4-({2-methyl-2-[(3-methylcyclohexyl)oxy]propanoyl}amino)adamantane-1carboxamide;
E-4-({2-[(4,4-dimethylcyclohexyl)oxy]-2-methylpropanoyl}amino)adamantane-1-carboxylic acid;
E-4-{[2-methyl-2-(1,2,3,4-tetrahydronaphthalen-2-yloxy)propanoyl]amino}adamantane-1-carboxylic acid;
E-4-{[2-(1,1'-biphenyl -3-yloxy)-2-methylpropanoyl]amino}adamantane-1-carboxylic acid;
E-4-{[2-methyl-2-(1-naphthyloxy)propanoyl]amino}adamantane-1-carboxylic acid;
E-4-{[2-methyl-2-(2-naphthyloxy)propanoyl]amino}adamantane-1-carboxylic acid; or a salt thereof.

20. A compound selected from the group consisting of
E-4-[(2-methyl-2-{4-[(trifluoroacetyl)amino]phenoxy}propanoyl)amino]adamantane-1-carboxamide;
E-4-({244-(benzyloxy)phenoxy]-2-methylpropanoyl}amino)adamantane-1-carboxamide;
4-({[((E)-4-{[2-(4-chlorophenoxy)-2-methylpropanoyl]amino}-1-adamantyl)carbonyl]amino}methyl)benzoic acid;
E-N-[4-(aminocarbonyl)benzyl1]-4-{[2-(4-chlorophenoxy)-2-methylpropanoyl]amino}adamantane-1-carboxamide;
E-N-[4-(aminocarbonyl)methyl1]-4-{[2-(4-chlorophenoxy)-2-methylpropanoyl]amino}adamantine-1-carboxamide;
3-({[((E)-4-{[2-(4-chlorophenoxy)-2-methylpropanoyl]amino}-1-adamantyl)carbonyl]amino}methyl)benzoic acid;

4-{[({(E)-4-[(2-methyl-2-phenoxypropanoyl)amino]-1-adamantyl}carbonyl)amino]methyl}benzoic acid;

E-N-[4-(aminocarbonyl)benzyl1]-4-[(2-methyl-2-phenoxypropanoyl)amino]adamantane-1-carboxamide;

E-4-{[2-(4-chlorophenoxy)-2-methylpropanoyl]amino}-N-(1,3-thiazol-5-ylmethyl) adamantane-1-carboxamide;

E-4-{[2-(4-chlorophenoxy)-2-methylpropanoyl]amino}-N-(pyridin-4-ylmethyl) adamantane-1-carboxamide;

N-[(E)-5-(2-amino-2-oxoethyl)-2-adamantyl]-2-(4-chlorophenoxy)-2-methylpropanamide;

2-(4-chlorophenoxy)-2-methyl-N-[(E)-5-(2H-tetraazol-5-ylmethyl)-2-adamantyl]propanamide;

2-(4-chlorophenoxy)-2-methyl-N-{(E)-5-[(2-morpholin-4-ylethoxy)methyl1]-2-adamantyl}propanamide;

N-{(E)-5-[(Z)-amino(hydroxyimino)methyl1]-2-adamantyl}-2-(4-chlorophenoxy)-2-methylpropanamide;

2-(4-chlorophenoxy)-N-((E)-5-{[(4-methoxy-6-methylpyrimidin-2-yl)amino]methyl}-2-adamantyl)-2-methylpropanamide;

2-(4-chlorophenoxy)-N-[(E)-5-(1H-imidazol-2-yl)-2-adamantyl]-2-methylpropanamide;

2-(2-chloro-4-fluorophenoxy)-2-methyl-N-[(E)-5-(2H-tetraazol-5-yl)-2-adamantyl]propanamide;

E-N-[4-(aminosulfonyl)benzyl1]-4-{[2-(4-chlorophenoxy)-2-methylpropanoyl]amino}adamantane-1-carboxamide;

E-4-{[2-(4-chlorophenoxy)-2-methylpropanoyl]amino}-N-(4-{[(methylsulfonyl)amino]carbonyl}benzyl)adamantane-1-carboxamide;

N-{(E)-5-[(aminosulfonyl)methyl1]-2-adamantyl}-2-(4-chlorophenoxy)-2-methylpropanamide;

4-[({[((E)-4-{[2-(4-chlorophenoxy)-2-methylpropanoyl]amino}-1-adamantyl)methyl]sulfonyl}amino)methyl]benzoic acid;

E-4-({2-[4-chloro-2-(pyrrolidin-1-ylsulfonyl)phenoxy]-2-methylpropanoyl}amino) adamantane-1-carboxamide:

E-4-({2-methyl-2-[4-(methylsulfonyl)phenoxy]propanoyl}amino)adamantane-1-carboxamide;

E-4-({2-methyl-2-[2-(methylsulfonyl)phenoxy]propanoyl}amino)adamantane-1-carboxamide E-4-[(2-{4-chloro-2-[(diethylamino)sulfonyl]phenoxy}-2-methylpropanoyl)amino]adamantane--carboxamide;

E-4-({2-methyl-2[4-(pyrrolidin-1-ylsulfonyl)phenoxy]propanoyl}amino)adamantane-1-carboxamide;

E-4-({[1-(4-chlorophenoxy)cyclobutyl]carbonyl}amino) adamantane-1-carboxamide;

(2E)-3-((E)-4-{[2-(4-chlorophenoxy)-2-methylpropanoyl]amino}-1-adamantyl)acrylic acid;

2-(4-chlorophenoxy)-2-methyl-N-[(E)-5-(1H-pyrazol-3-yl)-2-adamantyl]propanamide;

E-4-({2-methyl-2-[(7-methyl-2,3-dihydro-1H-inden-4-yl)oxy]propanoyl}amino) adamantane-1-carboxylic acid;

E-4-{[2-(4-{[(tert-butylamino)carbonyl]amino}phenoxy)-2-methylpropanoyl]amino}adamantane-1-carboxamide;

E-4-[(2-methyl-2-{4-[(propylsulfonyl)amino]phenoxy}propanoyl)amino]adamantane-1-carboxamide;

E-4-[(2-{4-[(3,3-dimethylbutanoyl)amino]phenoxy}-2-methylpropanoyl)amino]adamantane-1-carboxamide; and 2-[(4-methoxyphenyl)sulfonyl]-2-methyl-N-[(E)-5-(2H-tetraazol-5-yl)-2-adamantyl]propanamide; or a salt thereof 21. A pharmaceutical composition comprising a therapeutically effective amount of the compound of formula (I) of claim 13, in combination with a pharmaceutically suitable carrier.

22. A method of inhibiting 11-beta-hydroxysteroid dehydrogenase Type I enzyme, comprising administering to a mammal, a therapeutically effective amount of the compound of formula (I) of claim 13.

23. The compound according to claim 13, that is 3E-4-({2-methyl-2-[(2-methylcyclohexyl)oxy]propanoyl}amino)adamantane-1-carboxylic acid; or a salt thereof.

24. The compound according to claim 13, that is 4E-4-({2-methyl-2-[(3-methylcyclohexyl)oxy]propanoyl}amino)adamantane-1-carboxylic acid; or a salt thereof.

25. The compound according to claim 13, that is 5E-4-{[2-(cycloheptyloxy)-2-methylpropanoyl]amino}adamantane-1-carboxylic acid; or a salt thereof.

26. The compound according to claim 13, that is 9E-4-({2-methyl-2-[(4-methylcyclohexyl)oxy]propanoyl}amino)adamantane-1-carboxamide; or a salt thereof.

27. The compound according to claim 13, that is E-4-({2-[(5-bromopyridin-2-yl)oxy]-2-methylpropanoyl amino)adamantane-1-carboxamide; or a salt thereof.

28. The compound according to claim 13, that is 59(E)-4-[(2-methyl-2-{[5-(1H-pyrazol-1-yl)pyridin-2-yl]oxy}propanoyl) amino]adamantane-1-carboxamide; or a salt thereof 29. The compound according to claim 13, that is 71E-4-({2-methyl-2-[(5-morpholin-4-ylpyridin-2-yl)oxy] propanoyl}amino)adamantane-1-carboxamide; or a salt thereof.

30. The compound according to claim 13, that is 72E-4-{[2-methyl-2-(pyridin-2-yloxy)propanoyl] amino}adamantane-1-carboxamide; or a salt thereof.

31. The compound according to claim 13, that is E-4-[(2-{[5-(1H -imidazol-1-yl)pyridin-2-yl]oxy}-2-methylpropanoyl) amino]adamantane-1-carboxamide; or a salt thereof.

32. The compound according to claim 13, that is 87E-4-[(2-methyl-2-{[(1S ,2S)-2-methylcyclohexyl]oxy}propanoyl)amino]adamantane-1-carboxylic acid; or a salt thereof.

33. The compound according to claim 13, that is 88E-4-({2-methyl-2-[(2-methylcyclohexyl)oxy]propanoyl}amino) adamantane-1-carboxamide; or a salt thereof.

34. The compound according to claim 13, that is 89E-4-{[2-(cycloheptyloxy)-2-methylpropanoyl] amino}adamantane-1-carboxamide; or a salt Thereof.

35. The compound according to claim 13, that is 90E-4-{[2-(cyclohexylmethoxy)-2-methylpropanoyl] amino}adamantane-1-carboxamide; or a salt thereof.

* * * * *

UNITED STATES PATENT AND TRADEMARK OFFICE
CERTIFICATE OF CORRECTION

PATENT NO. : 7,855,308 B2
APPLICATION NO. : 12/355909
DATED : December 21, 2010
INVENTOR(S) : Michael E. Brune et al.

It is certified that error appears in the above-identified patent and that said Letters Patent is hereby corrected as shown below:

In column 2 on page 1, US patent application publication 2006/0079506 should read as follows:

-- 2006/0079506  07/2006  Linders, et al. --

In column 7, line 6 should read as follows:

-- $A^2$ $A^3$ and $A^4$ are hydrogen; --

In column 7, line 37 should read as follows:

-- $A^2$ $A^3$ and $A^4$ are hydrogen; --

Signed and Sealed this
Thirty-first Day of January, 2012

David J. Kappos
*Director of the United States Patent and Trademark Office*